(12) United States Patent
Jung et al.

(10) Patent No.: US 8,383,932 B2
(45) Date of Patent: Feb. 26, 2013

(54) COMPOUND FOR ORGANIC PHOTOELECTRIC DEVICE AND ORGANIC PHOTOELECTRIC DEVICE INCLUDING THE SAME

(75) Inventors: Ho-Kuk Jung, Incheon (KR); Myeong-Soon Kang, Suwon-si (KR); Jin-Seong Park, Anyang-si (KR); Nam-Soo Kim, Bucheong-si (KR); Kyu-Yeol In, Uiwang-si (KR); Eiu-Su Kang, Anyang-si (KR); Mi-Young Chae, Yongin-si (KR)

(73) Assignee: Cheil Industries, Inc., Gumi-si, Gyeongsangbuk-do (KR)

( * ) Notice: Subject to any disclaimer, the term of this patent is extended or adjusted under 35 U.S.C. 154(b) by 270 days.

(21) Appl. No.: 12/662,450

(22) Filed: Apr. 19, 2010

(65) Prior Publication Data

US 2010/0200054 A1 Aug. 12, 2010

Related U.S. Application Data

(63) Continuation of application No. PCT/KR2008/006175, filed on Oct. 17, 2008.

(30) Foreign Application Priority Data

| Oct. 17, 2007 | (KR) | 10-2007-0104541 |
| Sep. 1, 2008 | (KR) | 10-2008-0085904 |
| Oct. 8, 2008 | (KR) | 10-2008-0098769 |

(51) Int. Cl.
*H01L 31/00* (2006.01)

(52) U.S. Cl. ........ 136/256; 546/256; 546/270.1; 546/271.7; 548/145

(58) Field of Classification Search ........... 136/256; 546/256, 270.1, 271.7; 548/145
See application file for complete search history.

(56) References Cited

U.S. PATENT DOCUMENTS

| 5,645,948 | A | 7/1997 | Shi et al. |
| 6,878,469 | B2 | 4/2005 | Yoon et al. |
| 2002/0028329 | A1 | 3/2002 | Ise et al. |
| 2002/0037427 | A1* | 3/2002 | Taguchi ............ 428/690 |
| 2004/0166365 | A1 | 8/2004 | Ise et al. |
| 2005/0164032 | A1 | 7/2005 | Ise et al. |
| 2005/0260452 | A1 | 11/2005 | Ise et al. |
| 2006/0068223 | A1 | 3/2006 | Nariyuki et al. |
| 2006/0110840 | A1* | 5/2006 | Araki ................ 438/22 |
| 2007/0069638 | A1 | 3/2007 | Matsuura et al. |
| 2007/0200490 | A1 | 8/2007 | Kawamura et al. |
| 2008/0287583 | A1* | 11/2008 | Mataki et al. ......... 524/403 |
| 2010/0044638 | A1 | 2/2010 | Ise et al. |

FOREIGN PATENT DOCUMENTS

| EP | 0 825 804 B1 | 1/2002 |
| EP | 1 175 128 A2 | 1/2002 |
| EP | 1 923 930 A1 | 5/2008 |

(Continued)

OTHER PUBLICATIONS

Extended European Search Report issued in corresponding application, EP 08 83 9815, dated Mar. 1, 2012.

*Primary Examiner* — Shane Fang
(74) *Attorney, Agent, or Firm* — Lee & Morse, P.C.

(57) ABSTRACT

A compound for an organic photoelectric device, represented by the following Chemical Formula 1:

[Chemical Formula 1]

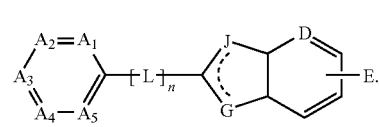

17 Claims, 24 Drawing Sheets

FOREIGN PATENT DOCUMENTS

| | | |
|---|---|---|
| EP | 2 224 790 A1 | 9/2010 |
| JP | 2001-288172 A | 1/2001 |
| JP | 2002-038141 A | 2/2002 |
| JP | 2002-212181 A | 7/2002 |
| KR | 10-2006-0023046 A | 3/2006 |
| KR | 10-2007-0023676 A | 2/2007 |

* cited by examiner

COMPOUND FOR ORGANIC PHOTOELECTRIC DEVICE AND ORGANIC PHOTOELECTRIC DEVICE INCLUDING THE SAME

CROSS-REFERENCE TO RELATED APPLICATION

This application is a continuation of pending International Application No. PCT/KR2008/006175, entitled "Compound For Organic Photoelectric Device and Organic Photoelectric Device Including the Same," which was filed on Oct. 17, 2008, the entire contents of which are hereby incorporated by reference.

1. Field

Embodiments relate to a compound for an organic photoelectric device and an organic photoelectric device including the same.

2. Description of the Background Art

An organic photoelectric device may be used to transform electrical energy into light through application of an electrical current to an organic light emitting material. The organic photoelectric device may have a structure in which a functional organic material layer is interposed between an anode and a cathode.

An organic light emitting diode has similar electrical characteristics to those of light emitting diodes (LEDs), in which holes are injected from an anode and electrons are injected from a cathode, then the holes and electrons move to opposite electrodes and are recombined to form excitons having high energy. The formed excitons may then generate light having a certain wavelength while shifting to a ground state.

Light emission of an anthracene organic material was shown in 1960, but only under application of a disadvantageously high driving voltage. In 1980, C. W. Tang et al., of Eastman Kodak, Inc., developed a device with a low driving voltage. Thereafter, in 1990, Cambridge University developed a polymer light emitting diode using poly(p-phenylenevinylene) (PPV). Research has been conducted on a low molecular weight light emitting element (SMOLED) and a polymer, or high molecular weight organic light emitting diode (POLED). The low molecular weight organic light emitting diode may be manufactured as a thin film using a vacuum deposition method, and may have good efficiency and life-span performance. A polymer organic light emitting diode may manufactured using an inkjet or spin coating method, which may have advantages of low initial cost and suitability to large-sized panels.

Both low molecular weight organic light emitting and polymer organic light emitting diodes may have advantages of being self-light emitting and ultrathin, and having a high speed response, a wide viewing angle, high image quality, durability, a large driving temperature range, and the like. In particular, they may have good visibility due to the self-light emitting characteristic compared with a conventional LCD (liquid crystal display) and have an advantage of decreasing thickness and weight of LCD by up to a third, because they do not need a backlight. In addition, since they have a response speed of a few microseconds that may be 1000 times faster than an LCD, they may be used to form motion pictures without an after-image. Further, they have been significantly developed, and may have 80 times the efficiency and more than 100 times the life-span since they were first developed in the late 1980s. Recently, these diodes have been used in displays that are rapidly becoming larger, such as for a 40-inch organic light emitting diode panel.

SUMMARY

It is a feature of an embodiment to provide a compound that can act as a hole injection, hole transport, light emitting, or electron injection and/or transport material.

It is another feature of an embodiment to provide a compound that can act as a light emitting host along with a dopant.

It is another feature of an embodiment to provide an organic photoelectric device including the compound for an organic photoelectric device, and having decreased driving voltage and increased life-span and efficiency.

At least one of the above and other features and advantages may be realized by providing a compound for an organic photoelectric device, represented by the following Chemical Formula 1:

[Chemical Formula 1]

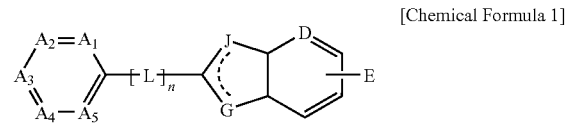

wherein, in Chemical Formula 1, $A_1$ to $A_5$ are the same or different, and are $CR_1$ to $CR_5$ or N, provided that three or less of $A_1$ to $A_5$ are N, when one of $A_1$ to $A_5$ is N, the remaining four of $A_1$ to $A_5$ are respectively selected from the group of $CR_1$ to $CR_5$, provided that at least two of $R_1$ to $R_5$ are not hydrogen, and when $A_1$ to $A_5$ are respectively $CR_1$ to $CR_5$, at least two of $R_1$ to $R_5$ are not hydrogen, G is selected from the group of O, S, Se, and NR'', J and D are the same or different, and are independently selected from the group of CR' and N, provided that when G is not NR'', J is N, $R_1$ to $R_5$, R', and R'' are independently selected from the group of hydrogen, a halogen, a nitrile, a cyano, a nitro, an amide, a carbonyl, an ester, a substituted or unsubstituted alkyl, a substituted or unsubstituted alkoxy, a substituted or unsubstituted alkenyl, a substituted or unsubstituted cycloalkyl, a substituted or unsubstituted aryl, a substituted or unsubstituted arylamine, a substituted or unsubstituted heteroarylamine, a substituted or unsubstituted heterocycle, a substituted or unsubstituted amino, $BR_6R_7$, and $SiR_6R_7R_8$, where $R_6$ to $R_8$ are the same or different, and are independently selected from the group of a substituted or unsubstituted alkyl, and a substituted or unsubstituted aryl, E is selected from the group of hydrogen, a nitrile, a cyano, a nitro, an amide, a carbonyl, a substituted or unsubstituted alkyl, a substituted or unsubstituted fluoroalkyl, a substituted or unsubstituted cycloalkyl, a substituted or unsubstituted aryl, a substituted or unsubstituted heterocycle, and $SO_2R_9$, where $R_9$ is selected from the group of a nitrile, a cyano, a nitro, an amide, a carbonyl, a substituted or unsubstituted alkyl, a substituted or unsubstituted cycloalkyl, a substituted or unsubstituted aryl, and a substituted or unsubstituted heterocycle, L is selected from the group of a substituted or unsubstituted aryl and a substituted or unsubstituted heteroaryl, and n is 0 or 1.

The compound may be represented by the following Chemical Formula 2:

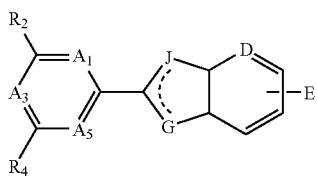

[Chemical Formula 2]

wherein, in Chemical Formula 2, $A_1$, $A_3$, and $A_5$ are the same or different, and are $CR_1$, $CR_3$, and $CR_5$, or N, where $R_1$, $R_3$, and $R_5$ are the same or different and are selected from the group of hydrogen and a substituted or unsubstituted alkyl, G is selected from the group of O, S, Se, and NR", J and D are the same or different, and are independently selected from the group of CR' and N, provided that when G is not NR", J is N, where R' and R" are the same or different, and are independently selected from the group of a nitrile, a cyano, a nitro, an amide, a carbonyl, a substituted or unsubstituted alkyl, a substituted or unsubstituted cycloalkyl, a substituted or unsubstituted aryl, and a substituted or unsubstituted heterocycle, $R_2$ and $R_4$ are the same or different, and are independently selected from the group of hydrogen, a halogen, a nitrile, a cyano, a nitro, an amide, a carbonyl, an ester, a substituted or unsubstituted alkyl, a substituted or unsubstituted alkoxy, a substituted or unsubstituted alkenyl, a substituted or unsubstituted cycloalkyl, a substituted or unsubstituted aryl, a substituted or unsubstituted arylamine, a substituted or unsubstituted heteroarylamine, a substituted or unsubstituted heterocycle, a substituted or unsubstituted amino, $BR_6R_7$, and $SiR_6R_7R_8$, where $R_6$ to $R_8$ are the same or different, and are independently selected from the group of a substituted or unsubstituted alkyl, and a substituted or unsubstituted aryl, and E is selected from the group of hydrogen, a nitrile, a cyano, a nitro, an amide, a carbonyl, a substituted or unsubstituted alkyl, a substituted or unsubstituted fluoroalkyl, a substituted or unsubstituted cycloalkyl, a substituted or unsubstituted aryl, a substituted or unsubstituted heterocycle, and $SO_2R_9$, where $R_9$ is selected from the group of a nitrile, a cyano, a nitro, an amide, a carbonyl, a substituted or unsubstituted alkyl, a substituted or unsubstituted cycloalkyl, a substituted or unsubstituted aryl, and a substituted or unsubstituted heterocycle.

$R_2$ and $R_4$ of Chemical Formula 2 may be different from each other.

The compound may have an asymmetric structure where upper and lower substituents are different from each other with respect to the axis including $A_3$.

The $A_1$ and $A_5$ may be different from each other, and $A_2$ and $A_4$ may be different.

$R_1$ to $R_5$, R', and R" of Chemical Formula 1 may be independently a substituted or unsubstituted C6 to C40 aryl.

$R_1$ to $R_5$, R', and R" may be independently an arylamine selected from the group of diphenyl amine, dinaphthyl amine, dibiphenyl amine, phenyl naphthyl amine, phenyl diphenyl amine, ditolyl amine, phenyl tolyl amine, carbazole, and triphenyl amine.

$R_1$ to $R_5$, R', and R" may be a substituted or unsubstituted heterocycle selected from the group of thiophene, furan, pyrrole, imidazolyl, thiazolyl, oxazolyl, oxadiazolyl, triazolyl, pyridinyl, pyridazine, quinolinyl, isoquinolinine, acridyl, imidazopyridinyl, and imidazopyrimidinyl.

When the substituted or unsubstituted heterocycle is imidazole or triazole, the substituent linked to nitrogen (N) of the imidazole or triazole may be selected from the group of a substituted or unsubstituted alkyl, a substituted or unsubstituted cycloalkyl, a substituted or unsubstituted aryl, and a substituted or unsubstituted heterocycle.

One selected from $R_1$ to $R_5$, R', and R" of G of the Formula 1 may include a substituent selected from the group of an amine substituted alkyl, an amine substituted cycloalkyl, an amine substituted aryl, and an amine substituted heterocycle, and the other from $R_1$ to $R_5$, R', and R" of G of the Formula 1 may include a substituent selected from the group of a nitrile, a nitro, an amide, a carbonyl, and a substituted or unsubstituted heterocycle.

At least one of the above and other features and advantages may also be realized by providing an organic photoelectric device, including an anode, a cathode, and at least one organic layer interposed between the anode and cathode, wherein the at least one organic layer includes the compound for an organic photoelectric device according to an embodiment.

The compound for an organic photoelectric device may be a host material or a charge transport material.

The at least one organic layer may include at least one of an emission layer, a hole transport layer (HTL), a hole injection layer (HIL), an electron transport layer (ETL), and an electron injection layer (EIL).

The at least one organic layer may include the compound for an organic photoelectric device and a reducing dopant.

The reducing dopant may include at least one of an alkaline metal, an alkaline earth metal, a rare earth element metal, an oxide of an alkaline metal, a halide of an alkaline metal, an organic complex of an alkaline metal, an oxide of an alkaline earth metal, a halide of an alkaline earth metal, an organic complex of an alkaline earth metal, an oxide of an alkaline earth metal, a halide of an alkaline earth metal, an organic complex of an alkaline earth metal, an oxide of a rare earth element metal, a halide of a rare earth element metal, and an organic complex of a rare earth element metal.

At least one of the above and other features and advantages may also be realized by providing a display device including the organic photoelectric device according to an embodiment.

BRIEF DESCRIPTION OF THE DRAWINGS

The above and other features and advantages will become more apparent to those of skill in the art by describing in detail example embodiments with reference to the attached drawings, in which.

Figure 1:
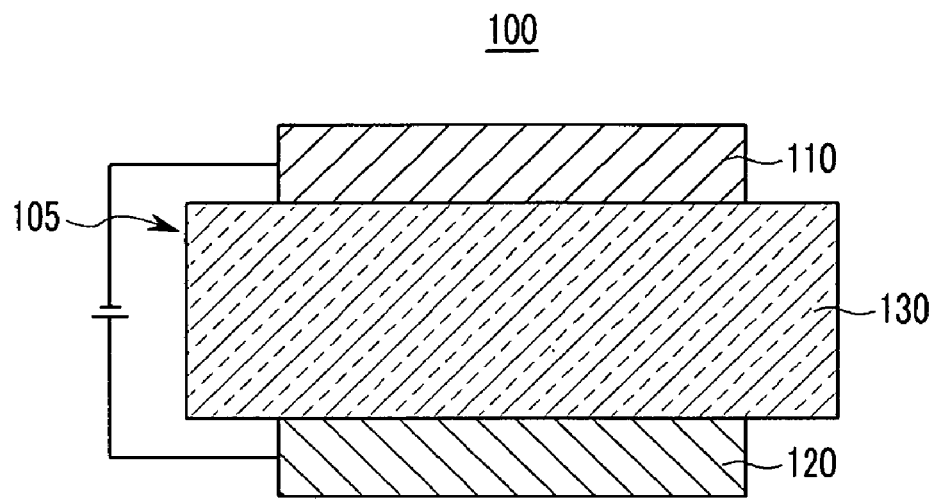
FIGS. 1 to 5 illustrate cross-sectional views showing organic photoelectric devices including organic compounds according to various embodiments.

<Description of Reference Numerals Indicating Elements in the Drawings>

| | |
|---|---|
| 100: organic photoelectric device | 110: cathode |
| 120: anode | 105: organic thin layer |
| 130: emission layer | 140: hole transport layer (HTL) |
| 150: electron transport layer (ETL) | 160: electron injection layer (EIL) |
| 170: hole injection layer (HIL) | 230: emission layer + electron transport layer (ETL) |

DETAILED DESCRIPTION

Korean Patent Application Nos. 10-2007-0104541, filed on Oct. 17, 2007, 10-2008-0085904, filed on Sep. 1, 2008, and 10-2008-0098769, filed on Oct. 8, 2008, in the Korean Intellectual Property Office, and entitled: "Compound for Organic Photoelectric Device and Organic Photoelectric Device Including the Same," are each entirely incorporated by reference herein.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the invention to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

As used herein, when specific definition is not provided, "an alkyl" may refer to a C1-C30 alkyl, and preferably a C1-C20 alkyl, and more preferably a C1 to C15 alkyl; "an alkoxy" may refer to a C1 to C30 alkoxy, and preferably C1 to C20 alkoxy, and more preferably a C1 to C15 alkoxy; "an alkenyl" may refer to a C2 to C30 alkenyl, and preferably a C2 to C20 alkenyl, and more preferably a C2 to C15 alkenyl; "a cycloalkyl" may refer to a C3 to C30 cycloalkyl, and preferably a C3 to C20 cycloalkyl, and more preferably a C3 to C15 cycloalkyl; "an aryl" may refer to a C6 to C50 aryl, and preferably a C6 to C40 aryl, and more preferably a C6 to C25 aryl; "an arylamine" may refer to a C7 to C50 arylamine, and preferably a C7 to C25 arylamine; "a heteroarylamine" may refer to a C7 to C50 heteroarylamine, and preferably a C7 to C25 heteroarylamine; "a heterocycle" may refer to a C2 to C50 heterocycle, and preferably a C2 to C25 heterocycle, and more preferably a C2 to C20 heterocycle; and "a fluoroalkyl" may refer to a C1 to C10 fluoroalkyl.

As used herein, when specific definition is not provided, the term "substituted" may refer to one substituted with at least a substituent selected from the group of a halogen, a nitrile, a cyano, a nitro, an amide, a carbonyl, an acetylene, a substituted or unsubstituted alkyl, a substituted or unsubstituted alkenyl, a substituted or unsubstituted alkoxy, a substituted or unsubstituted arylamine, a substituted or unsubstituted aryl, a substituted or unsubstituted arylalkyl, a substituted or unsubstituted arylalkenyl, a substituted or unsubstituted heterocycle, a substituted or unsubstituted amine, a substituted or unsubstituted cycloalkyl, $BR_6R_7$, and $SiR_6R_7R_8$, where $R_6$ to $R_8$ are the same or different and are independently selected from the group of a substituted or unsubstituted C1 to C30 alkyl and a substituted or unsubstituted C6 to C50 aryl.

As used herein, when specific definition is not provided, the term "hetero" may refer to one including 1 to 3, including N, O, S, P, or Si, in one ring.

As used herein, when specific definition is not provided, the term "heterocycle", may refer to one selected from the group of a C3 to C50 heteroaryl, a C2 to C50 heterocycloalkyl, a C3 to C50 heterocycloalkenyl, a C3 to C50 heterocycloalkynyl, and fused rings thereof. The heterocycle preferably includes 1 to 20 heteroatoms, and more preferably 1 to 15 heteroatoms.

Herein, Markush groups, if any, are identified by the closed language "selected from the group consisting of."

According to an embodiment, a compound for an organic photoelectric device is largely asymmetric. The asymmetric structure reinforces an amorphous characteristic and thereby suppresses crystallization, improving thermal stability of the compound for an organic photoelectric device. Accordingly, when an organic photoelectric device is driven, the compound may decrease the driving voltage and improve life-span and efficiency of the organic photoelectric device.

The compound according to an embodiment may be used as a hole injection, hole transport, light emitting, or electron injection and/or transport material. The compound according to an embodiment may be used as a light emitting host along with a dopant.

An embodiment provides a compound for an organic photoelectric device, the compound being represented by the following Chemical Formula 1.

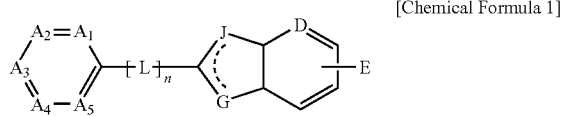

[Chemical Formula 1]

In Chemical Formula 1, $A_1$ to $A_5$ are the same or different, and are $CR_1$ to $CR_5$ or N, provided that three or less of $A_1$ to $A_5$ are N (herein, $CR_1$ to $CR_5$ includes $CR_1$, $CR_2$, $CR_3$, $CR_4$, and $CR_5$).

In Chemical Formula 1, when one of $A_1$ to $A_5$ is N, the remaining four of $A_1$ to $A_5$ are respectively selected from the group of $CR_1$ to $CR_5$, provided that at least two of $R_1$ to $R_5$ are not hydrogen (herein, $R_1$ to $R_5$ includes $R_1$, $R_2$, $R_3$, $R_4$, and $R_5$). When $A_1$ to $A_5$ are respectively $CR_1$ to $CR_5$, at least two of $R_1$ to $R_5$ are not hydrogen.

In Chemical Formula 1, G is selected from the group of O, S, Se, and NR".

In Chemical Formula 1, J and D are the same or different, and are independently selected from the group of CR' and N, provided that when G is not NR", J is N. The right-hand moiety as a whole (i.e., the fused ring system) is π-bonded.

$R_1$ to $R_5$, R', and R" are the same or different, and are independently selected from the group of hydrogen, a halogen, a nitrile, a cyano, a nitro, an amide, a carbonyl, an ester, a substituted or unsubstituted alkyl, a substituted or unsubstituted alkoxy, a substituted or unsubstituted alkenyl, a substituted or unsubstituted cycloalkyl, a substituted or unsubstituted aryl, a substituted or unsubstituted arylamine, a substituted or unsubstituted heteroarylamine, a substituted or unsubstituted heterocycle, a substituted or unsubstituted amino, $BR_6R_7$, and $SiR_6R_7R_8$, where $R_6$ to $R_8$ are the same or different, and are independently selected from the group of a substituted or unsubstituted alkyl, and a substituted or unsubstituted aryl.

In Chemical Formula 1, E is selected from the group of hydrogen, a nitrile, a cyano, a nitro, an amide, a carbonyl, a substituted or unsubstituted alkyl, a substituted or unsubstituted fluoroalkyl, a substituted or unsubstituted cycloalkyl, a substituted or unsubstituted aryl, a substituted or unsubstituted heterocycle, and $SO_2R_9$, $R_9$ is selected from the group of a nitrile, a cyano, a nitro, an amide, a carbonyl, a substituted or unsubstituted alkyl, a substituted or unsubstituted cycloalkyl, a substituted or unsubstituted aryl, and a substituted or unsubstituted heterocycle.

In Chemical Formula 1, L is selected from the group of a substituted or unsubstituted aryl, and a substituted or unsubstituted heteroaryl.

In Chemical Formula 1, n is 0 or 1.

The compound for an organic photoelectric device of Chemical Formula 1 includes a part including $A_1$ to $A_5$, a linking group of L including an aryl group or a heteroaryl group, and a functional substituent including a five-member ring.

In Chemical Formula 1, $A_1$ to $A_5$ are the same or different, and $CR_1$ to $CR_5$ are N, provided that three or less of $A_1$ to $A_5$ are N.

When one or more of $A_1$ to $A_5$ is N, it can lower the LUMO (lowest unoccupied molecular orbital) energy level and increase electron affinity of a molecule, and thereby improve injection and transfer characteristics of electrons. Accordingly, the voltage required for driving an organic light emitting diode may be reduced and electric power efficiency may be improved. When more than four among $A_1$ to $A_5$ are N, it may result in a LUMO energy level that is too low, such that it is hard to inject electrons.

When one among $A_1$ to $A_5$ is N, four among $A_1$ to $A_5$ are respectively selected from the group of $CR_1$ to $CR_5$. Herein, at least two among the $R_1$ to $R_5$ are not hydrogen. When one among the $R_1$ to $R_5$ is not hydrogen but is a substituent, it can increase rigidity of the compound and easily cause crystallization. When the $R_1$ to $R_5$ are all hydrogen, it may decrease thermal stability, and it may also be hard to inject electrons.

When $A_1$ to $A_5$ are not N, $A_1$ to $A_5$ are selected from the group of $CR_1$ to $CR_5$. In an implementation, at least two among the $R_1$ to $R_5$ are not hydrogen. When one among the $R_1$ to $R_5$ is not hydrogen but is a substituent, it may increase rigidity of the compound. When the $R_1$ to $R_5$ are all hydrogen, it may decrease thermal stability, and it may also be hard to inject electrons.

In particular, when at least two among the $R_1$ to $R_5$ are not hydrogen but are a substituent, it may increase the amorphous characteristic by introducing a different substituent into a position of the substituent. Accordingly, it may suppress crystallization caused by the Joule heat generated from a device during operation, and thereby improve the life-span characteristic of an organic light emitting diode.

The linking group, L, may include an aryl group or a heteroaryl group, and may increase interaction among molecules to thereby improve thermal stability. In addition, it may adjust the π-conjugation length and light emission in a visual region. Accordingly, a compound for an organic photoelectric device according to an embodiment may be used for an emission layer.

G is a functional substituent included in a five-member ring, and is selected from the group of O, S, Se, and NR". J and D are different or the same as each other, and are independently selected from the group of CR' and N. However, when G is not NR", J is N. The functional substituent included in the five-member ring may make the structure generally asymmetric and may thereby endow the compound for an organic photoelectric device with thermal stability.

A compound for an organic photoelectric device according to an embodiment is represented by the following Formula 2.

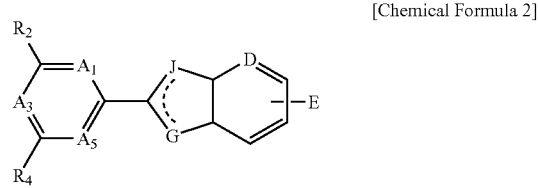

[Chemical Formula 2]

In Chemical Formula 2, $A_1$, $A_3$, and $A_5$ are the same or different, and are $CR_1$, $CR_3$, and $CR_5$, or N, where $R_1$, $R_3$, and $R_5$ are the same or different and are selected from the group of hydrogen and a substituted or unsubstituted alkyl.

In Chemical Formula 2, G is selected from the group of O, S, Se, and NR".

In Chemical Formula 2, J and D are the same or different, and are independently selected from the group of CR' and N, provided that when G is not NR", J is N.

R' and R" are the same or different, and are independently selected from the group of a nitrile, a cyano, a nitro, an amide, a carbonyl, a substituted or unsubstituted alkyl, a substituted or unsubstituted cycloalkyl, a substituted or unsubstituted aryl, and a substituted or unsubstituted heterocycle.

$R_2$ and $R_4$ are the same or different, and are independently selected from the group of hydrogen, a halogen, a nitrile, a cyano, a nitro, an amide, a carbonyl, an ester, a substituted or unsubstituted alkyl, a substituted or unsubstituted alkoxy, a substituted or unsubstituted alkenyl, a substituted or unsubstituted cycloalkyl, a substituted or unsubstituted aryl, a substituted or unsubstituted arylamine, a substituted or unsubstituted heteroarylamine, a substituted or unsubstituted heterocycle, a substituted or unsubstituted amino, $BR_6R_7$, and $SiR_6R_7R_8$, where $R_6$ to $R_8$ are the same or different, and are independently selected from the group of a substituted or unsubstituted alkyl, and a substituted or unsubstituted aryl, provided that $R_2$ and $R_4$ are not simultaneously hydrogen.

It is preferable that $R_2$ and $R_4$ are the same or different, and are independently selected from the group of a nitrile, a nitro, an amide, a carbonyl, a substituted or unsubstituted alkyl, a substituted or unsubstituted alkenyl, a substituted or unsubstituted cycloalkyl, a substituted or unsubstituted aryl, a substituted or unsubstituted arylamine, a substituted or unsubstituted heterocycle, $BR_6R_7$, and $SiR_6R_7R_8$, where $R_6$ to $R_8$ are the same or different, and are independently selected from the group of a substituted or unsubstituted alkyl and a substituted or unsubstituted aryl.

It is more preferable that $R_2$ and $R_4$ are functional groups having excellent electron injection characteristics or functional groups being capable of improving thermal stability. In an embodiment, $R_2$ and $R_4$ are not simultaneously hydrogen, and preferably $R_2$ and $R_4$ are not the same.

Examples of $R_2$ in Chemical Formula 2 include the groups represented by the following Chemical Formulae 3 to 23.

[Chemical Formula 3]

[Chemical Formula 4]

[Chemical Formula 5]

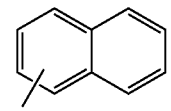
[Chemical Formula 6]

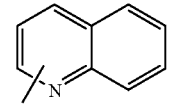
[Chemical Formula 7]

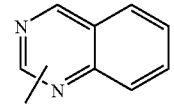
[Chemical Formula 8]

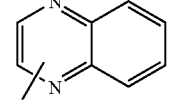
[Chemical Formula 9]

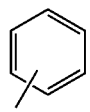
[Chemical Formula 10]

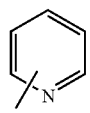
[Chemical Formula 11]

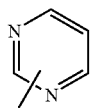
[Chemical Formula 12]

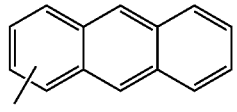
[Chemical Formula 13]

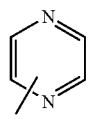
[Chemical Formula 14]

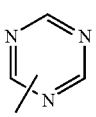
[Chemical Formula 15]

[Chemical Formula 16]

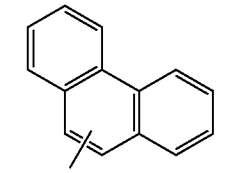
[Chemical Formula 17]

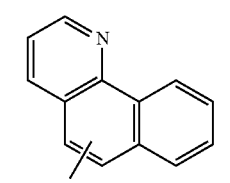
[Chemical Formula 18]

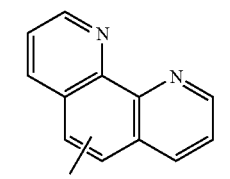
[Chemical Formula 19]

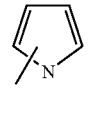
[Chemical Formula 20]

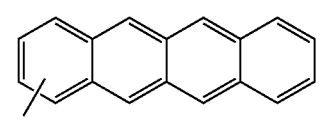
[Chemical Formula 21]

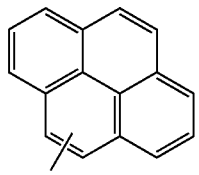
[Chemical Formula 22]

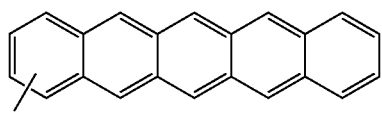
[Chemical Formula 23]

Examples of $R_4$ in Chemical Formula 2 include the groups represented by Chemical Formulae 3 to 23 or the compounds represented by the following Chemical Formulae 24 to 65.

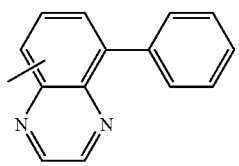
[Chemical Formula 24]

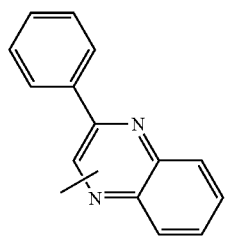
[Chemical Formula 25]

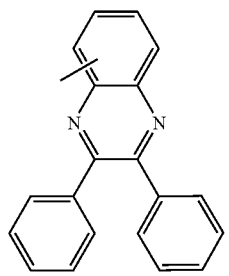
[Chemical Formula 26]

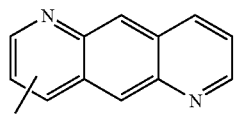
[Chemical Formula 27]

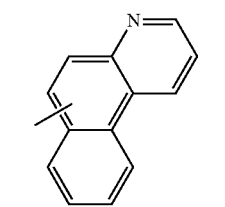
[Chemical Formula 28]

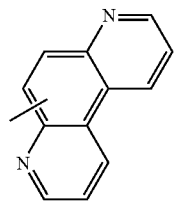
[Chemical Formula 29]

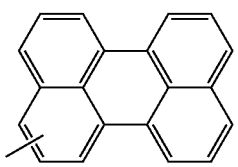
[Chemical Formula 30]

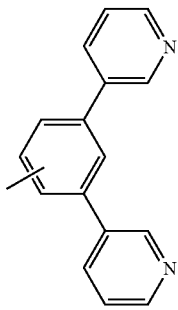
[Chemical Formula 31]

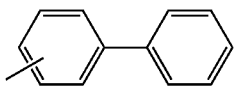
[Chemical Formula 32]

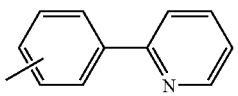
[Chemical Formula 33]

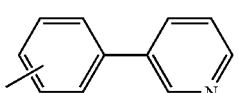
[Chemical Formula 34]

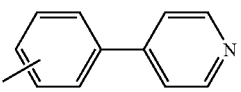
[Chemical Formula 35]

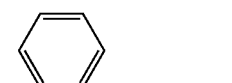
[Chemical Formula 36]

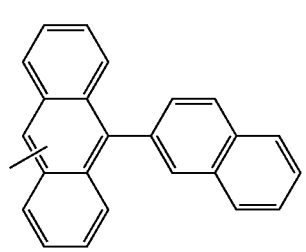
[Chemical Formula 37]

[Chemical Formula 38]
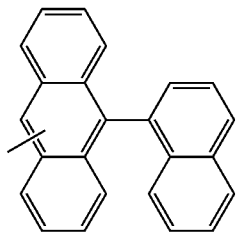
[Chemical Formula 39]
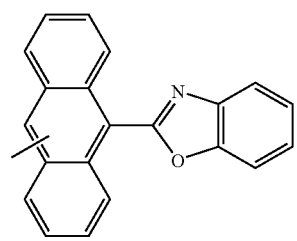
[Chemical Formula 40]
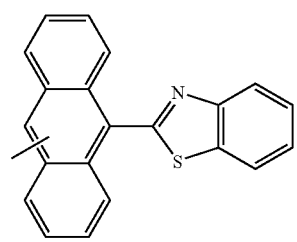
[Chemical Formula 41]
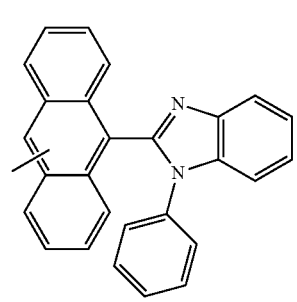
[Chemical Formula 42]
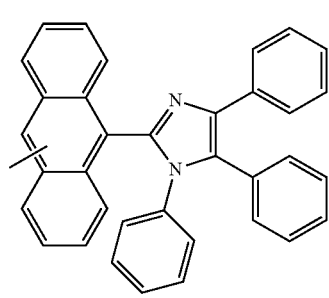
[Chemical Formula 43]
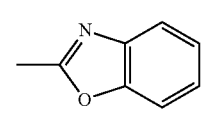
[Chemical Formula 44]
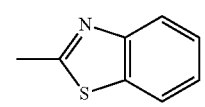
[Chemical Formula 45]
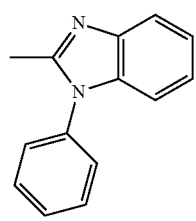
[Chemical Formula 46]
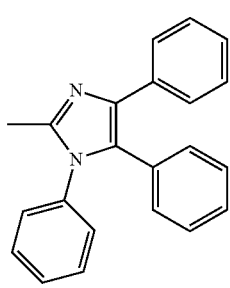
[Chemical Formula 47]
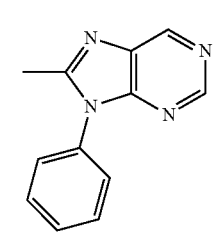
[Chemical Formula 48]
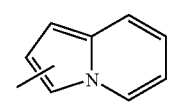
[Chemical Formula 49]
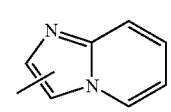
[Chemical Formula 50]
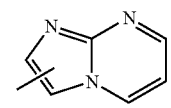
[Chemical Formula 51]
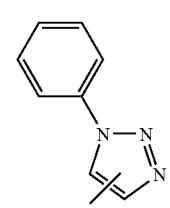
[Chemical Formula 52]
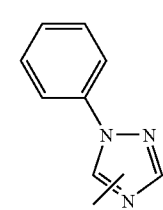

[Chemical Formula 53]
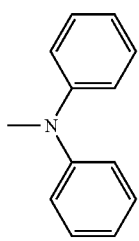
[Chemical Formula 54]
[Chemical Formula 55]
[Chemical Formula 56]
[Chemical Formula 57]
[Chemical Formula 58]
[Chemical Formula 59]
[Chemical Formula 60]
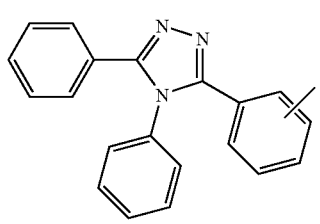
[Chemical Formula 61]
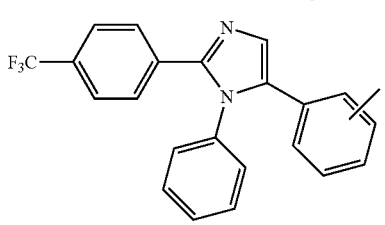
[Chemical Formula 62]
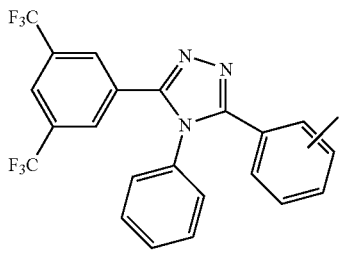
[Chemical Formula 63]
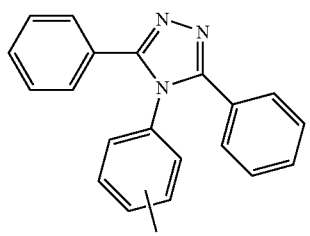
[Chemical Formula 64]
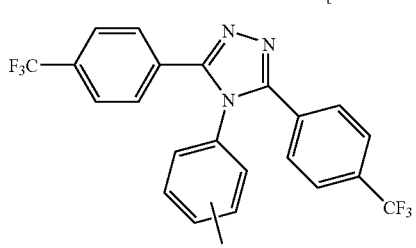

[Chemical Formula 65]

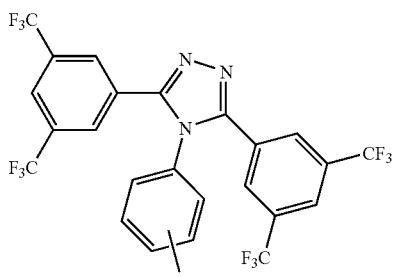

E in Chemical Formula 2 is selected from the group of hydrogen, a nitrile, a cyano, a nitro, an amide, a carbonyl, a substituted or unsubstituted alkyl, a substituted or unsubstituted fluoroalkyl, a substituted or unsubstituted cycloalkyl, a substituted or unsubstituted aryl, a substituted or unsubstituted heterocycle, and $SO_2R_9$, where $R_9$ is selected from the group of a nitrile, a cyano, a nitro, an amide, a carbonyl, a substituted or unsubstituted alkyl, a substituted or unsubstituted cycloalkyl, a substituted or unsubstituted aryl, and a substituted or unsubstituted heterocycle.

A compound according to an embodiment has an asymmetric structure where upper and lower substituents are different from each other with respect to the axis including $A_3$. This asymmetric structure may fortify the amorphous characteristic and suppress crystallization of the compound, and thereby improve the life-span characteristic when an organic photoelectric device using the same is driven. In addition, it may decrease the driving voltage of the organic photoelectric device and may provide an organic photoelectric device having excellent characteristics in terms of efficiency and thermal stability. In contrast, a symmetric compound may be easily crystallized, decreasing the life-span characteristic when an organic light emitting diode is driven.

In the compound represented by Chemical Formula 1 according to an embodiment, the $A_1$ and $A_5$ are different from each other, and $A_2$ and $A_4$ are different. In addition, $R_2$ and $R_4$ in a compound for an organic photoelectric device represented by Chemical Formula 2 may be different from each other. In an embodiment, the $R_2$ and $R_4$ are not simultaneously hydrogen. When the $R_2$ and $R_4$ are not the same, they can increase the amorphous characteristic and selectively impart hole injection/transfer capability and electron injection/transfer capability to the compound, which may make hole-electron combination in an emission layer more efficient.

In Chemical Formulae 1 and 2, $R_1$ to $R_5$, R', and R" are independently aryls, and it is preferable that the aryls are substituted or unsubstituted C6 to C40 aryls. When the aryls are unfused cyclic aryls such as phenyl, biphenyl, terphenyl, styrene, and so on, or fused polycyclic aryls such as naphthyl, anthracenyl, phenanthrenyl, pyrenyl, perylenyl, and so on, the compound may be useful for a material of an emission layer. When the aryls are an aryl such as anthracene, peryene, pyrene, stilbene, and so on, the compound may be particularly useful for a material of an emission layer.

In Chemical Formulae 1 and 2, it is more preferable that $R_1$ to $R_5$, R', and R" are independently an arylamine. The arylamine is preferably selected from the group of diphenyl amine, dinaphthyl amine, dibiphenyl amine, phenyl naphthyl amine, phenyl diphenyl amine, ditolyl amine, phenyl tolyl amine, carbazole, and triphenyl amine.

In Chemical Formulae 1 and 2, when $R_1$ to $R_5$, R', and R" are independently a substituted or unsubstituted heterocycle, the heterocycle is selected from the group of thiophene, furan, pyrrole, imidazolyl, thiazolyl, oxazolyl, oxadiazolyl, triazolyl, pyridinyl, pyridazine, quinolinyl, isoquinolinine, acridyl, imidazopyridinyl, and imidazopyrimidinyl. When the heterocycle is substituted imidazole or triazole, the substituent linked to nitrogen (N) of the imidazole or triazole is selected from the group of a substituted or unsubstituted alkyl such as a substituted or unsubstituted methyl, a substituted or unsubstituted ethyl, a substituted or unsubstituted propyl, a substituted or unsubstituted isopropyl, a substituted or unsubstituted butyl, a substituted or unsubstituted t-butyl, a substituted or unsubstituted pentyl, a substituted or unsubstituted hexyl, and a substituted or unsubstituted heptyl; a substituted or unsubstituted cycloalkyl such as a substituted or unsubstituted cyclopentyl, a substituted or unsubstituted cyclohexyl, and so on; a substituted or unsubstituted aryl such as a substituted or unsubstituted phenyl, a substituted or unsubstituted biphenyl, a substituted or unsubstituted naphthyl, and so on; and a substituted or unsubstituted heterocycle. The heterocycle is preferably a heteroaryl such as pyridyl, bipyridyl, quinolyl, isoquinolyl, and so on.

In Chemical Formulae 1 and 2, it is preferable that $R_1$ to $R_5$, R', and R" are functional groups having excellent electron injection characteristics or functional groups being capable of improving thermal stability. The functional groups can selectively endow the compounds with hole injection/transport capabilities and electron injection/transport capabilities, and thus enable efficient hole-electron combination in an emission layer.

For example, in Chemical Formulae 1 and 2, when one selected from $R_1$ to $R_5$, R', and R" includes a substituent selected from the group of an amine substituted alkyl, an amine substituted cycloalkyl, an amine substituted aryl, and an amine substituted heterocycle, the compound is useful for a material of a hole injection layer (HIL) and a hole transport layer (HTL). A preferable amine substituted heterocycle is an amine substituted heteroaryl.

In Chemical Formulae 1 and 2, when one selected from $R_1$ to $R_5$, R', and R" includes a substituent having excellent electron affinity selected from the group of a nitrile, a nitro, an amide, a carbonyl, and a heterocycle, the compound may be particularly useful for a material of an electron injection layer (EIL) or an electron transport layer (ETL). A preferable heterocycle is a heteroaryl.

In Chemical Formulae 1 and 2, when one selected from $R_1$ to $R_5$, R', and R" includes a substituent selected from the group of an amine substituted alkyl, an amine substituted cycloalkyl, an amine substituted aryl, and an amine substituted heterocycle, one selected from $R_1$ to $R_5$, R', and R" includes a substituent having excellent electron affinity selected from the group of a nitrile, a nitro, an amide, a carbonyl, and a heterocycle, the compound has both hole transport and electron transport capabilities. A preferable amine substituted heterocycle is an amine substituted heteroaryl, and a preferable heterocycle is a heteroaryl.

In Chemical Formulae 1 and 2, when E and R" of G independently include both a substituent selected from the group of an amine substituted alkyl, an amine substituted cycloalkyl, an amine substituted aryl, and an amine substituted heterocycle, and a substituent selected from the group of a nitrile, a nitro, an amide, a carbonyl, and a heterocycle, amorphous characteristics may be more improved, and hole and electron transport characteristics may be finely controlled.

In Chemical Formulae 1 and 2, when one selected from E and R" of G includes a substituent selected from the group of an amine substituted alkyl, an amine substituted cycloalkyl, an amine substituted aryl, and an amine substituted heterocycle, and the other of E and R" of G includes a nitrile, a nitro, an amide, a carbonyl, and a heterocycle, amorphous characteristics may be more improved, and hole and electron transport characteristics may be finely controlled. A preferable amine substituted heterocycle is an amine substituted heteroaryl, and a preferable heterocycle is a heteroaryl.

In Chemical Formula 1, L is preferably selected from the group of a substituted or unsubstituted C6 to C30 aryl and a substituted or unsubstituted C5 to C30 heteroaryl.

The various preferred substituents of the above-described compound represented by Chemical Formula 1 according to an embodiment may avoid changes in principal properties of the compound for an organic photoelectric device.

Examples of the compounds for an organic photoelectric device according to an embodiment include the compounds represented by the following Chemical Formulae 66 to 175.

[Chemical Formula 66]

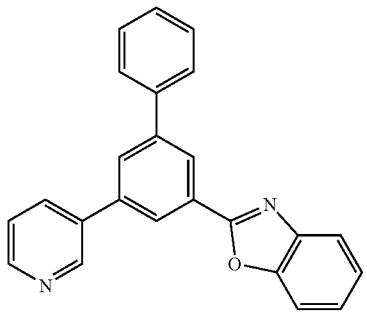

[Chemical Formula 67]

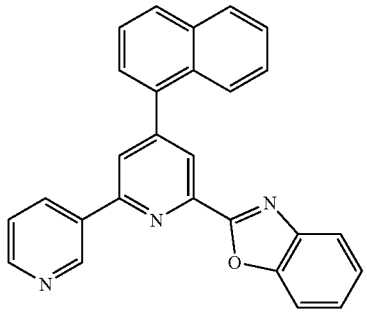

[Chemical Formula 68]

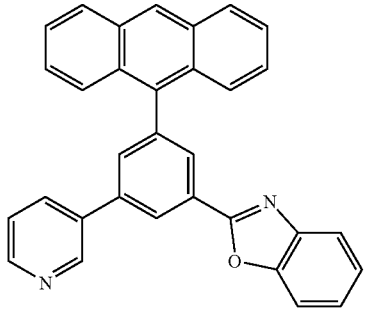

[Chemical Formula 69]

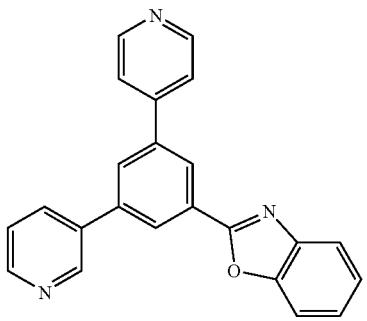

[Chemical Formula 70]

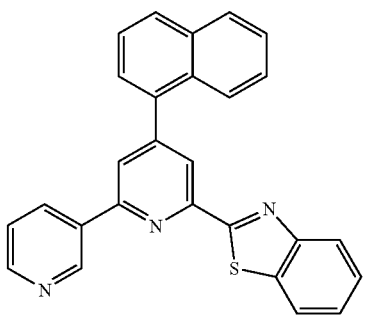

[Chemical Formula 71]

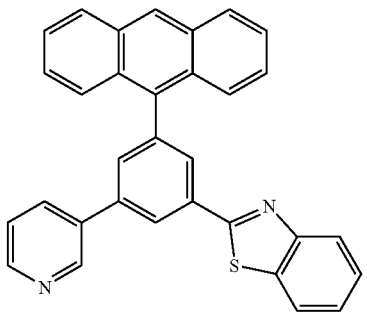

[Chemical Formula 72]

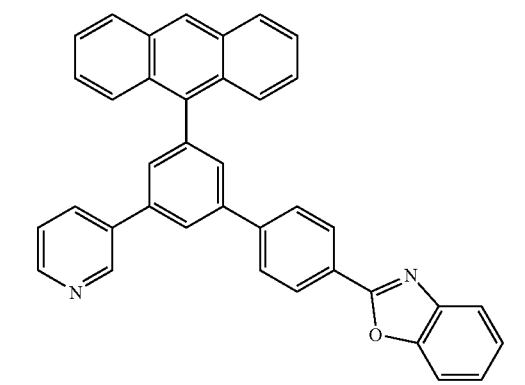

[Chemical Formula 73]
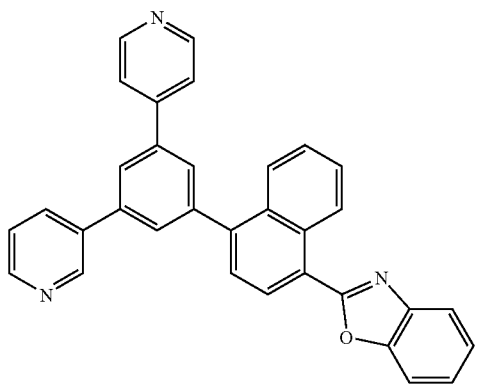
[Chemical Formula 74]
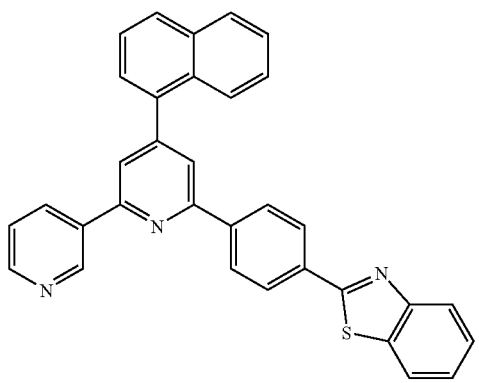
[Chemical Formula 75]
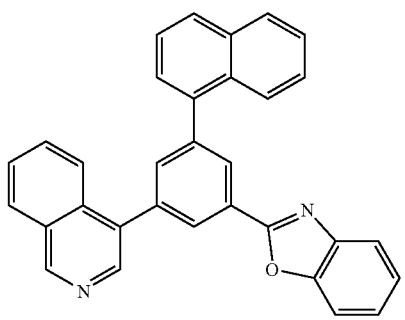
[Chemical Formula 76]
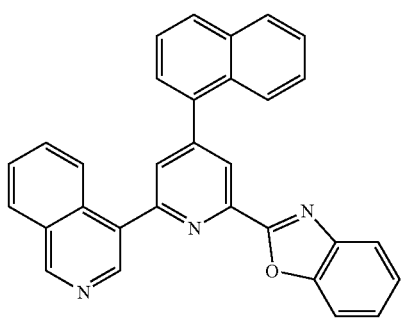
[Chemical Formula 77]
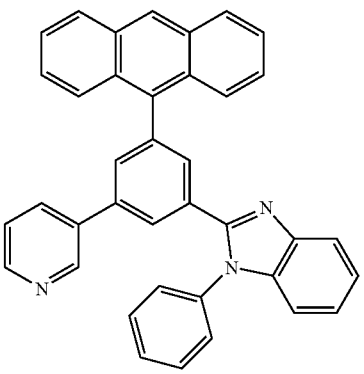
[Chemical Formula 78]
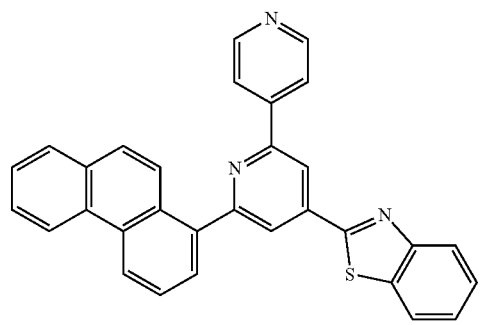
[Chemical Formula 79]
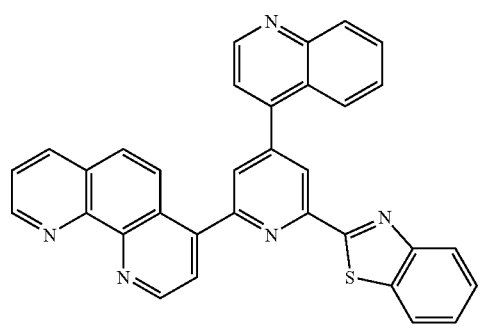
[Chemical Formula 80]
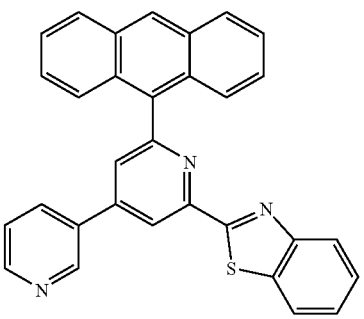

[Chemical Formula 81]
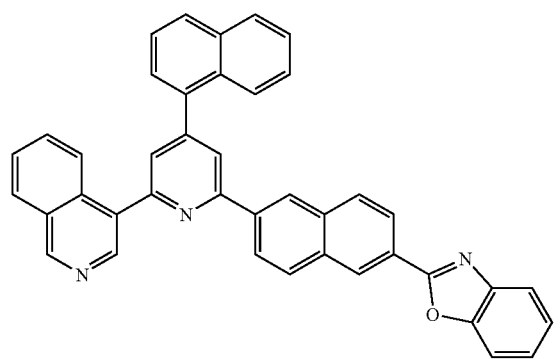
[Chemical Formula 82]
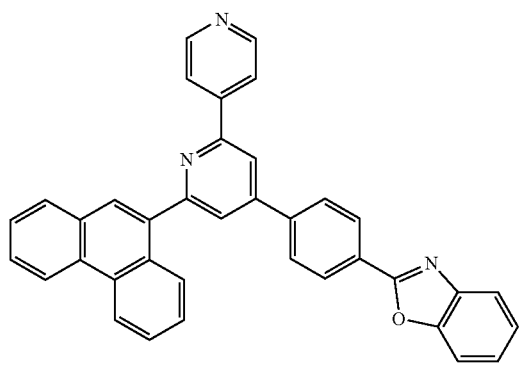
[Chemical Formula 83]
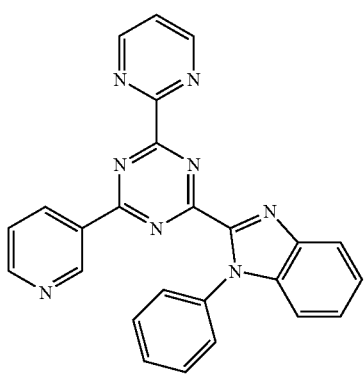
[Chemical Formula 84]
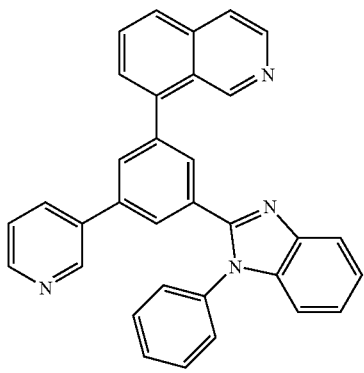
[Chemical Formula 85]
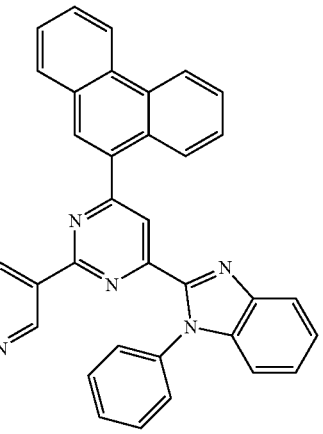
[Chemical Formula 86]
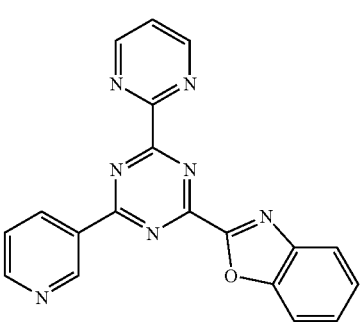
[Chemical Formula 87]
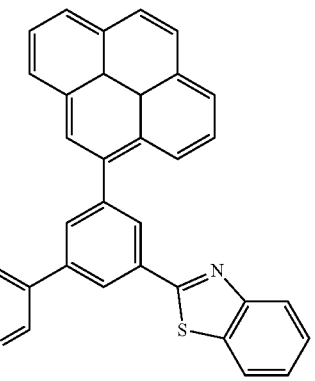
[Chemical Formula 88]
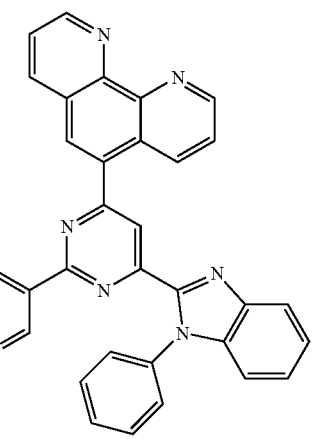

[Chemical Formula 89]

[Chemical Formula 90]

[Chemical Formula 91]

[Chemical Formula 92]

[Chemical Formula 93]

[Chemical Formula 94]

[Chemical Formula 95]

[Chemical Formula 96]

[Chemical Formula 97]
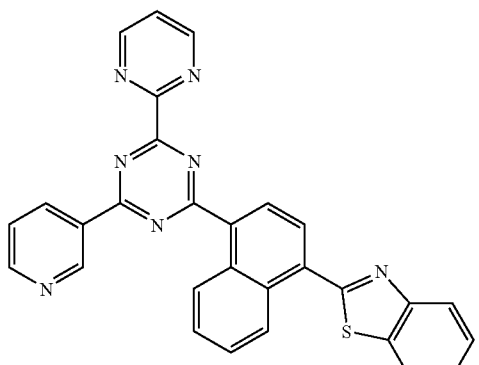
[Chemical Formula 98]
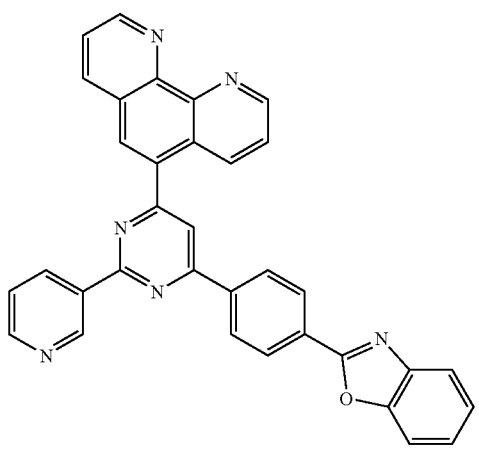
[Chemical Formula 99]
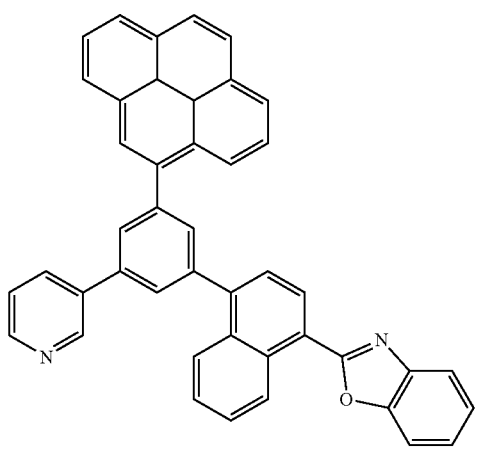
[Chemical Formula 100]
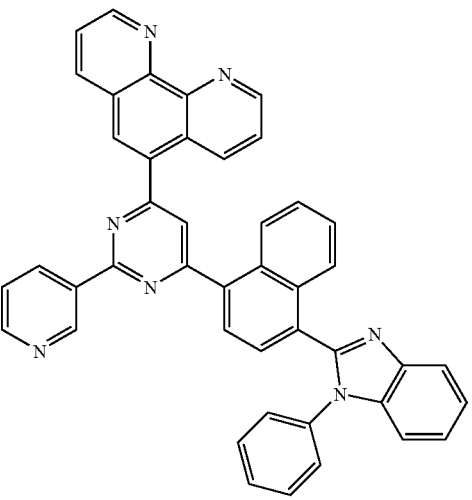
[Chemical Formula 101]
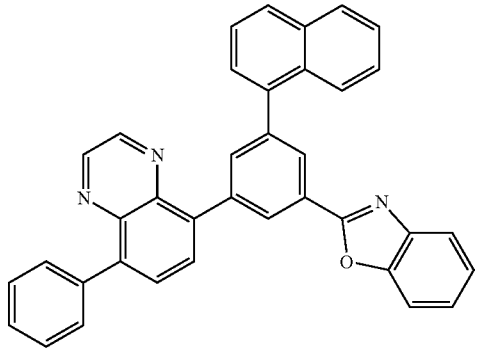
[Chemical Formula 102]
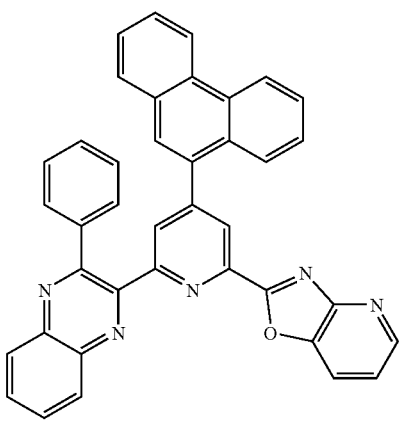

[Chemical Formula 103]
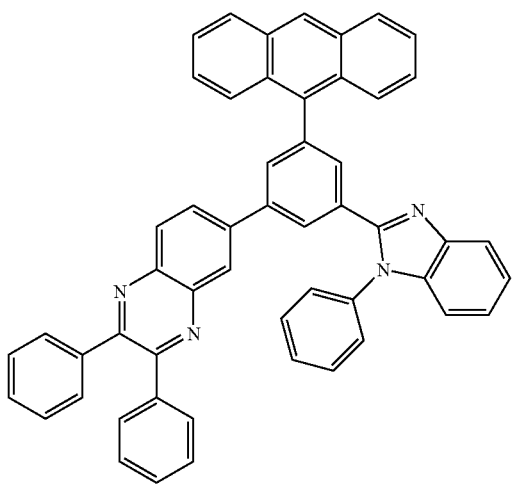
[Chemical Formula 104]
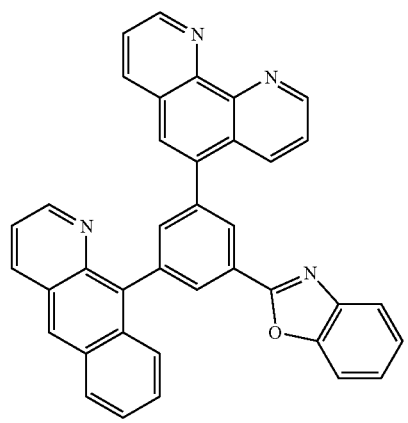
[Chemical Formula 105]
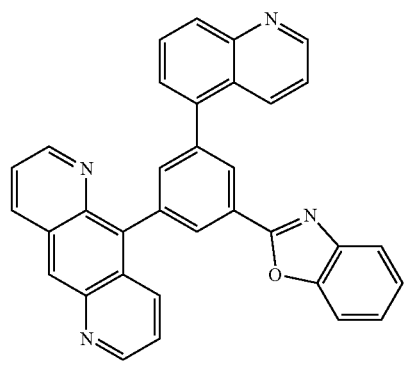
[Chemical Formula 106]
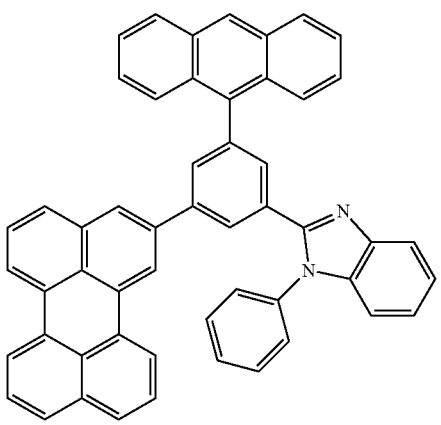
[Chemical Formula 107]
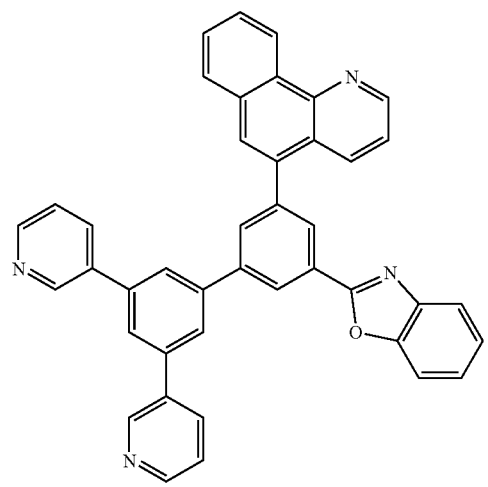
[Chemical Formula 108]
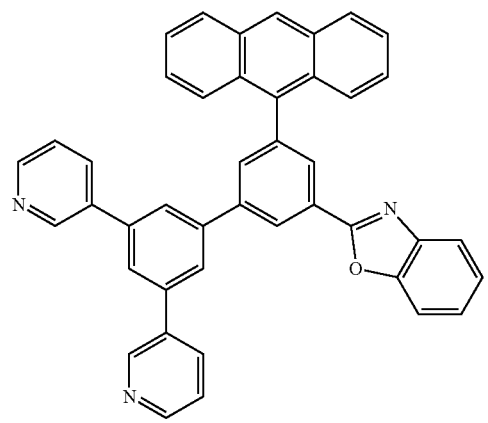

[Chemical Formula 109]
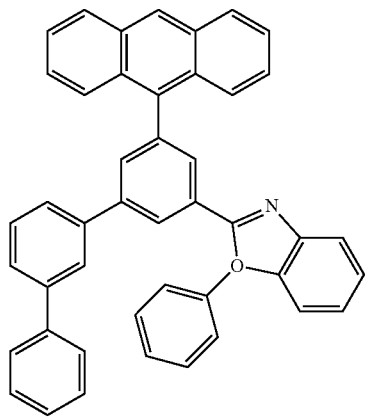
[Chemical Formula 110]
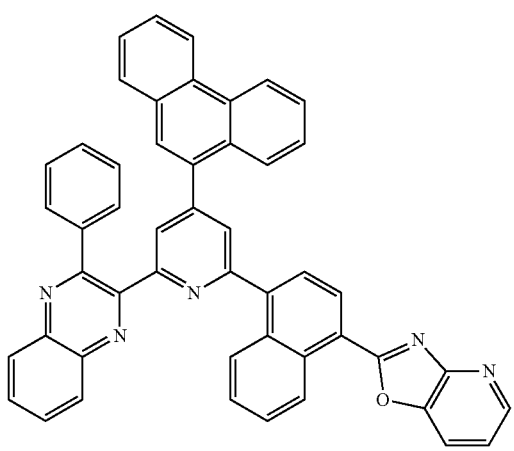
[Chemical Formula 111]
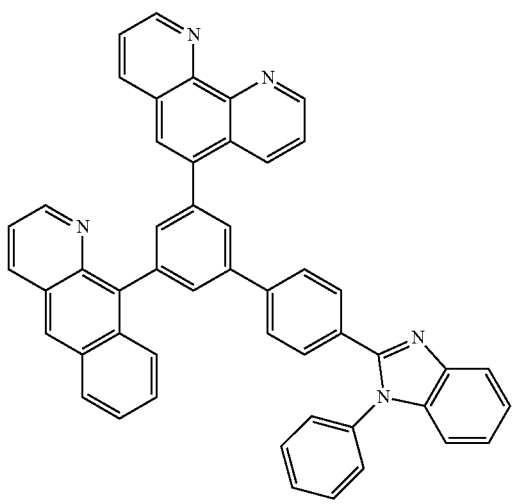
[Chemical Formula 112]
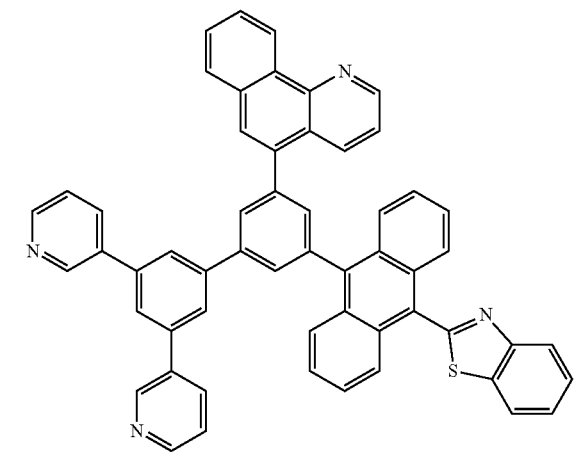
[Chemical Formula 113]
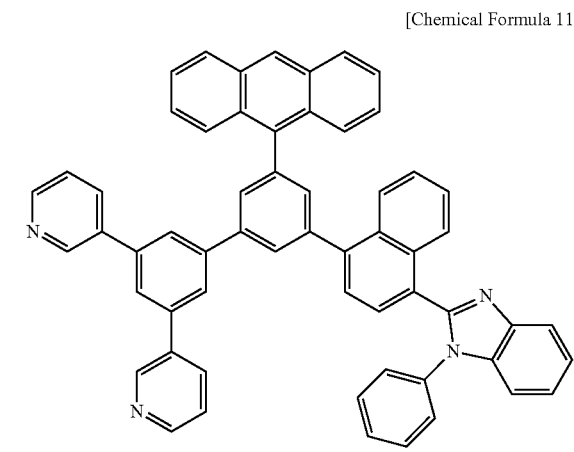
[Chemical Formula 114]
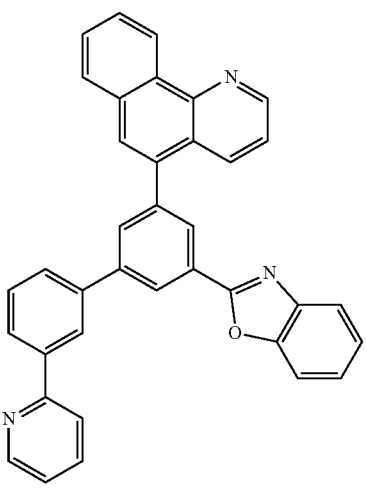

[Chemical Formula 115]
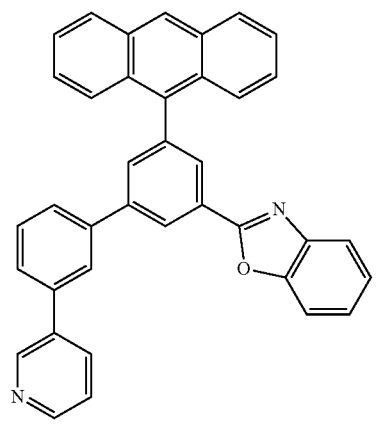
[Chemical Formula 116]
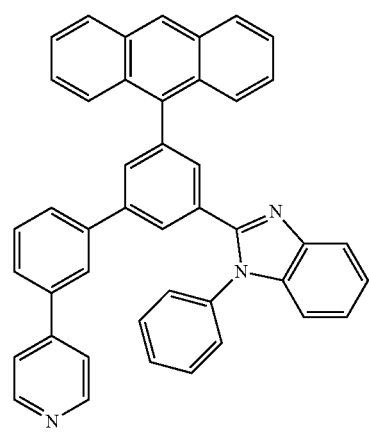
[Chemical Formula 117]
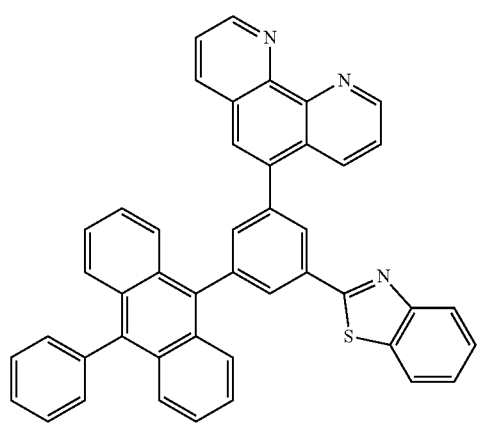
[Chemical Formula 118]
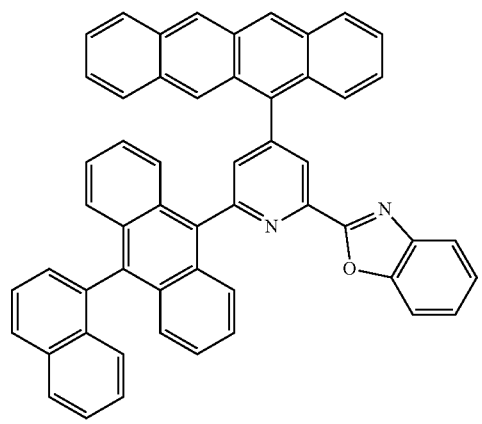
[Chemical Formula 119]
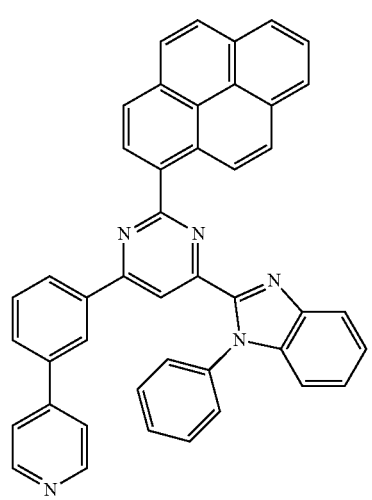
[Chemical Formula 120]
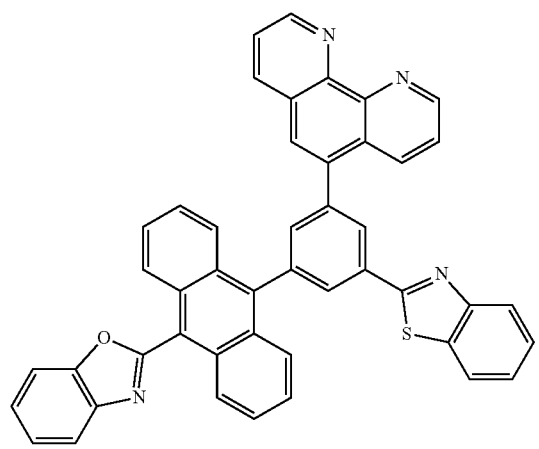

[Chemical Formula 121]
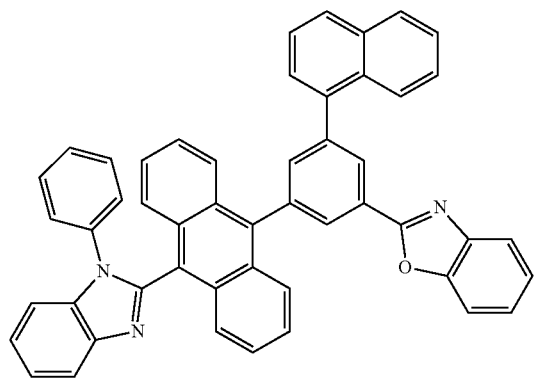
[Chemical Formula 122]
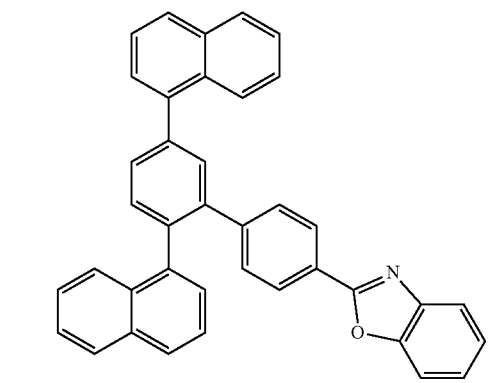
[Chemical Formula 123]
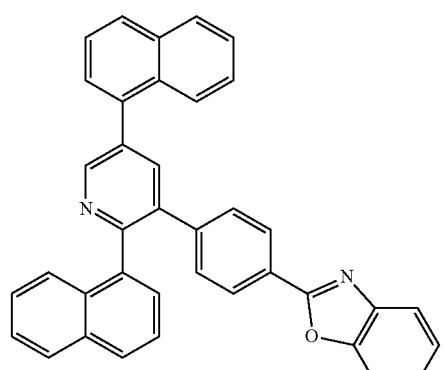
[Chemical Formula 124]
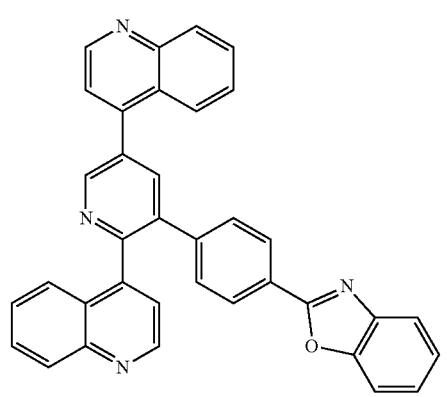
[Chemical Formula 125]
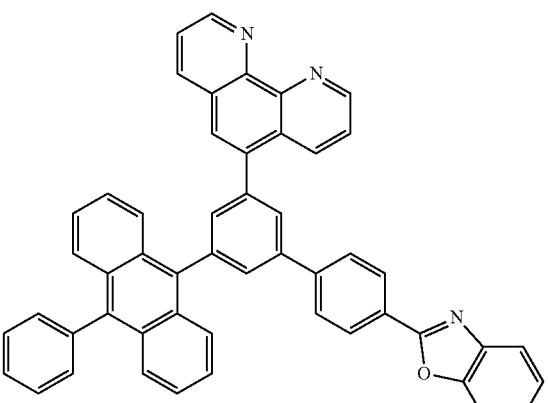
[Chemical Formula 126]
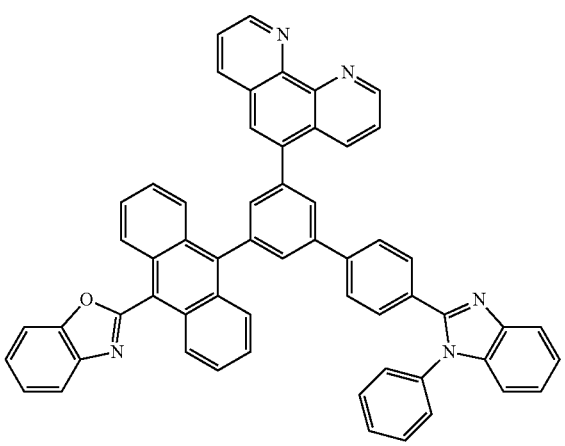
[Chemical Formula 127]
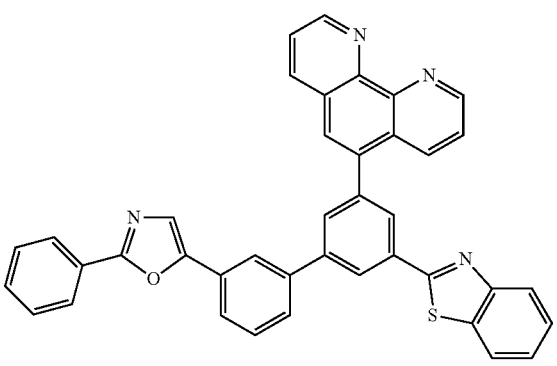
[Chemical Formula 128]
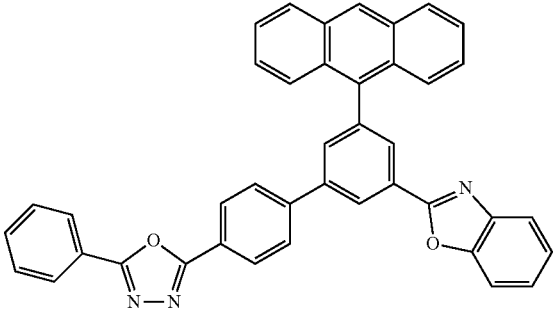

[Chemical Formula 129]
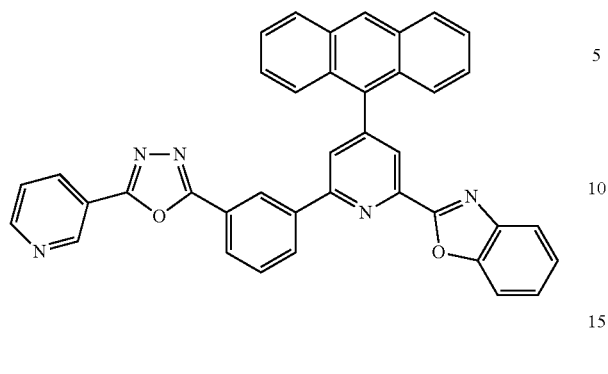
[Chemical Formula 130]
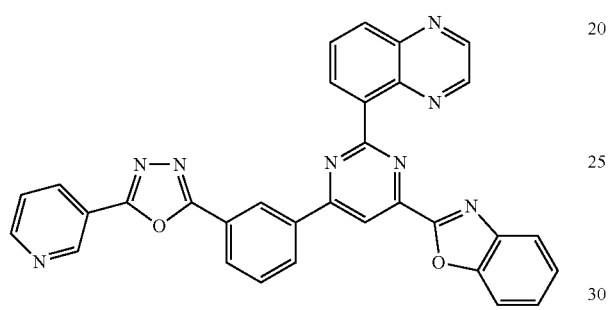
[Chemical Formula 131]
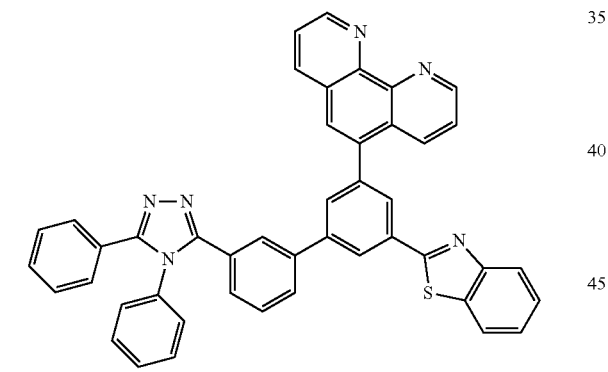
[Chemical Formula 132]
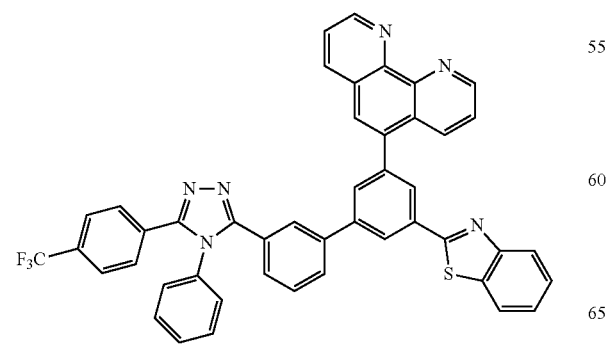
[Chemical Formula 133]
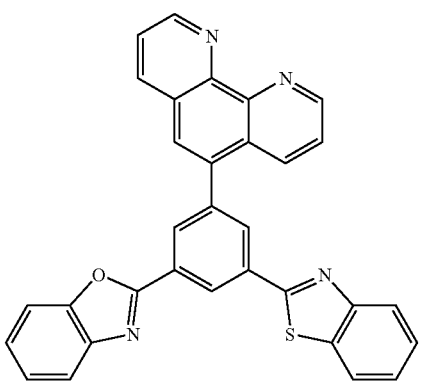
[Chemical Formula 134]
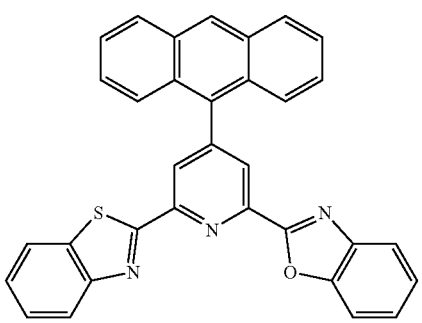
[Chemical Formula 135]
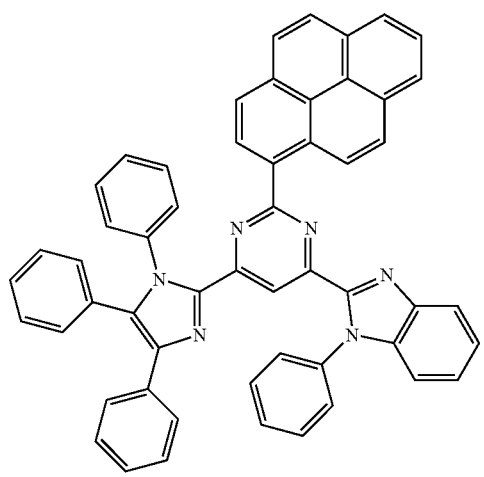

[Chemical Formula 136]
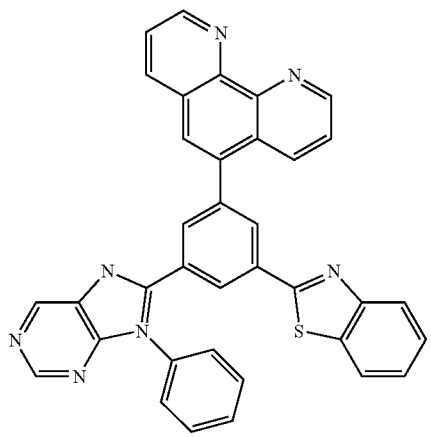
[Chemical Formula 137]
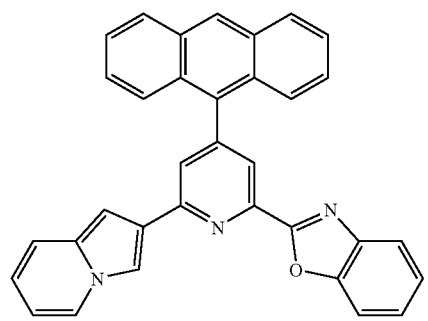
[Chemical Formula 138]
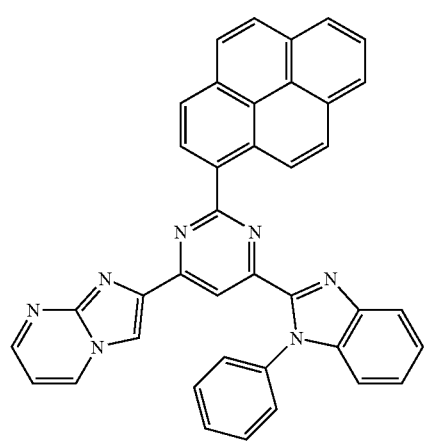
[Chemical Formula 139]
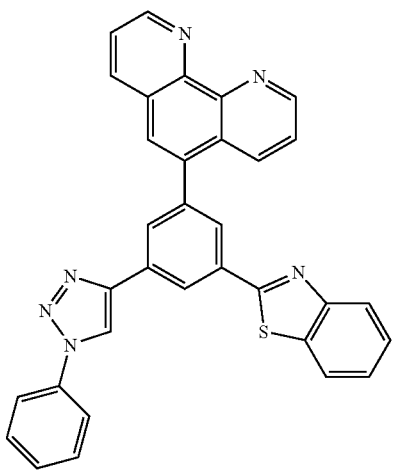
[Chemical Formula 140]
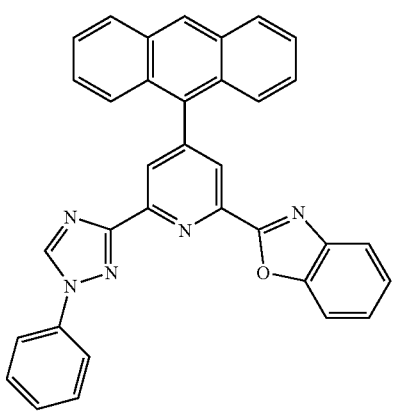
[Chemical Formula 141]
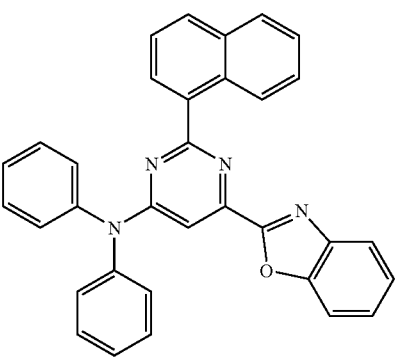

[Chemical Formula 142]
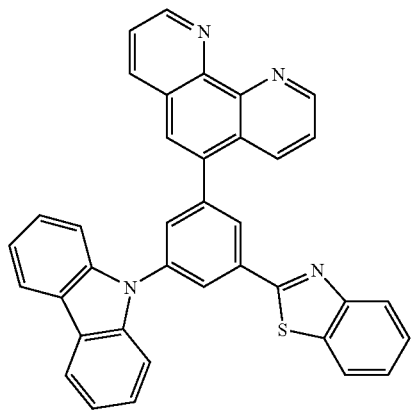
[Chemical Formula 143]
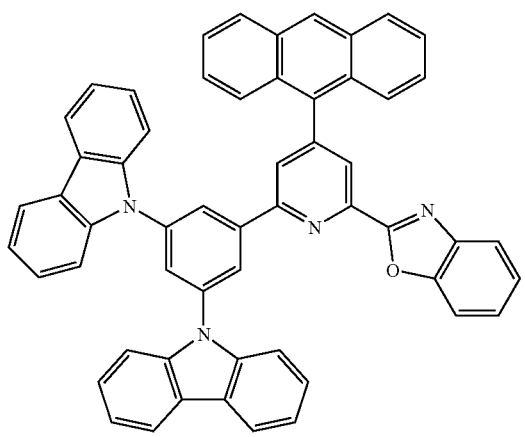
[Chemical Formula 144]
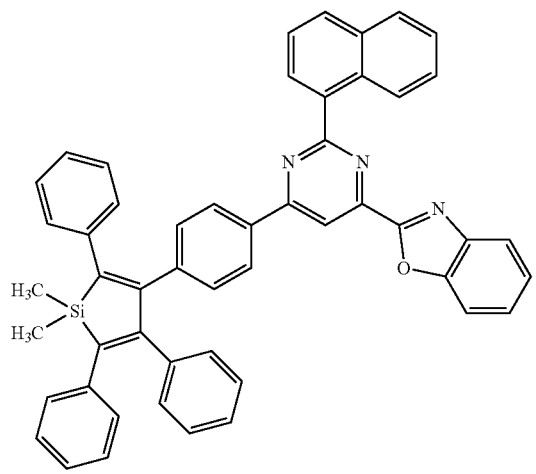
[Chemical Formula 145]
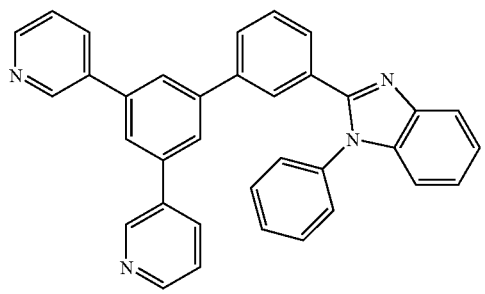
[Chemical Formula 146]
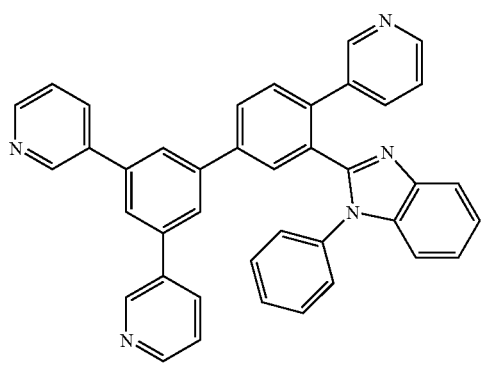
[Chemical Formula 147]
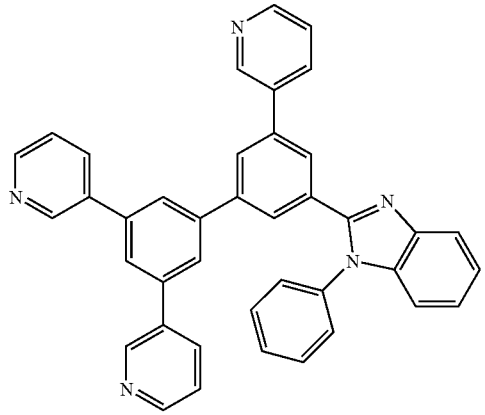
[Chemical Formula 148]
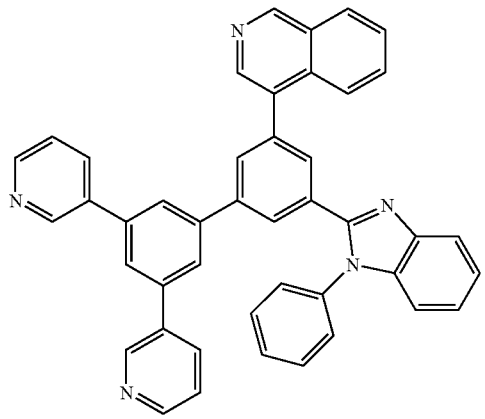

[Chemical Formula 149]
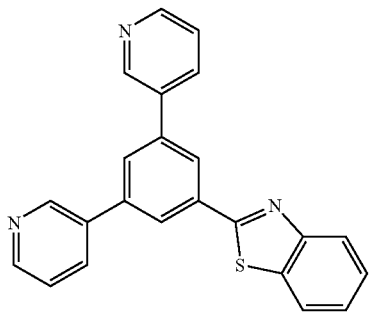
[Chemical Formula 150]
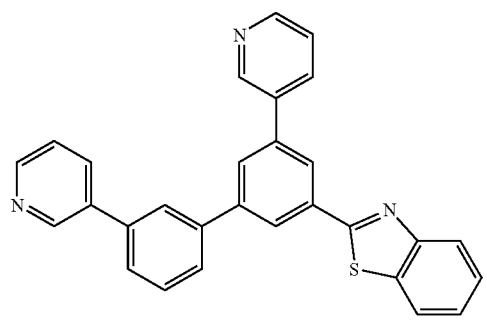
[Chemical Formula 151]
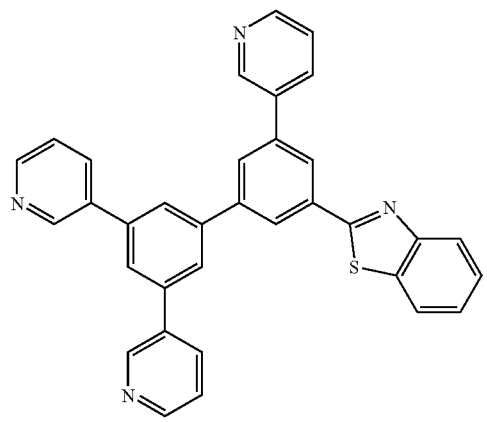
[Chemical Formula 152]
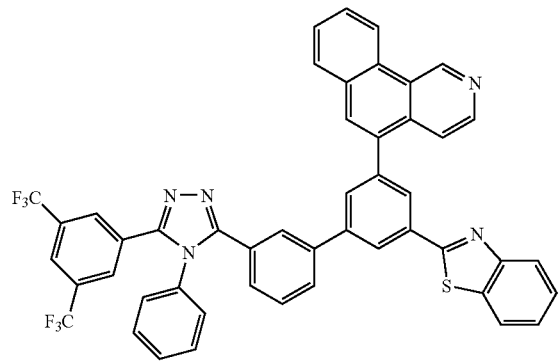
[Chemical Formula 153]
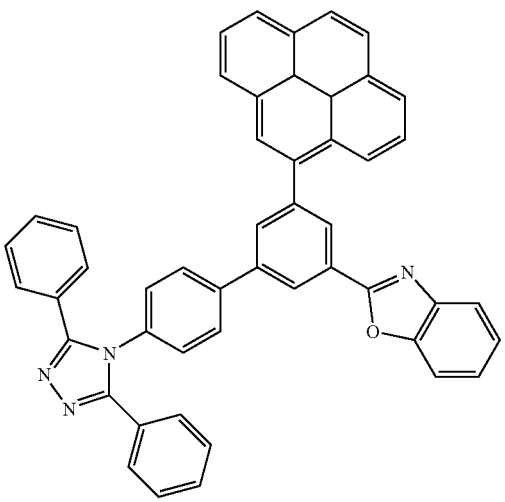
[Chemical Formula 154]
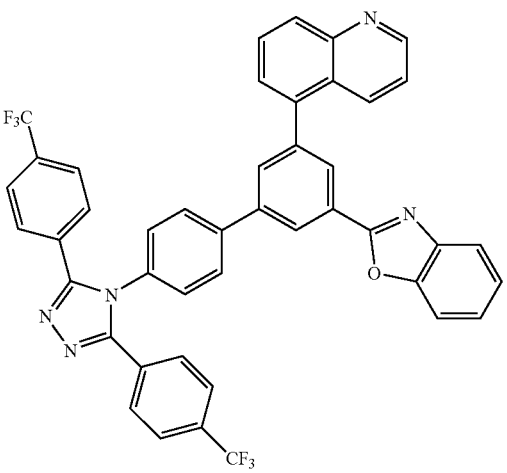
[Chemical Formula 155]
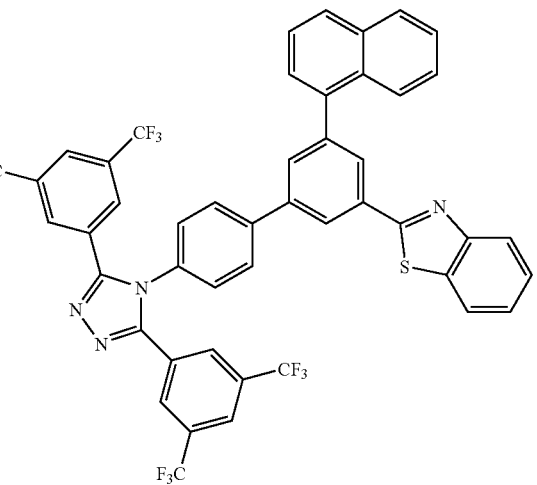

[Chemical Formula 156]
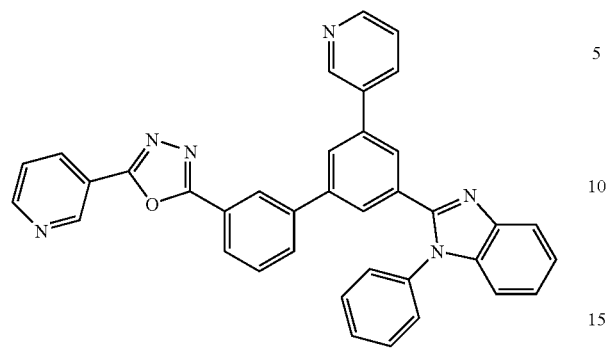
[Chemical Formula 160]
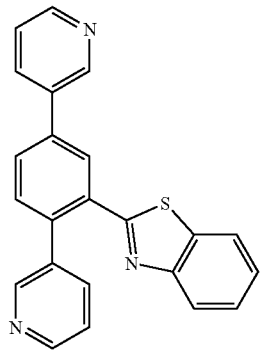
[Chemical Formula 157]
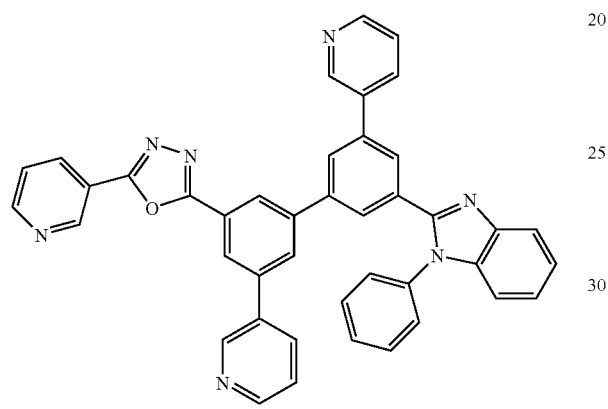
[Chemical Formula 161]
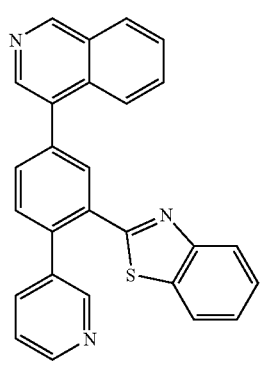
[Chemical Formula 158]
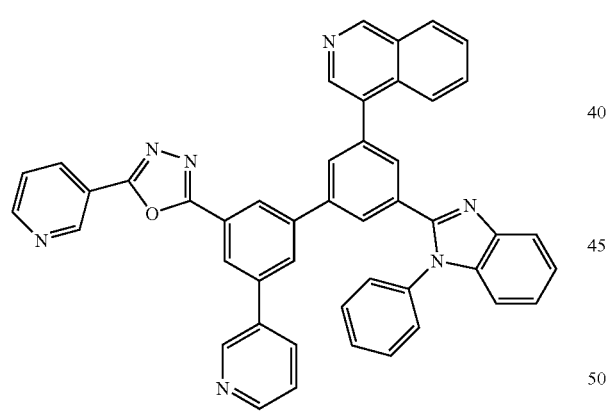
[Chemical Formula 162]
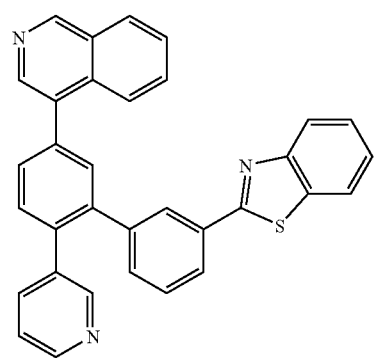
[Chemical Formula 159]
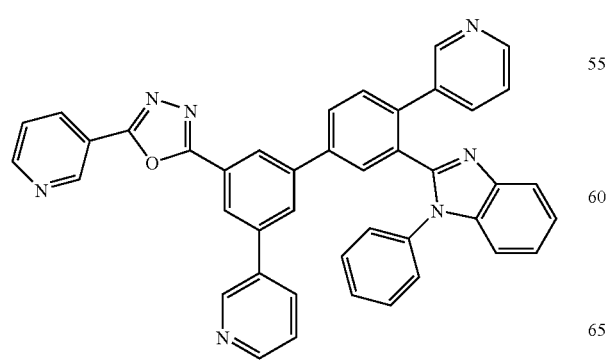
[Chemical Formula 163]
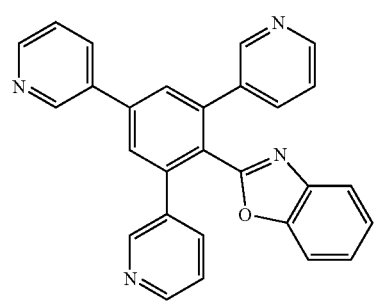

[Chemical Formula 164]
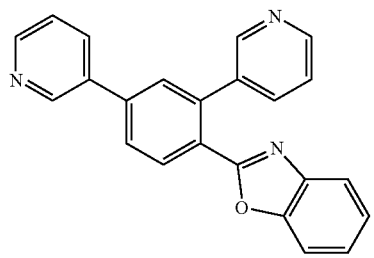
[Chemical Formula 165]
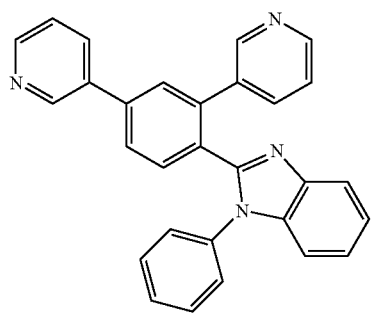
[Chemical Formula 166]
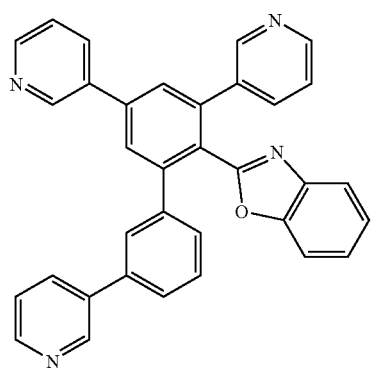
[Chemical Formula 167]
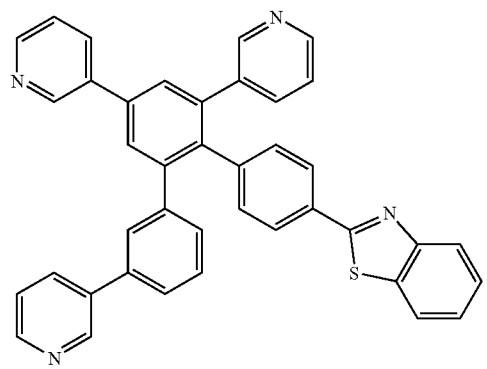
[Chemical Formula 168]
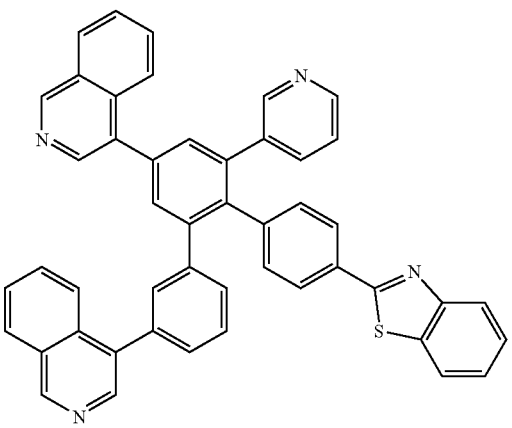
[Chemical Formula 169]
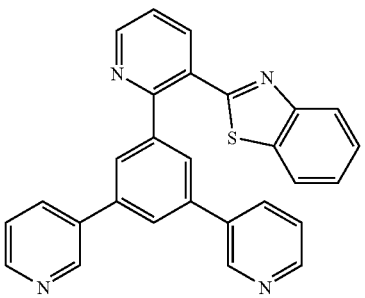
[Chemical Formula 170]
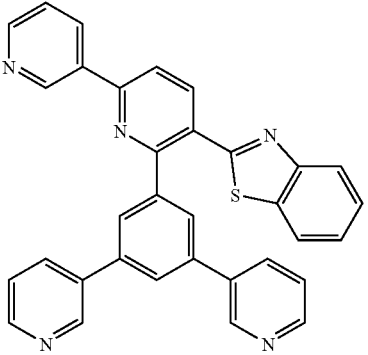
[Chemical Formula 171]
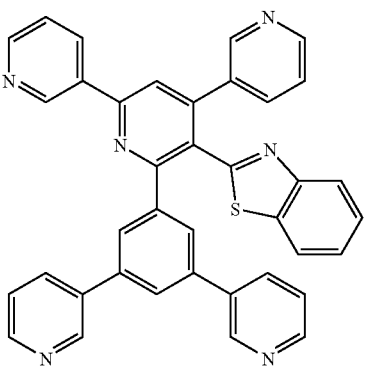

[Chemical Formula 172]

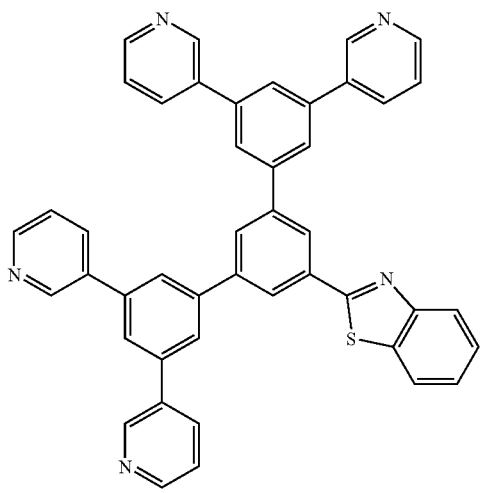

[Chemical Formula 175]

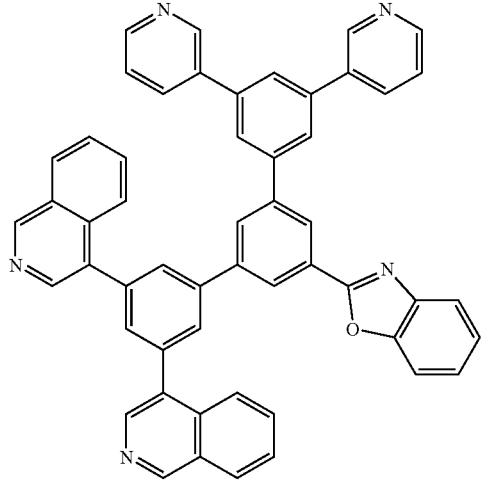

[Chemical Formula 173]

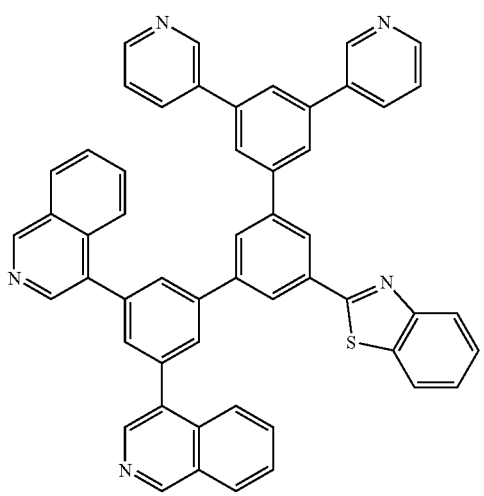

[Chemical Formula 174]

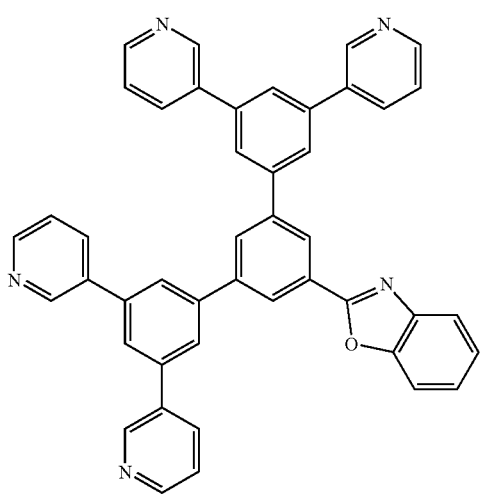

A compound for an organic photoelectric device according to an embodiment may play a role of hole injection, hole transport, light emitting, or electron injection and/or transport. The compound may be used as a light emitting host with a dopant. According to an embodiment, a compound for an organic photoelectric device may improve thermal stability and decrease driving voltage for improving life-span and efficiency characteristics of an organic photoelectric device when included in an organic thin layer.

A compound for an organic photoelectric device according to an embodiment may be used for a host material or a charge transfer material. Herein, the organic photoelectric device may include an organic light emitting diode, an organic solar cell, an organic transistor, an organic memory device, and the like.

For an organic solar cell, a compound according to an embodiment may be included in an electrode or an electrode buffer layer, and may thereby improve quantum efficiency. For an organic transistor, a compound according to an embodiment may be used as an electrode material in a gate, a source-drain electrode, and the like.

Hereinafter, an organic light emitting diode is described in more detail. An embodiment provides an organic photoelectric device including the compound for an organic photoelectric device in an organic thin layer, or in at least one layer among a plurality of organic thin layers. The organic photoelectric device may include an anode, a cathode, and at least one organic thin layer disposed between the anode and cathode.

An organic light emitting diode according to an embodiment may include a compound having various energy band gaps, for various conditions required for a hole injection layer (HIL), a hole transport layer (HTL), an emission layer, an electron injection layer (EIL), an electron transport layer (ETL), and the like. Accordingly, the organic light emitting diode according to an embodiment may realize a low driving voltage and high luminous efficiency.

The organic thin layer may be used as one or more of an emission layer, an electron transport layer (ETL), an electron injection layer (EIL), a hole transport layer (HTL), a hole injection layer (HIL), and a hole blocking layer, at least one layer of which may include a compound for an organic photoelectric device according to an embodiment. In an embodiment, at least one of the organic thin layers may include the compound for an organic photoelectric device and a reducing dopant. The reducing dopant may include at least one of an alkaline metal, an alkaline earth metal, a rare earth element metal, an oxide of an alkaline metal, a halide of an alkaline metal, an organic complex of an alkaline metal, an oxide of an alkaline earth metal, a halide of an alkaline earth metal, an organic complex of an alkaline earth metal, an oxide of an alkaline earth metal, a halide of an alkaline earth metal, an organic complex of an alkaline earth metal, an oxide of a rare earth element metal, a halide of a rare earth element metal, and an organic complex of a rare earth element metal.

FIGS. 1 to 5 illustrate cross-sectional views showing organic photoelectric devices including the organic compounds according to various embodiments.

Referring to FIGS. 1 to 5, the organic photoelectric devices 100, 200, 300, 400, and 500 according to embodiments may include at least one organic thin layer 105 interposed between an anode 120 and a cathode 110.

The anode 120 may include an anode material having a large work function to help hole injection into an organic thin layer. The anode material may include, e.g., a metal such as nickel, platinum, vanadium, chromium, copper, zinc, and gold, or alloys thereof; a metal oxide such as zinc oxide, indium oxide, indium tin oxide (ITO), and indium zinc oxide (IZO); a combined metal and oxide such as ZnO:Al or $SnO_2$:Sb; or a conductive polymer such as poly(3-methylthiophene), poly[3,4-(ethylene-1,2-dioxy)thiophene] (PEDT), polypyrrole, and polyaniline.

The cathode 110 may include a cathode material having a small work function to help electron injection into an organic thin layer. The cathode material may include, e.g., a metal such as magnesium, calcium, sodium, potassium, titanium, indium, yttrium, lithium, gadolinium, aluminum, silver, tin, and lead, or alloys thereof; or a multi-layered material such as LiF/Al, Liq/Al, $LiO_2$/Al, LiF/Ca, LiF/Al, and $BaF_2$/Ca.

In an embodiment illustrated in FIG. 1, the organic photoelectric device 100 may have an organic thin layer 105 including only an emission layer 130.

Figure 2:
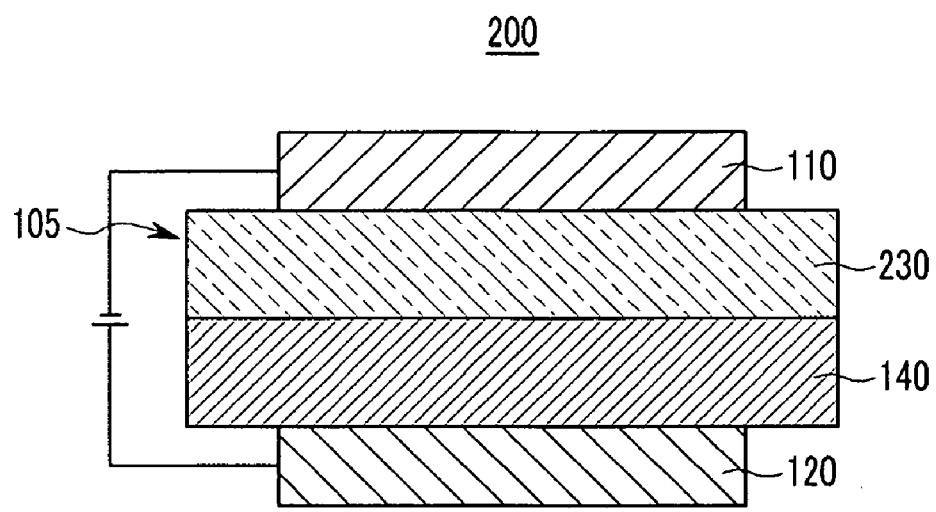

In an embodiment illustrated in FIG. 2, a double-layered organic photoelectric device 200 may have an organic thin layer 105 including an emission layer 230 including an electron transport layer (ETL), and a hole transport layer (HTL) 140. The emission layer 130 may also function as an electron transport layer (ETL), and the hole transport layer (HTL) 140 layer may have an excellent binding property with a transparent electrode such as ITO or an excellent hole transporting property.

Figure 3:
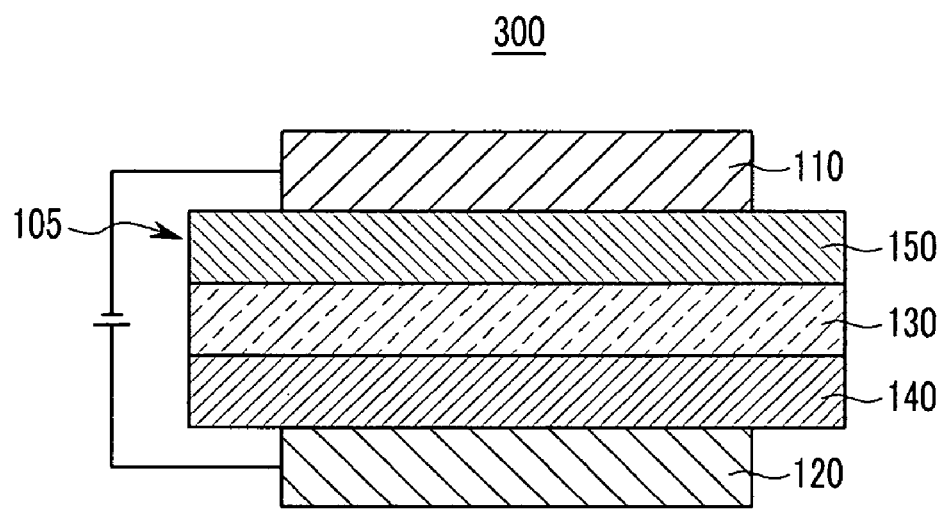

In an embodiment illustrated in FIG. 3, a three-layered organic photoelectric device 300 may have an organic thin layer 105 including an electron transport layer (ETL) 150, an emission layer 130, and a hole transport layer (HTL) 140. The emission layer 130 may be independently formed, and layers having an excellent electron transporting property or an excellent hole transporting property may be separately stacked.

Figure 4:
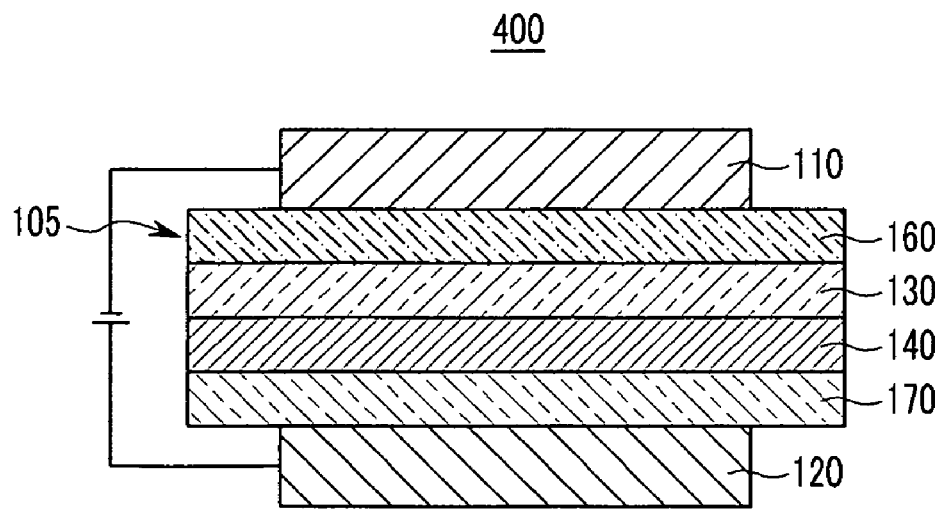

In an embodiment illustrated in FIG. 4, a four-layered organic photoelectric device 400 may have an organic thin layer 105 including an electron injection layer (EIL) 160, an emission layer 130, a hole transport layer (HTL) 140, and a hole injection layer (HIL) 170 for binding with the cathode of ITO.

Figure 5:
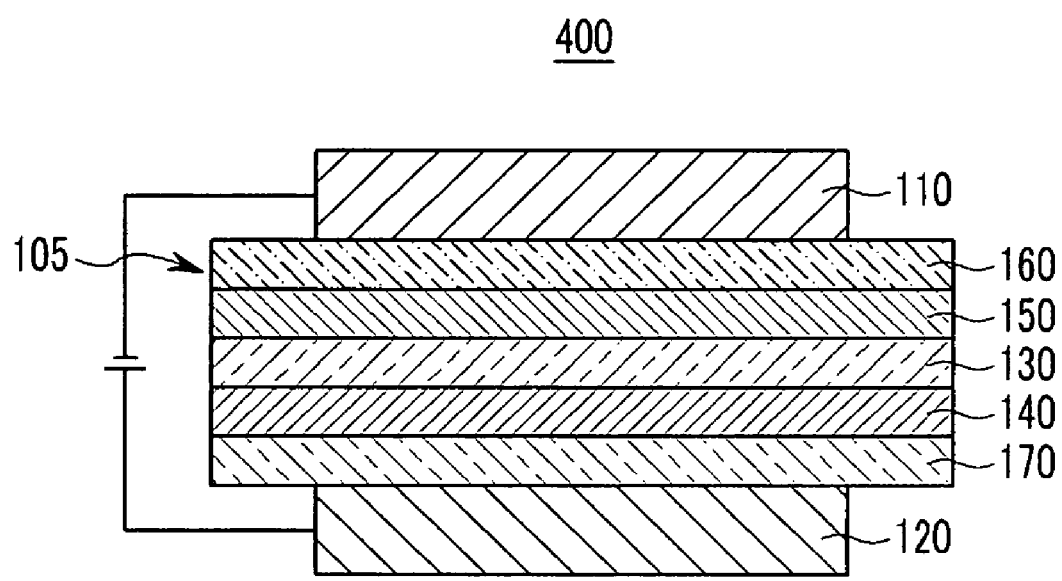
Figure 6:
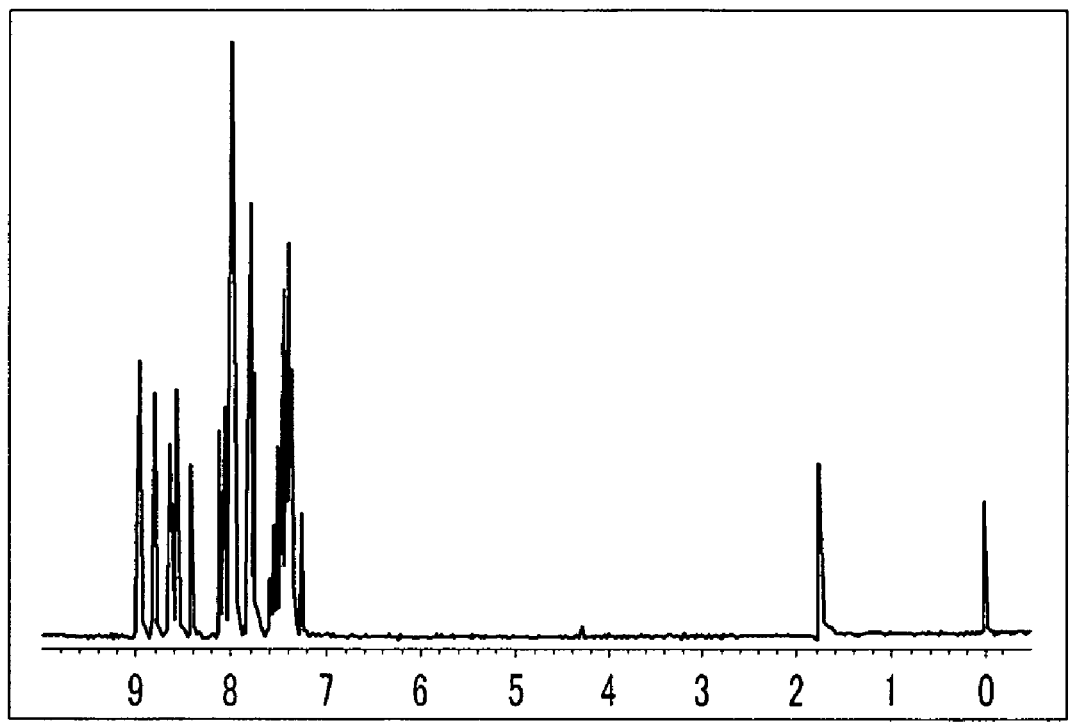
FIG. 6 illustrates a $^1H$ NMR spectrum of the compound according to Example 1 according to an embodiment.
Figure 7:
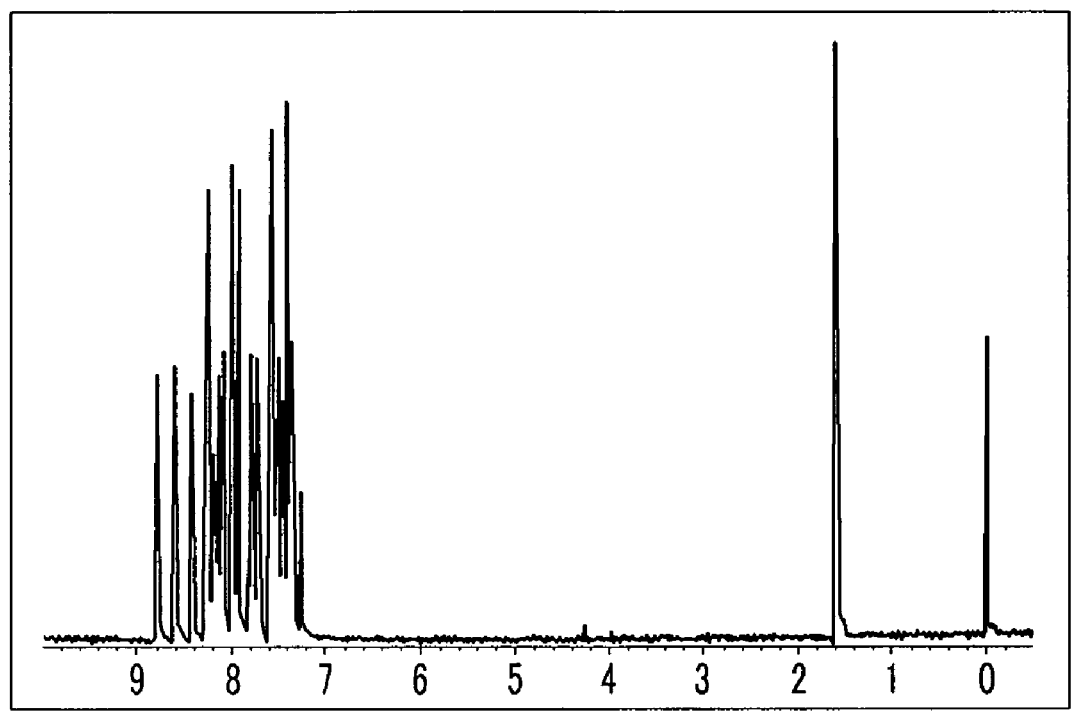
FIG. 7 illustrates a $^1H$ NMR spectrum of the compound according to Example 2 according to an embodiment.
Figure 8:
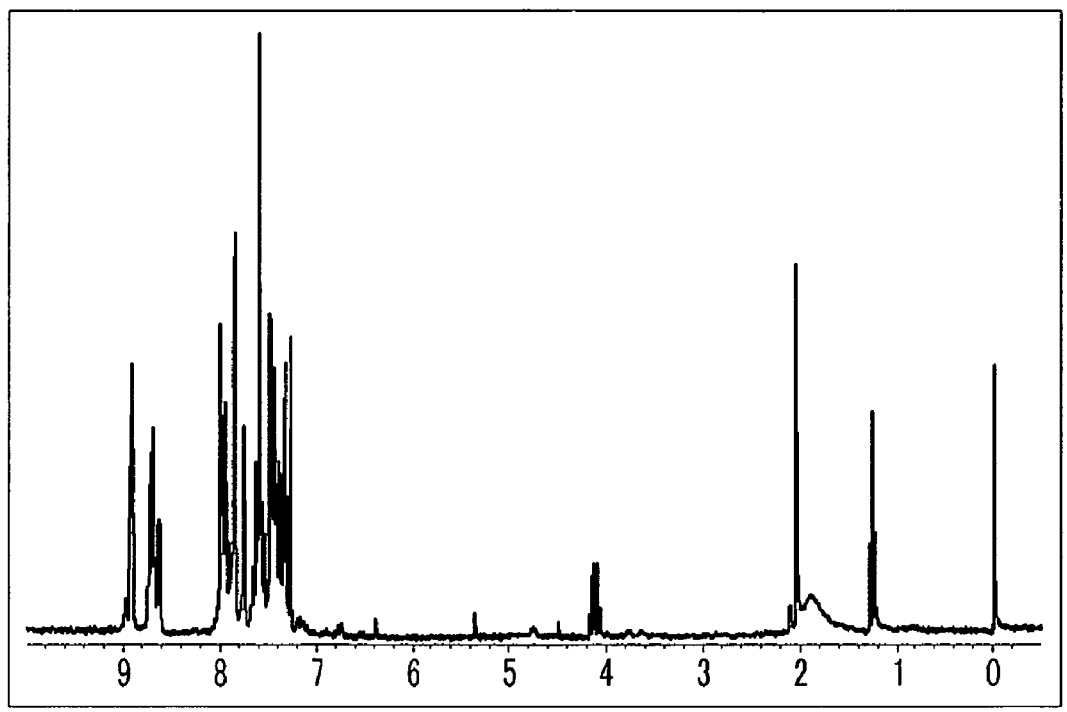
FIG. 8 illustrates a $^1H$ NMR spectrum of the compound according to Example 3 according to an embodiment.
Figure 9:
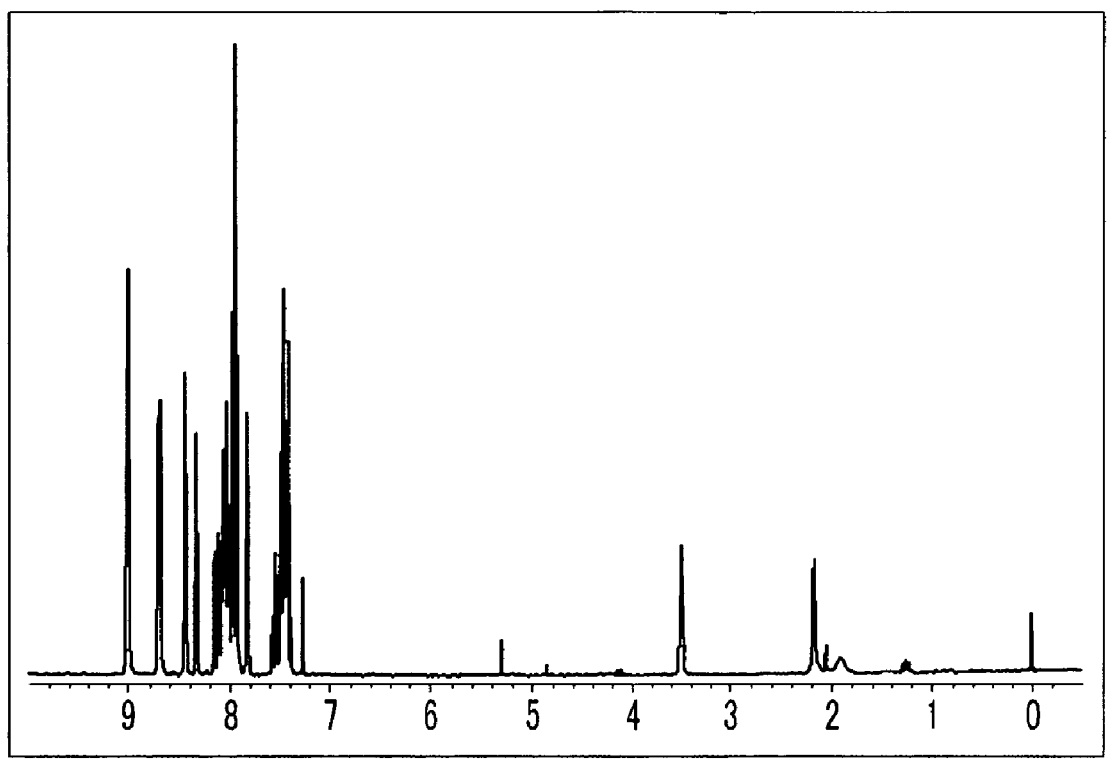
FIG. 9 illustrates a $^1H$ NMR spectrum of the compound according to Example 4 according to an embodiment.
Figure 10:
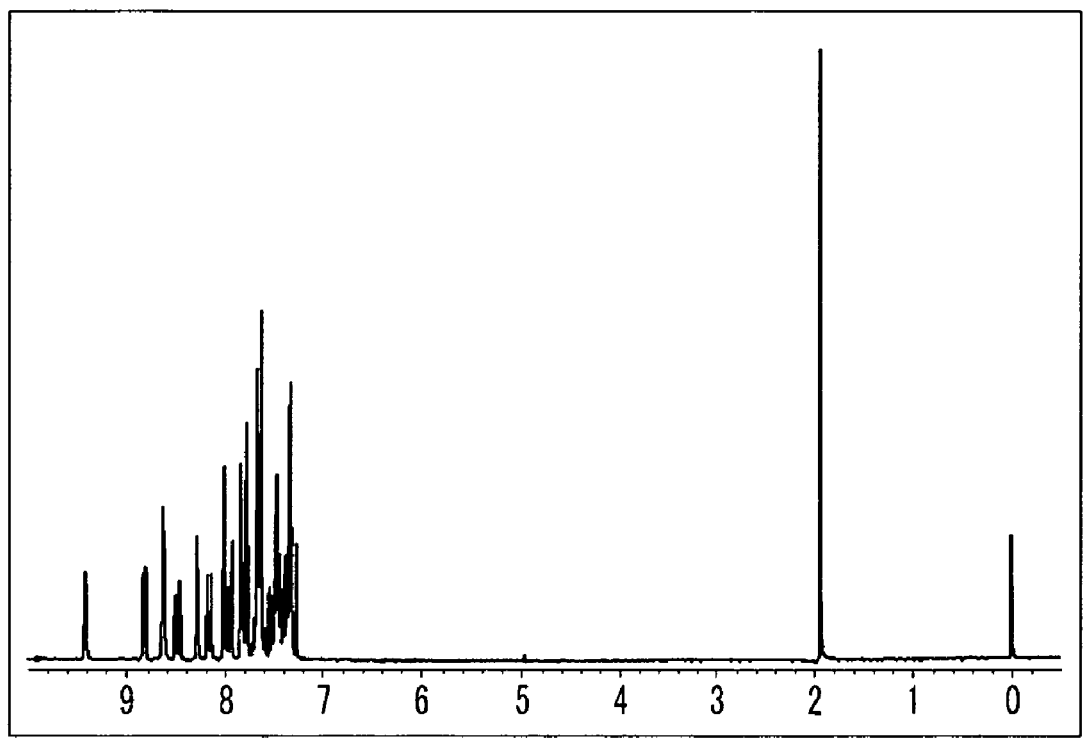
FIG. 10 illustrates a $^1H$ NMR spectrum of the compound according to Example 5 according to an embodiment.
Figure 11:
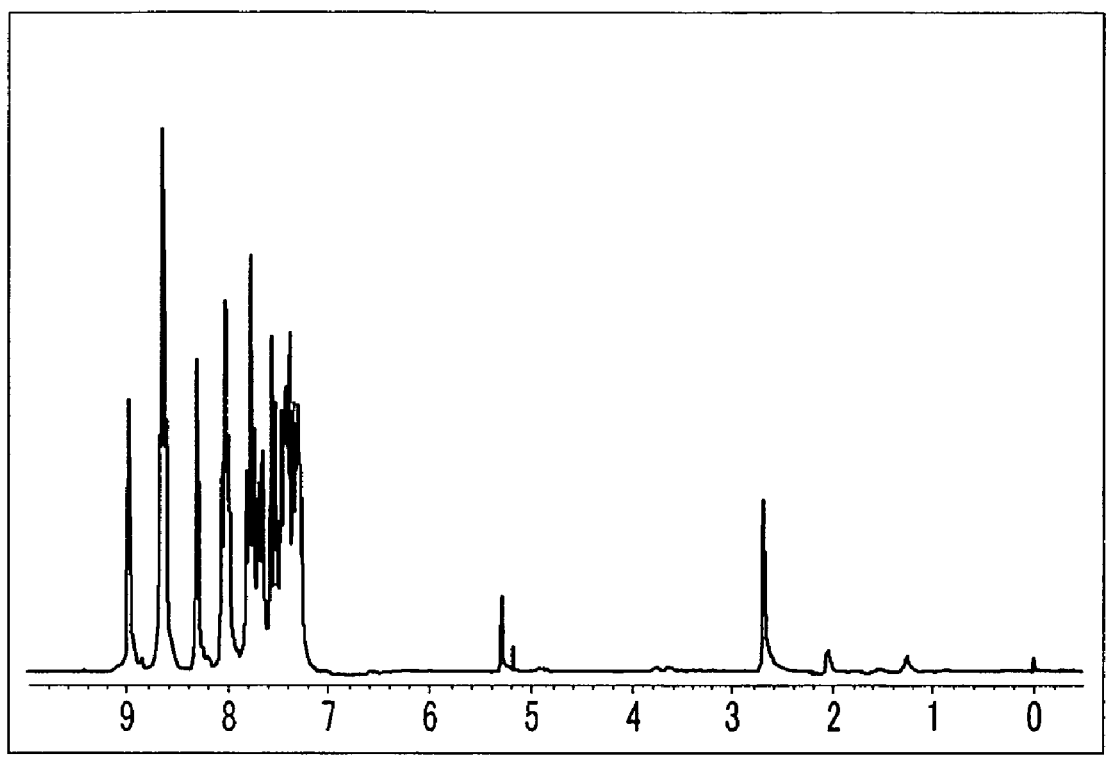
FIG. 11 illustrates a $^1H$ NMR spectrum of the compound according to Example 6 according to an embodiment.
Figure 12:
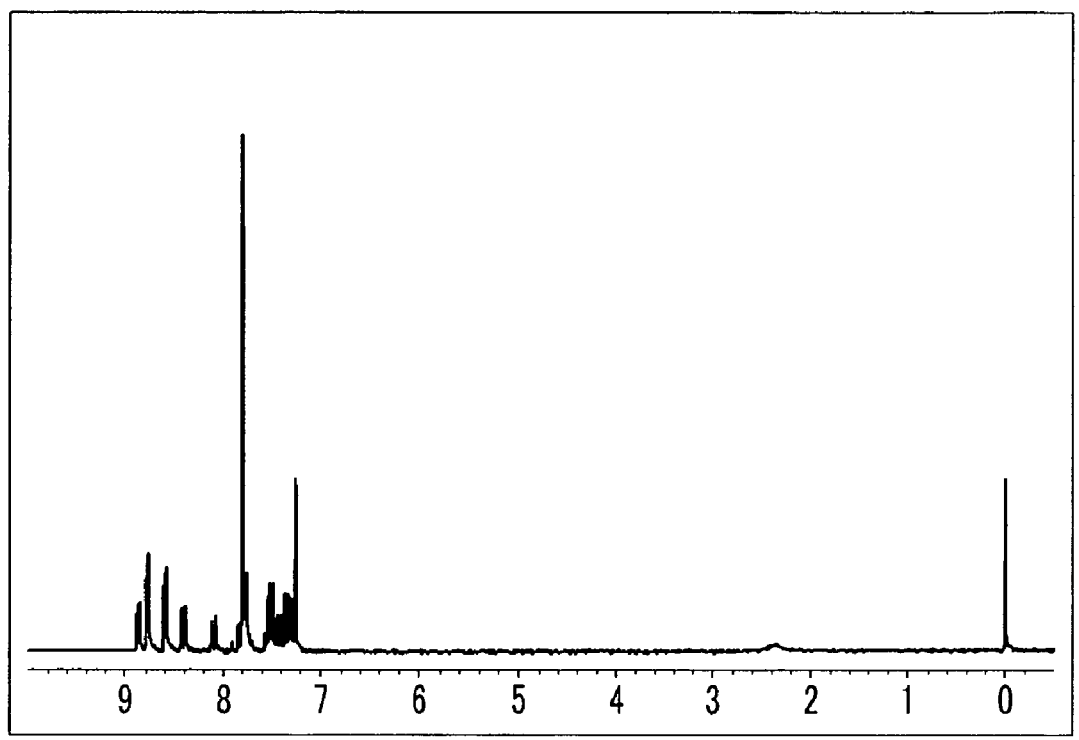
FIG. 12 illustrates a $^1H$ NMR spectrum of the compound according to Example 7 according to an embodiment.
Figure 13:
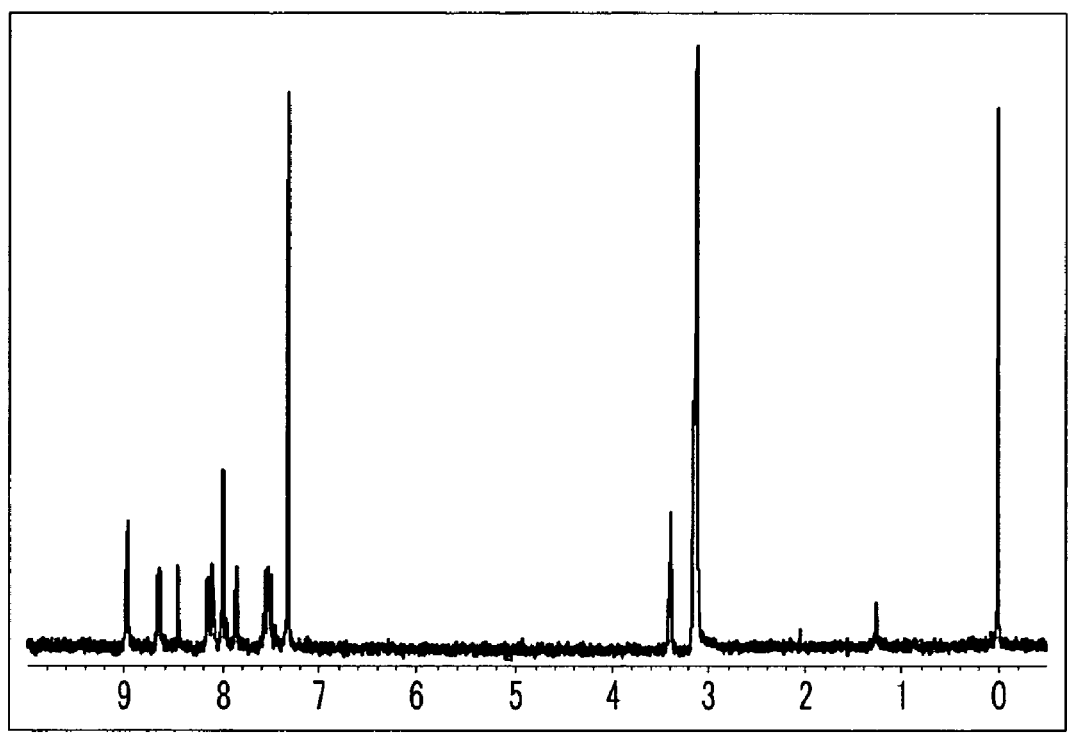
FIG. 13 illustrates a $^1$H NMR spectrum of the compound according to Example 8 according to an embodiment.
Figure 14:
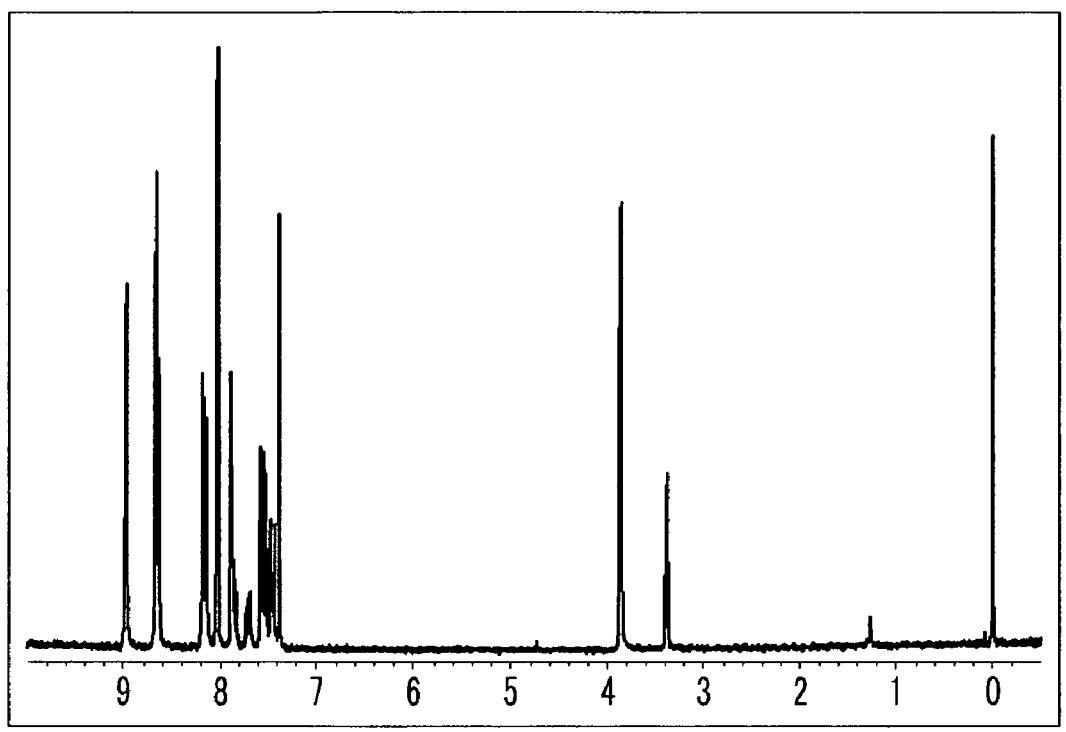
FIG. 14 illustrates a $^1$H NMR spectrum of the compound according to Example 9 according to an embodiment.
Figure 15:
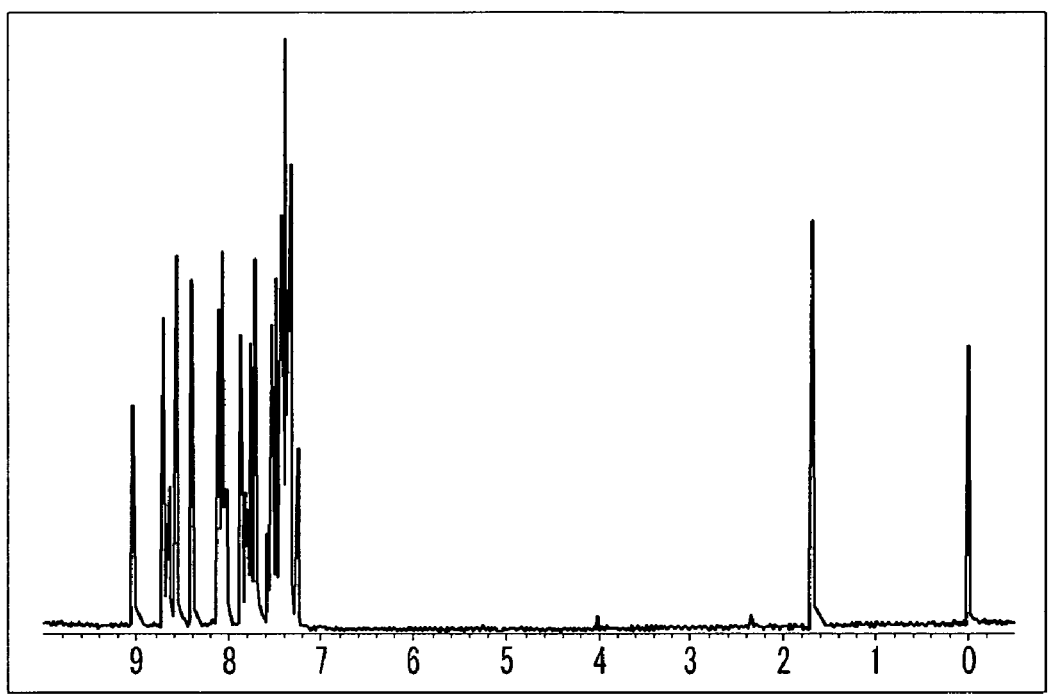
FIG. 15 illustrates a $^1$H NMR spectrum of the compound according to Example 10 according to an embodiment.
Figure 16:
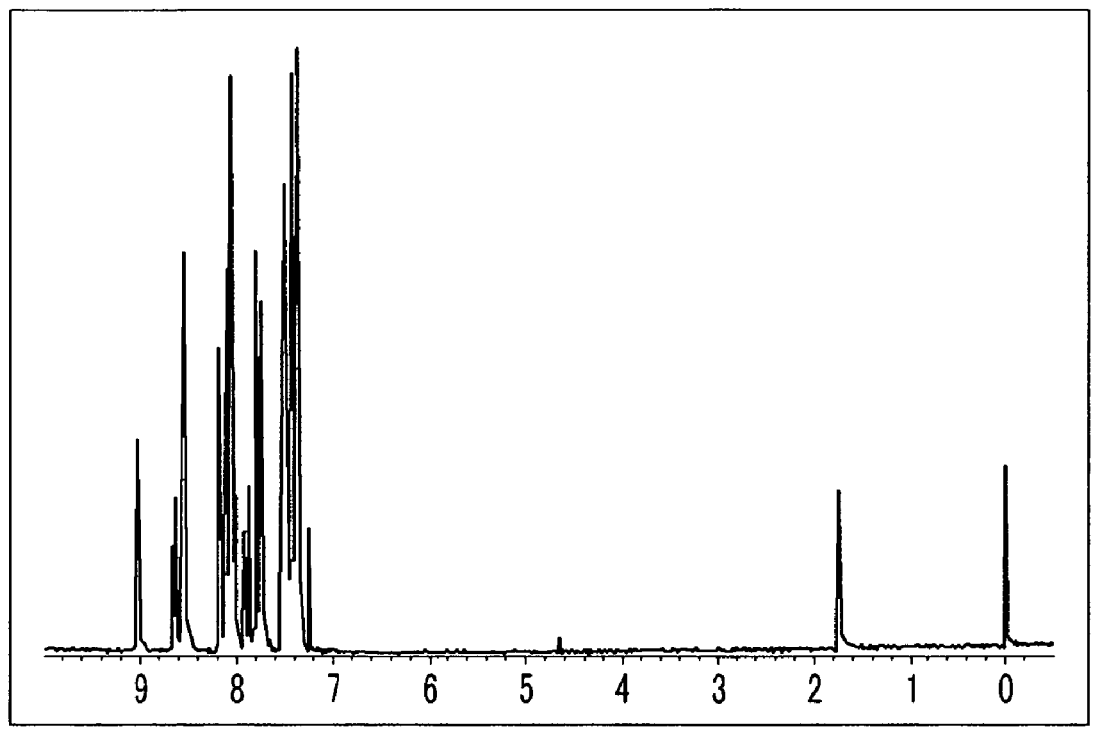
FIG. 16 illustrates a $^1$H NMR spectrum of the compound according to Example 11 according to an embodiment.
Figure 17:
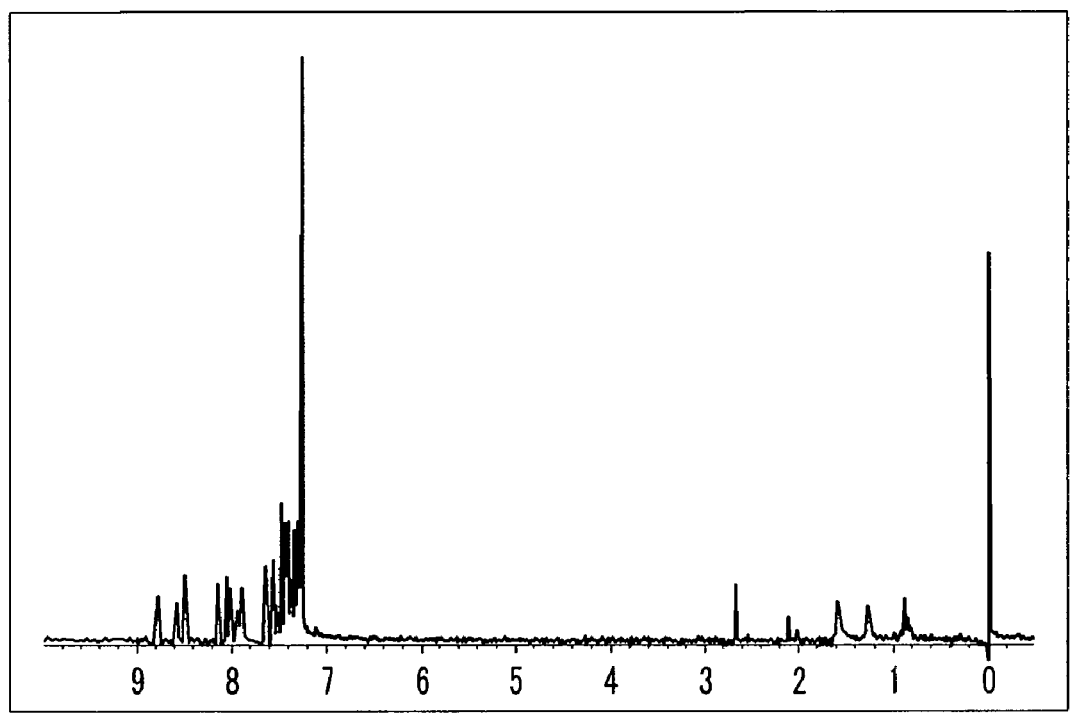
FIG. 17 illustrates a $^1$H NMR spectrum of the compound according to Example 12 according to an embodiment.

In an embodiment illustrated in FIG. 5, a five layered organic photoelectric device 500 may have an organic thin layer 105 including an electron transport layer (ETL) 150, an emission layer 130, a hole transport layer (HTL) 140, and a hole injection layer (HIL) 170, and further includes an electron injection layer (EIL) 160 to achieve a low voltage.

The organic photoelectric device may be fabricated by forming an anode on a substrate, forming an organic thin layer, and forming a cathode thereon. The organic thin layer may be formed by a dry coating method such as evaporation, sputtering, plasma plating, and ion plating, or a wet coating method such as spin coating, dipping, and flow coating.

Another embodiment provides a display device including the organic photoelectric device according to the above embodiment.

The following Examples and Comparative Examples are provided in order to set forth particular details of one or more embodiments. However, it will be understood that the embodiments are not limited to the particular details described.

Synthesis Example 1

Synthesis of 2-(3-(anthracen-9-yl)-5-bromophenyl)benzo[d]oxazole

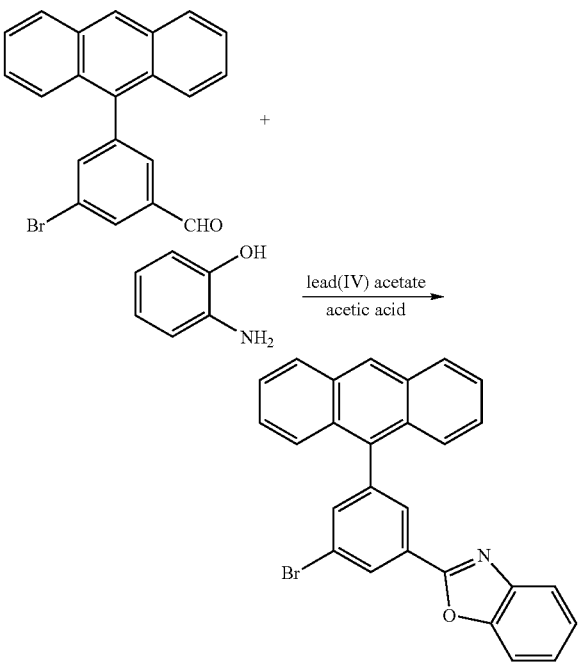

[Reaction Scheme 1]

10 g (27.7 mmol) of 3-(anthracen-9-yl)-5-bromobenzaldehyde and 3.6 g (33.2 mmol) of 2-aminophenol were dissolved in 100 ml of acetic acid, and then agitated at room temperature for 30 minutes. Next, 14.7 g (33.2 mmol) of lead (IV) acetate was added thereto. The resulting mixture was agitated at 50° C. for 1 hour. Then, water was poured therein. The resulting product was treated with ethyl acetate to perform extraction, and then the solvent was removed under reduced pressure. The extract was separated through a column and dried, gaining 4.5 g (yield (Y)=33%) of a white solid.

Synthesis Example 2

Synthesis of 2-(4-(4,4,5,5-tetramethyl-1,3,2-dioxaborolan-2-yl)phenyl)-5-phenyl-1,3,4-oxadiazole

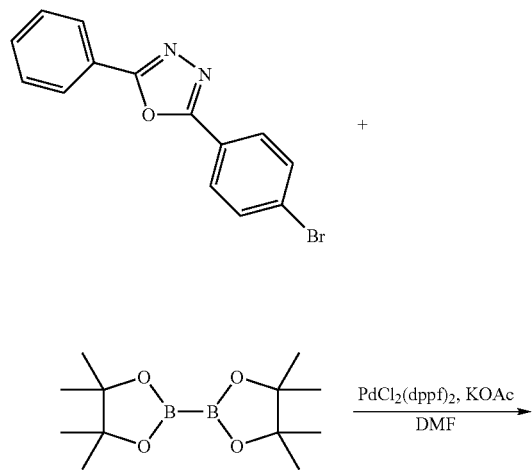

5 g (16.6 mmol) of 2-(4-bromophenyl)-5-phenyl-1,3,4-oxadiazole, 5.1 g (19.9 mmol) of bis(pinacolato)diboron, 0.41 g (3 mol %) of a complex of [1,1'-bis(diphenylphosphino)ferrocene]dichloro-palladium (II) with dichloromethane, and 4.9 g (49.8 mmol) of potassium acetate were dissolved in 100 ml of dimethylformamide (DMF). The solution was reacted at 80° C. for 12 hours. The reactant was extracted with ethyl acetate. The extract was treated under reduced pressure to remove the solvent and separated through a column, obtaining 3.1 g (Y=53%) of a light yellow solid.

Synthesis Example 3

Synthesis of 2-(3,5-dibromophenyl)-1-phenyl-1H-benzo[d]imidazole

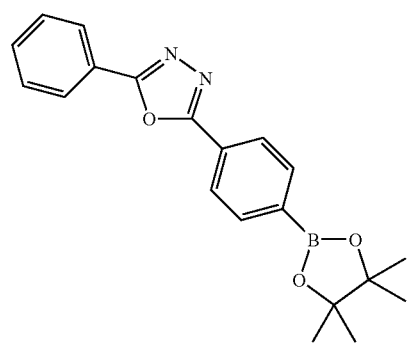

20 g (75.8 mmol) of 3,5-dibromobenzaldehyde and 16.8 g (90.9 mmol) of N-phenyl-o-phenylenediamine were dissolved in 150 mL of acetic acid. The solution was agitated at room temperature for 30 minutes. Next, 37 g (83.4 mmol) of lead (IV) acetate was added thereto. The resulting product was agitated at 50° C. for 1 hour. Then, water was poured into the acquired reactant. The resulting product was treated with ethyl acetate to perform extraction and the solvent was removed under reduced pressure. The extract was separated through a column and dried, gaining 9.5 g (Y=29%) of a yellow solid.

Synthesis Example 4

Synthesis of 2-(3-bromo-5-(pyridin-3-yl)phenyl)-1-phenyl-1H-benzo[d]imidazole

[Reaction Scheme 4]

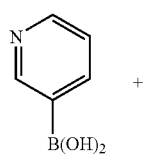

-continued

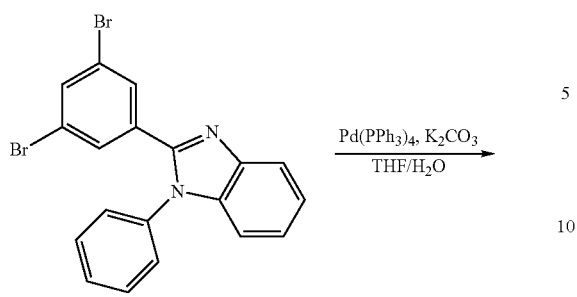

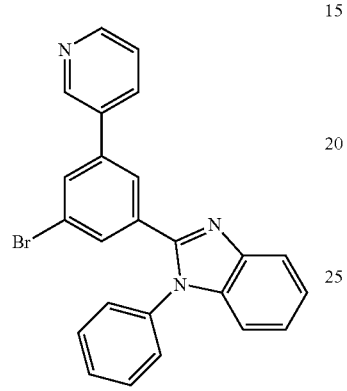

9.4 g (22.0 mmol) of 2-(3,5-dibromophenyl)-1-phenyl-1H-benzo[d]imidazole according to Synthesis Example 3, 2.7 g (22.0 mmol) of pyridine-3-boronic acid, 0.76 g (3 mol %) of tetrakis(triphenylphosphine)palladium (0), and 6.1 g (44.0 mmol) of potassium carbonate were dissolved in 300 ml of tetrahydrofuran/H$_2$O mixed in a volume ratio of 2/1. The solution was reacted at 80° C. for 12 hours. The acquired reactant was extracted with ethyl acetate and treated under reduced pressure to remove the solvent therein. The reactant was separated through a column and dried, obtaining 5.15 g (Y=54%) of a yellow solid.

Synthesis Example 5

Synthesis of
(2-(3,5-dibromophenyl)benzo[d]thiazole

[Reaction Scheme 5]

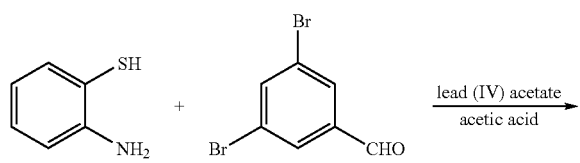

-continued 5.03 g (19.1 mmol) of 3,5-dibromobenzaldehyde and 3.1 mL (28.6 mmol) of 2-aminothiophenol were dissolved in 60 mL of acetic acid. The solution was agitated at room temperature for 30 minutes. 9.78 g (21.0 mmol) of lead (IV) acetate was added thereto. The resulting mixture was agitated at 50° C. for 1 hour. Then, water was poured into the reactant. It was extracted with ethyl acetate. The extract was separated through a column and dried, obtaining 4.74 g (Y=67%) of a white solid.

Synthesis Example 6

Synthesis of
2-(3-bromo-5-(pyridin-3-yl)phenyl)benzo[d]thiazole

[Reaction Scheme 6]

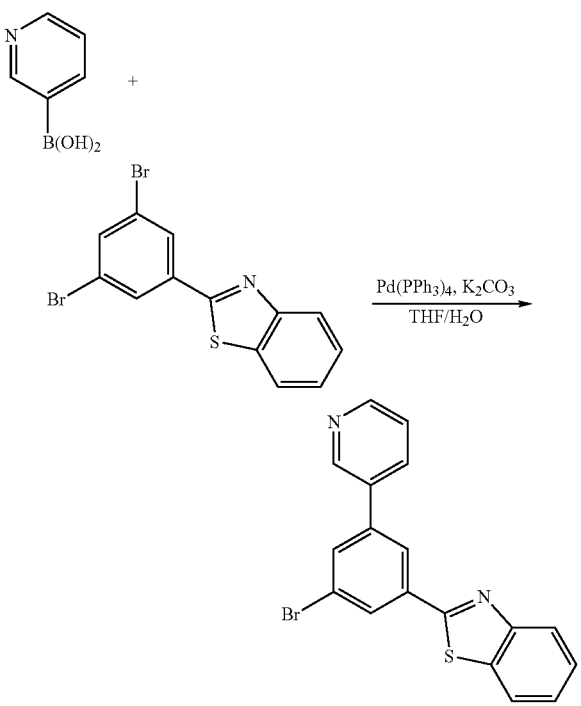

4.74 g (12.8 mmol) of 2-(3,5-dibromophenyl)benzo[d]thiazole) according to Synthesis Example 5, 1.89 g (15.4 mmol) of pyridine-3-boronic acid, 0.44 g (3 mol %) of tetrakis(triphenylphosphine)palladium (0), and 5.31 g (38.4 mmol) of potassium carbonate were dissolved in 50 ml of tetrahydrofuran/H₂O mixed in a volume ratio of 4/1. The solution was reacted at 80° C. for 12 hours. The acquired reactant was extracted with ethyl acetate and treated under reduced pressure to remove the solvent. The extract was separated through a column and dried, obtaining 2.54 g (Y=54%) of a white solid.

Synthesis Example 7

Synthesis of 3-(2H-tetrazol-5-yl)pyridine

[Reaction Scheme 7]

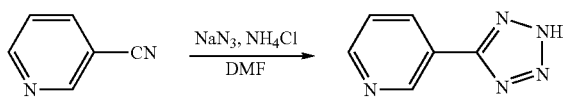

30 g (288 mmol) of 3-pyridinecarbonitrile, 28.1 g (432 mmol) of sodium azide (NaN₃), and 23.1 g (432 mmol) of ammonium chloride were dissolved in 200 mL of DMF. The solution was reacted at 100° C. for 24 hours. Then, water was added to the acquired reactant. The resulting product was neutralized with hydrochloric acid and then filtered, obtaining 19.6 g (Y=46%) of a white solid.

Synthesis Example 8

Synthesis of 3-(5-(3-bromophenyl)-1,3,4-oxadiazol-2-yl)pyridine

[Reaction Scheme 8]

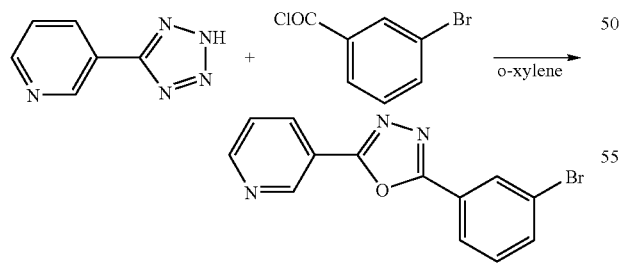

16.8 g (114 mmol) of 3-(2H-tetrazol-5-yl)pyridine) according to Synthesis Example 7 and 25 g (114 mmol) of 3-bromobenzoylchloride were dissolved in 180 mL of o-xylene. The solution was reacted at 150° C. for 8 hours. The acquired reactant was purified under reduced pressure and washed with methanol, obtaining 30 g (Y=87%) of a white solid.

Synthesis Example 9

Synthesis of 3-(5-(3-(4,4,5,5-tetramethyl-1,3,2-dioxaborolan-2-yl)phenyl)-1,3,4-oxadiazol-2-yl)pyridine

[Reaction Scheme 9]

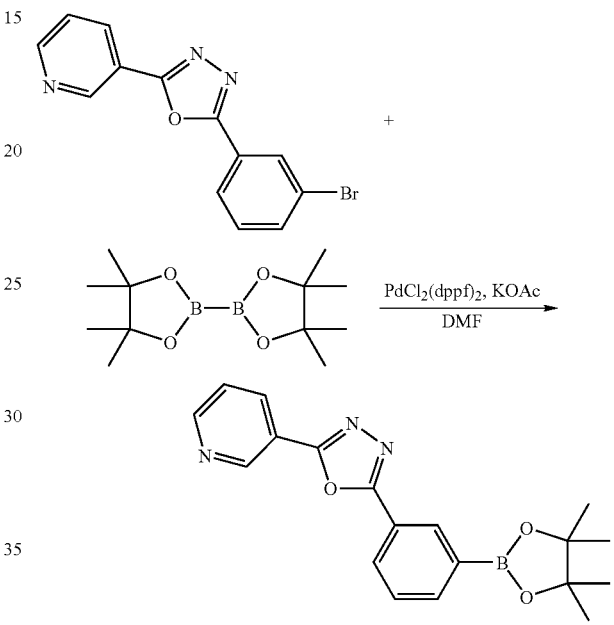

12 g (40 mmol) of 3-(5-(3-bromophenyl)-1,3,4-oxadiazol-2-yl)pyridine according to Synthesis Example 8, 12.2 g (48 mmol) of bis(pinacolato)diboron, 0.98 g (3 mol %) of a complex of [1,1'-bis(diphenylphosphino)ferrocene]dichloro-palladium(II) with dichloromethane, 5.9 g (60 mmol) of potassium acetate were dissolved in 250 ml of dimethylformamide (DMF). The solution was reacted at 80° C. for 12 hours. The acquired reactant was extracted with ethyl acetate and treated under reduced pressure to remove the solvent. The extract was separated through a column and dried, obtaining 10 g (Y=71%) of a white solid.

Synthesis Example 10

Synthesis of 2-(2,5-dibromophenyl)benzo[d]thiazole

[Reaction Scheme 10]

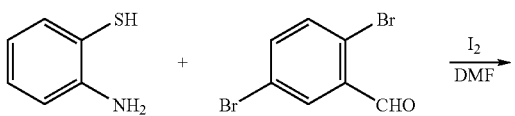

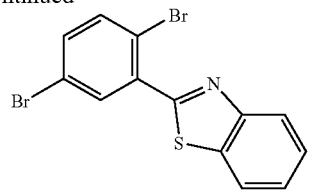

5 g (18.5 mmol) of 2,5-dibromobenzaldehyde, 3 mL (27.7 mmol) of 2-aminothiophenol, and 2.35 g (9.25 mmol) of iodine ($I_2$) were dissolved in 100 mL of DMF. The solution was reacted at 100° C. for 1 hour. The acquired reactant was purified through a column, obtaining 4.64 g (Y=68%) of a white solid.

Synthesis Example 11

Synthesis of 2-(2-bromopyridin-3-yl)benzo[d]thiazole

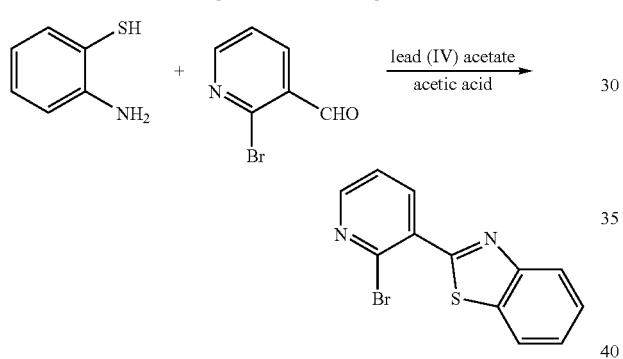

6.58 g (34.0 mmol) of 2-bromo-3-pyrdinecarboxaldehyde and 5.5 mL (50.9 mmol) of 2-aminothiophenol were dissolved in 150 mL of acetic acid. The solution was agitated at room temperature for 30 minutes. Next, 19.0 g (40.8 mmol) of lead (IV) acetate was added thereto. The resulting product was agitated at 50° C. for 1 hour. Then, water was added to the acquired reactant. The mixture was extracted with ethyl acetate and treated under reduced pressure to remove the solvent, obtaining 5.55 g (Y=55%) of a white solid.

Synthesis Example 12

Synthesis of 2-(3,5-dibromophenyl)benzo[d]oxazole

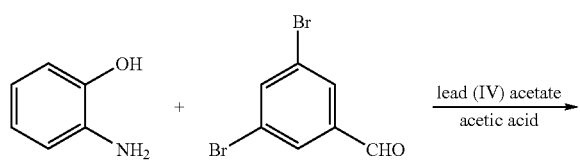

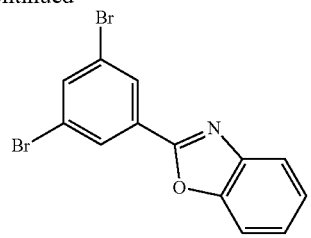

10 g (37.9 mmol) of 3,5-dibromobenzaldehyde and 5 g (45.5 mmol) of 2-aminophenol were dissolved in 200 mL of acetic acid. The solution was agitated at room temperature for 30 minutes. Next, 20.2 g (45.5 mmol) of lead (IV) acetate was added thereto. The resulting product was agitated at 50° C. for 1 hour. Then, water was added to the acquired reactant. The mixture was extracted with ethyl acetate and treated under reduced pressure to remove the solvent, obtaining 5.7 g (Y=42%) of a white solid.

Synthesis Example 13

Synthesis of 3-(anthracen-9-yl)-5-(pyridin-3-yl)benzaldehyde

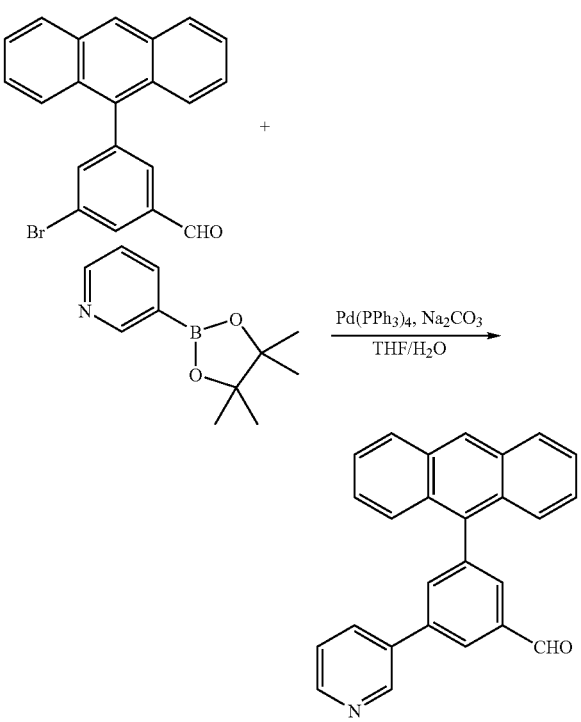

7.9 g (21.9 mmol) of 3-(anthracen-9-yl)-5-bromobenzaldehyde, 5 g (24.4 mmol of pyridine-3-boronic acid neopentylglycol ester, 0.85 g (3 mol %) of tetrakis(triphenylphosphine) palladium (0), and 5.17 g (48.8 mmol) of sodium carbonate were dissolved in 90 ml of tetrahydrofuran/$H_2O$ in a volume ratio of 2/1. The solution was reacted at 80° C. for 12 hours. The acquired reactant was extracted with ethyl acetate and treated under reduced pressure to remove the solvent. The extract was separated through a column, obtaining 7.24 g (Y=91%) of a white solid.

Example 1

Synthesis of a Compound of Chemical Formula 108

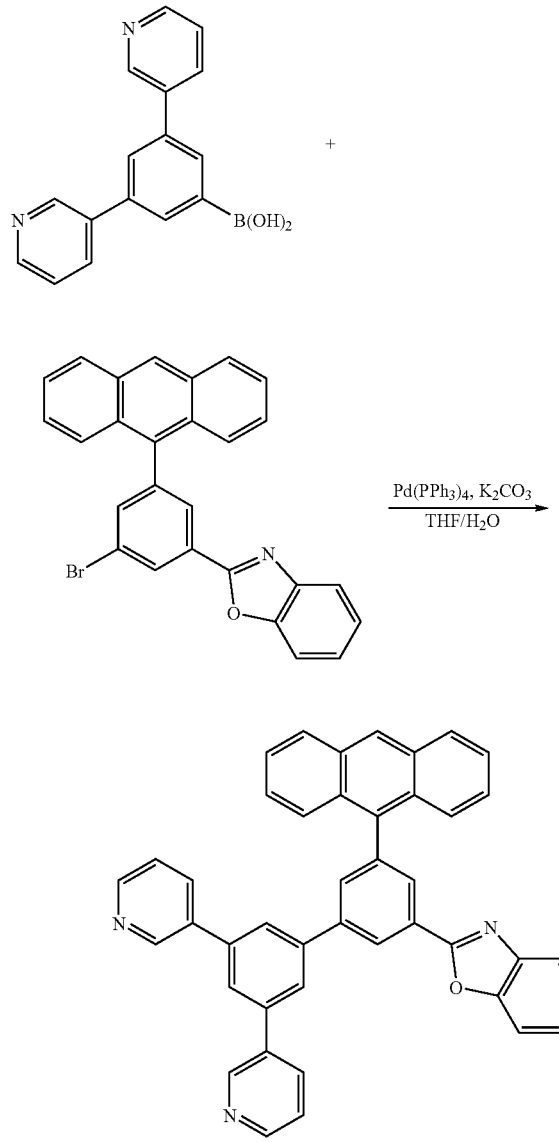

5 g (18.1 mmol) of 3,5-di-(3-pyridinyl)-benzene boronic acid, 8.16 g (18.1 mmol) of 2-(3-(anthracen-9-yl)-5-bromophenyl)benzo[d]oxazole according to Synthesis Example 1, 0.63 g (3 mol %) of tetrakis(triphenylphosphine)palladium (0), and 5 g (36.2 mmol) of potassium carbonate were dissolved in 450 ml of a solvent of tetrahydrofuran/$H_2O$ mixed in a volume ratio of 2/1. The solution was reacted at 80° C. for 12 hours. The acquired reactant was extracted with ethyl acetate and treated under reduced pressure to remove the solvent. The extract was separated through a column and dried, obtaining 6 g (Y=55%) of a white solid.

Example 2

Synthesis of a Compound of Chemical Formula 128

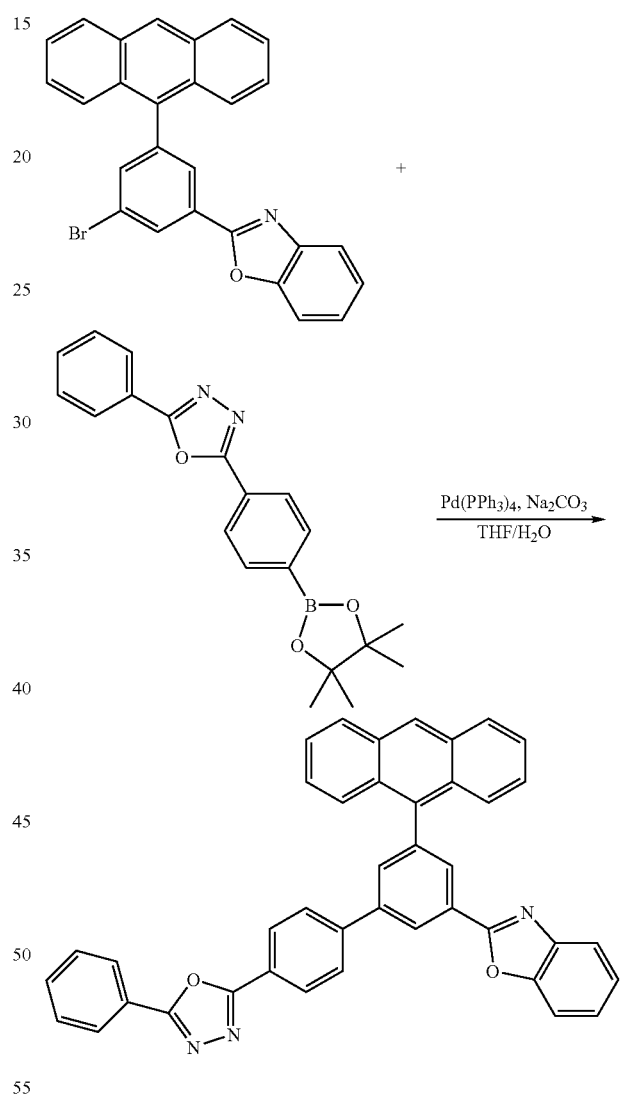

2.32 g (6.7 mmol) of (2-(4-(4,4,5,5-tetramethyl-1,3,2-dioxaborolan-2-yl)phenyl)-5-phenyl-1,3,4-oxadiazole according to Synthesis Example 2, 2.5 g (5.5 mmol) of 2-(3-(anthracen-9-yl)-5-bromophenyl)benzo[d]oxazole according to Synthesis Example 1, 0.19 g (3 mol %) of tetrakis(triphenylphosphine)palladium (0), and 1.2 g (11.1 mmol) of sodium carbonate were dissolved in 90 ml of a solvent of tetrahydrofuran/$H_2O$ mixed in a volume ratio of 2/1. The solution was reacted at 80° C. for 12 hours. The acquired reactant was extracted with ethyl acetate and treated under reduced pressure to remove the solvent. The extract was separated through a column and dried, obtaining 2.6 g (Y=79%) of a white solid.

Example 3

Synthesis of a Compound of Chemical Formula 147

[Reaction Scheme 16]

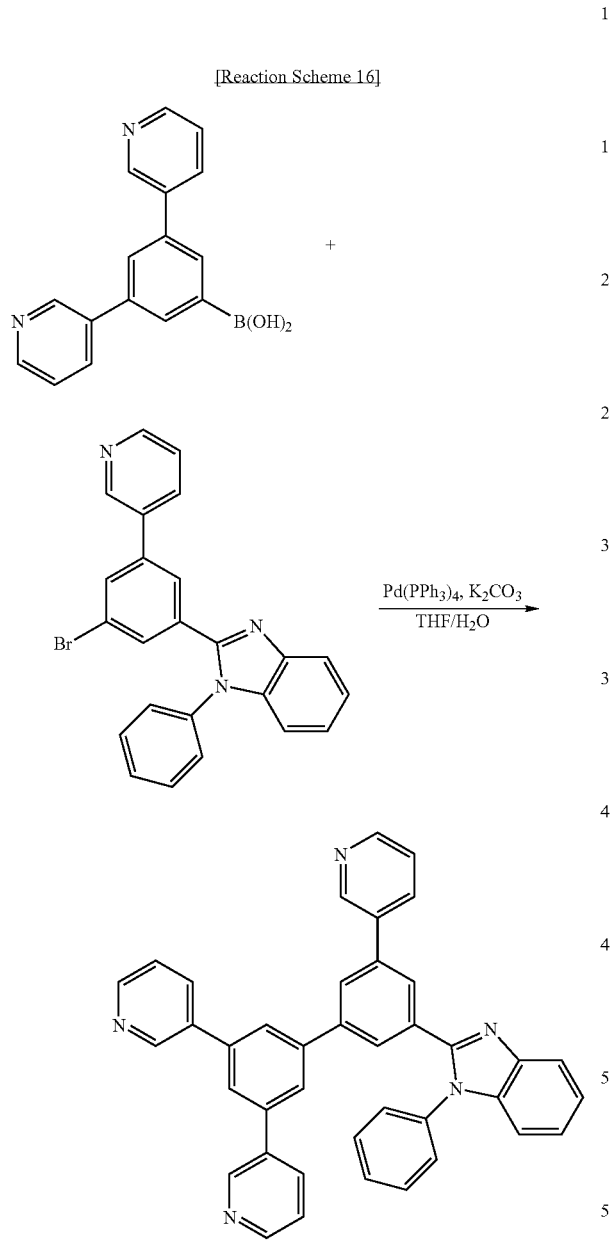

4.14 g (15.0 mmol) of 3,5-di-(3-pyridinyl)-benzene boronic acid, 6.4 g (15.0 mmol) of 2-(3-bromo-5-(pyridin-3-yl)phenyl)-1-phenyl-1H-benzo[d]imidazole according to Synthesis Example 4, 0.52 g (3 mol %) of tetrakis(triphenylphosphine)palladium (0), and 4.15 g (30.0 mmol) of potassium carbonate were dissolved in 300 ml of a solvent of tetrahydrofuran/$H_2O$ mixed in a volume ratio of 2/1. The solution was reacted at 80° C. for 12 hours. The acquired reactant was extracted with ethyl acetate and treated under reduced pressure to remove the solvent. The extract was separated through a column and dried, obtaining 1.2 g (Y=13%) of a white solid.

Example 4

Synthesis of a Compound of Chemical Formula 151

[Reaction Scheme 17]

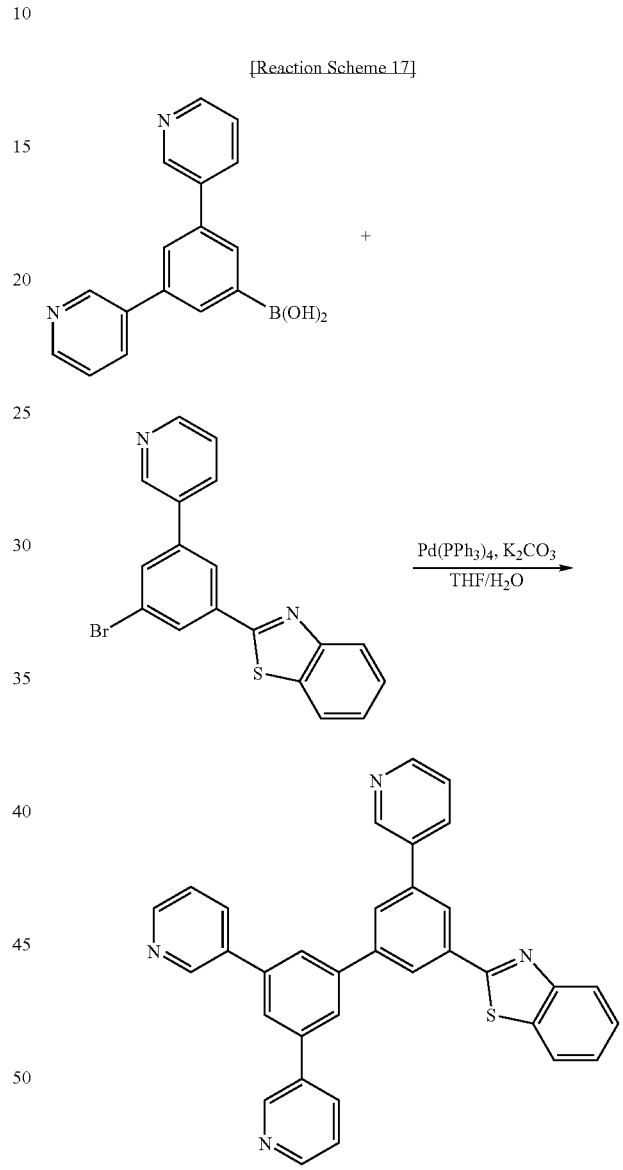

0.84 g (3.1 mmol) of 3,5-di-(3-pyridinyl)-benzene boronic acid), 1.0 g (2.8 mmol) of 2-(3-bromo-5-(pyridin-3-yl)phenyl)benzo[d]thiazole according to Synthesis Example 6, 0.14 g (5 mol %) of tetrakis(triphenylphosphine)palladium (0), and 1.15 g (8.34 mmol) of potassium carbonate were dissolved in 25 mL of a solvent of tetrahydrofuran/$H_2O$ mixed in a volume ratio of 4/1. The solution was reacted at 80° C. for 12 hours. The acquired reactant was extracted with ethyl acetate and treated under reduced pressure to remove the solvent. The extract was separated through a column and dried, obtaining 1.35 g (Y=92%) of a white solid.

Example 5

Synthesis of a Compound of Chemical Formula 156

[Reaction Scheme 18]

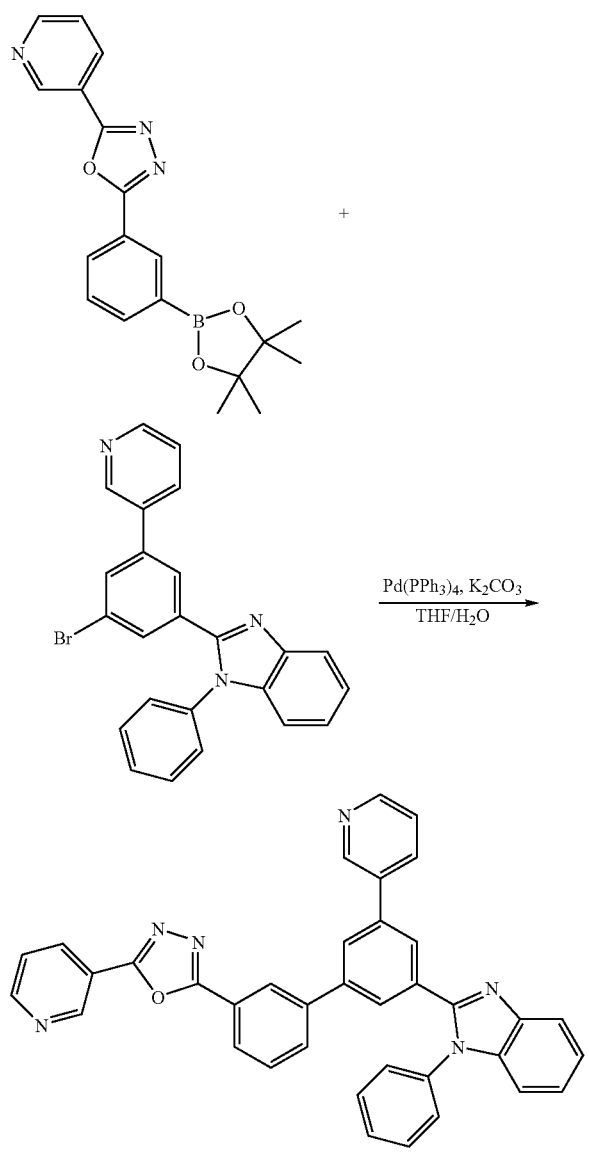

4.63 g (13.3 mmol) of 3-(5-(3-(4,4,5,5-tetramethyl-1,3,2-dioxaborolan-2-yl)phenyl)-1,3,4-oxadiazol-2-yl)pyridine according to Synthesis Example 9, 5.15 g (12.1 mmol) of 2-(3-bromo-5-(pyridin-3-yl)phenyl)-1-phenyl-1H-benzo[d]imidazole) according to Synthesis Example 4, 0.47 g (3 mol %) of tetrakis(triphenylphosphine)palladium (0), and 3.3 g (24.2 mmol) of potassium carbonate were dissolved in 300 mL of a solvent tetrahydrofuran/$H_2O$ mixed in a volume ratio of 4/1. The solution was reacted at 80° C. for 12 hours. The acquired reactant was extracted with ethyl acetate and treated under reduced pressure to remove the solvent. The extract was separated through a column and dried, obtaining 2 g (Y=33%) of a white solid.

Example 6

Synthesis of a Compound of Chemical Formula 160

[Reaction Scheme 19]

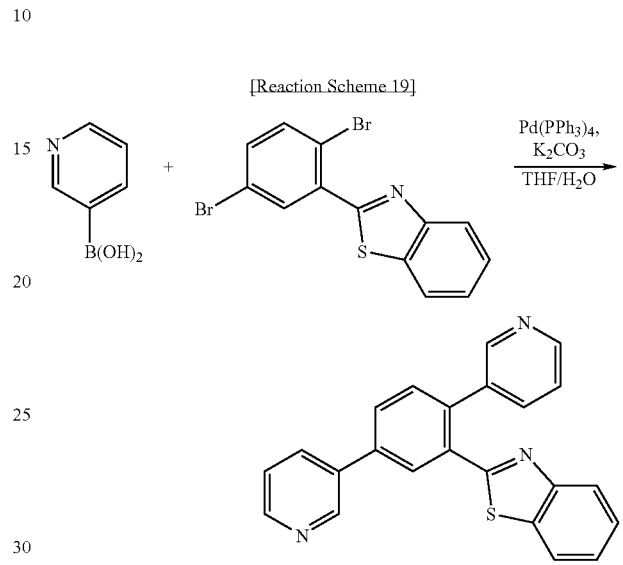

1 g (2.76 mmol) of 2-(2,5-dibromophenyl)benzo[d]thiazole according to Synthesis Example 10, 0.85 g (6.9 mmol) of pyridine-3-boronic acid, 0.28 g (10 mol %) of tetrakis(triphenylphosphine)palladium (0), and 2.3 g (16.6 mmol) of potassium carbonate were dissolved in 25 mL of a solvent of tetrahydrofuran/$H_2O$ mixed in a volume ratio of 4/1. The solution was reacted at 80° C. for 12 hours. The acquired reactant was extracted with ethyl acetate and treated under reduced pressure to remove the solvent. The extract was separated through a column and dried, obtaining 0.8 g (Y=79%) of a white solid.

Example 7

Synthesis of a Compound of Chemical Formula 169

[Reaction Scheme 20]

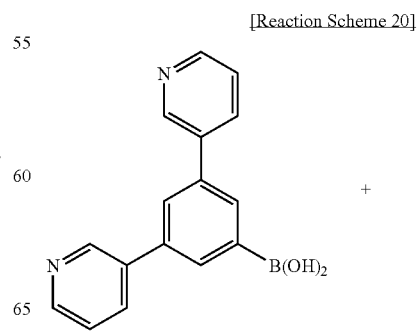

-continued

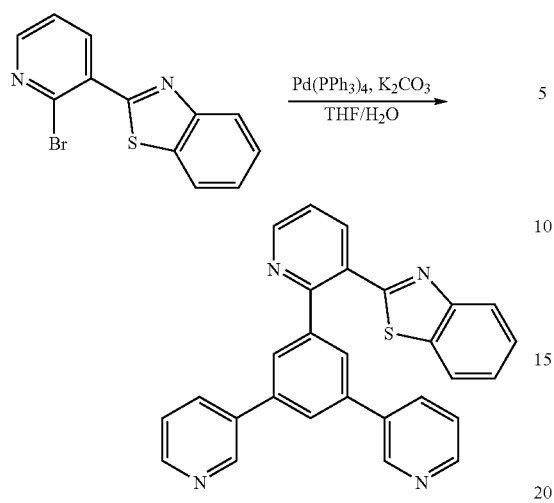

1.33 g (4.8 mmol) of 3,5-di-(3-pyridinyl)-benzene boronic acid, 1.7 g (5.8 mmol) of 2-(2-bromopyridine-3-yl)benzo[d]thiazole according to Synthesis Example 11, 0.28 g (5 mol %) of tetrakis(triphenylphosphine)palladium (0), and 2.0 g (14.4 mmol) of potassium carbonate were dissolved in 30 mL of a solvent of tetrahydrofuran/H$_2$O mixed in a volume ratio of 4/1. The solution was reacted at 80° C. for 12 hours. The acquired reactant was extracted with ethyl acetate and treated under reduced pressure to remove the solvent. The extract was separated through a column and dried, obtaining 2.28 g (Y=88%) of a white solid.

2.3 g (8.4 mmol) of 3,5-di-(3-pyridinyl)-benzene boronic acid, 1.5 g (4.0 mmol) of 2-(3,5-dibromophenyl)benzo[d]thiazole according to Synthesis Example 5, 0.46 g (10 mol %) of tetrakis(triphenylphosphine)palladium (0), and 3.3 g (23.9 mmol) of potassium carbonate were dissolved in 50 mL of a solvent of tetrahydrofuran/H$_2$O mixed in a volume ratio of 4/1. The solution was reacted at 80° C. for 12 hours. The acquired reactant was extracted with ethyl acetate and treated under reduced pressure to remove the solvent. The extract was separated through a column and dried, obtaining 2.04 g (Y=75%) of a white solid.

Example 8

Synthesis of a Compound of Chemical Formula 172

[Reaction Scheme 21]

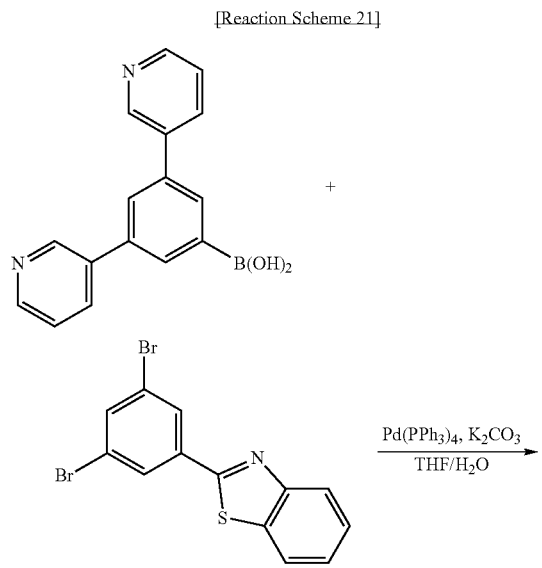

Example 9

Synthesis of a Compound of Chemical Formula 174

[Reaction Scheme 22]

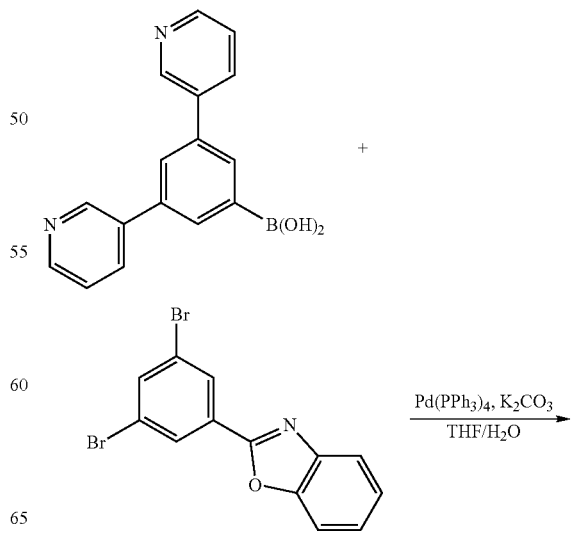

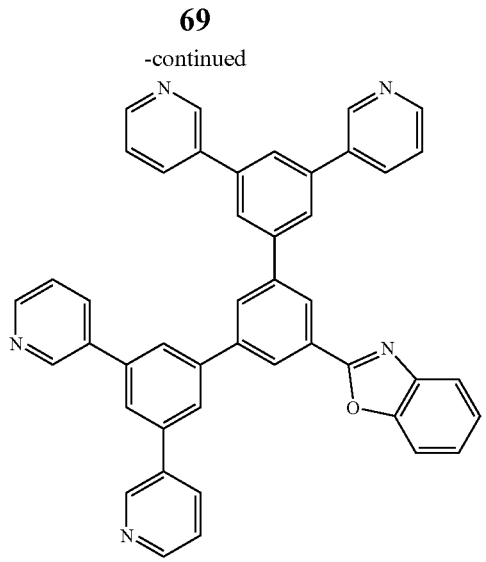

4.3 g (15.6 mmol) of 3,5-di-(3-pyridinyl)-benzene boronic acid, 2.5 g (7.1 mmol) of 2-(3,5-dibromophenyl)benzo[d]oxazole according to Synthesis Example 12, 0.82 g (10 mol %) of tetrakis(triphenylphosphine)palladium (0), and 5.9 g (42.7 mmol) of potassium carbonate were dissolved in 100 mL of a solvent of tetrahydrofuran/H$_2$O mixed in a volume ratio of 4/1. The solution was reacted at 80° C. for 12 hours. The acquired reactant was extracted with ethyl acetate and treated under reduced pressure to remove the solvent. The extract was separated through a column and dried, obtaining 3.37 (Y=72%) of a white solid.

Example 10

Synthesis of a Compound of Chemical Formula 68

[Reaction Scheme 23]

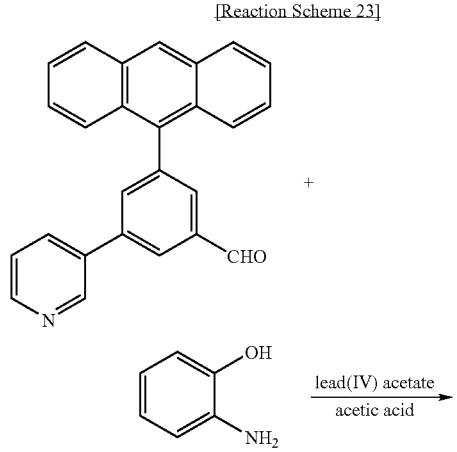

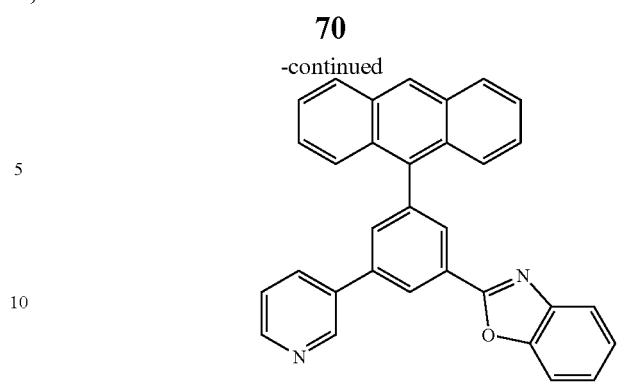

3 g (8.3 mmol) of 3-(anthracen-9-yl)-5-(pyridin-3-yl)benzaldehyde according to Synthesis Example 13 and 0.91 g (8.3 mmol) of 2-aminophenol were dissolved in 80 ml of acetic acid. The solution was agitated at room temperature for 30 minutes. Next, 4.4 g (9.96 mmol) of lead (IV) acetate was added thereto. The resulting product was agitated at 50° C. for 1 hour. Then, water was poured into the acquired reactant. The mixture was extracted with ethyl acetate and treated under reduced pressure to remove the solvent. The extract was separated through a column and dried, obtaining 2.17 g (Y=58%) of a white solid.

Example 11

Synthesis of a Compound of Chemical Formula 71

[Reaction Scheme 24]

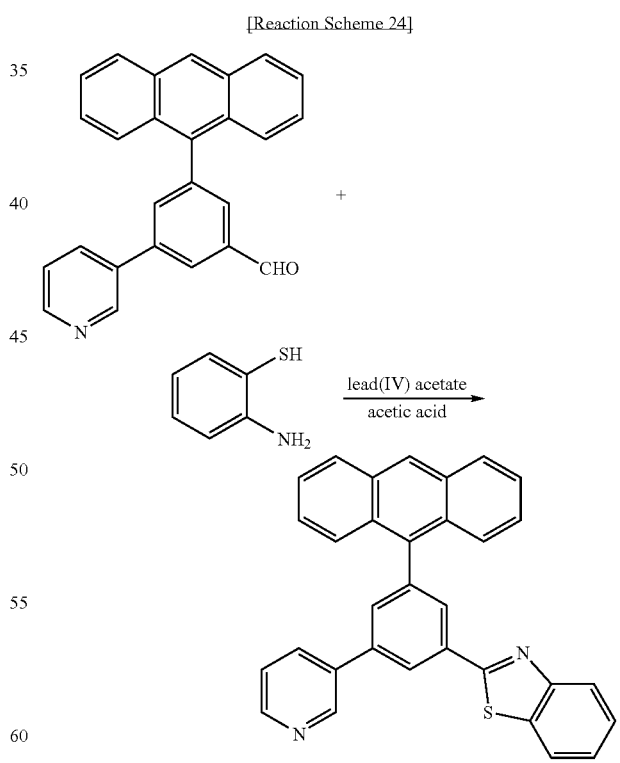

3 g (8.3 mmol) of 3-(anthracen-9-yl)-5-(pyridin-3-yl)benzaldehyde according to Synthesis Example 13 and 1.25 g (10 mmol) of 2-aminothiophenol were dissolved in 40 ml of acetic acid. The solution was agitated at room temperature for 30 minutes. Next, 4.4 g (9.96 mmol) of lead (IV) acetate was added thereto. The resulting mixture was agitated at 50° C. for 1 hour. Then, water was added to the acquired product. The resulting mixture was extracted with ethyl acetate. The extract was treated under reduced pressure to remove the solvent, and then separated through a column and dried, obtaining 2.74 g (Y=71%) of a white solid.

Example 12

Synthesis of a Compound of Chemical Formula 77

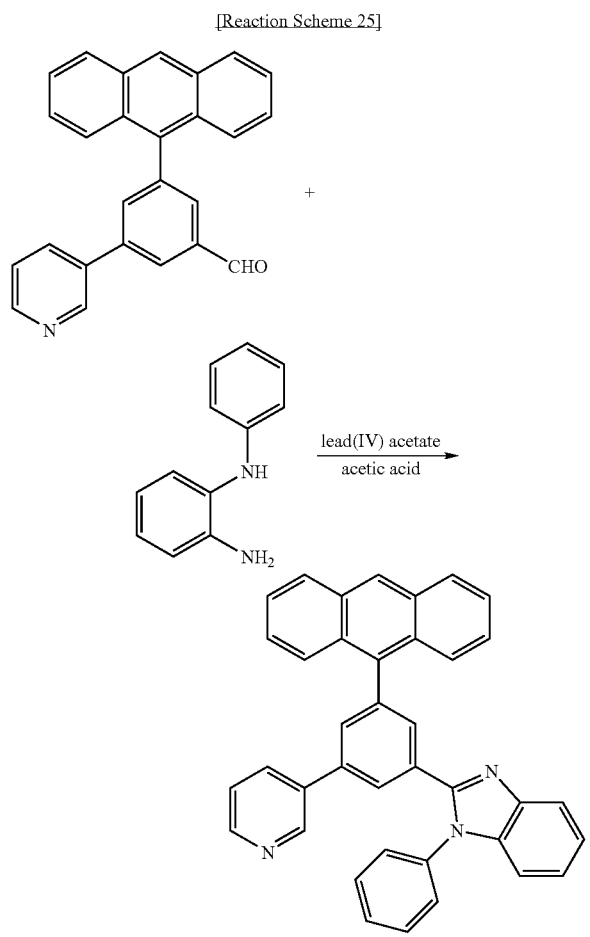

[Reaction Scheme 25]

0.36 g (1 mmol) of 3-(anthracen-9-yl)-5-(pyridin-3-yl) benzaldehyde according to Synthesis Example 13 and 0.22 g (1.2 mmol) of N-phenyl-o-phenylenediamine were dissolved in 30 ml of acetic acid. The solution was agitated at room temperature for 30 minutes. Next, 0.53 g (1.2 mmol) of lead (IV) acetate was added thereto. The resulting mixture was agitated at 50° C. for 1 hour. Then, water was poured into the acquired reactant. The resulting product was extracted with ethyl acetate and treated under reduced pressure to remove the solvent. The extract was separated through a column and dried, gaining 0.27 g (Y=51%) of a white solid.

The compounds according to Examples 1 to 12 were analyzed through $^1$H NMR (nuclear magnetic resonance spectroscopy). The results are respectively provided in FIGS. 6 to 17.

Comparative Example 1

2-(4-biphenyl)-5-(4-t-butylphenyl)-1,3,4-oxadiazole (PBD)

2-(4-biphenyl)-5-(4-t-butylphenyl)-1,3,4-oxadiazole (PBD), which has an excellent charge transfer capability (Jpn. J. Appl. Phys., 27, L269 1988), was prepared.

Example 13

Fabrication of an Organic Light Emitting Diode

A 15 $\Omega/cm^2$ (120 nm) ITO glass substrate (Corning, Inc.) was prepared to have a size of 25 mm×25 mm×0.7 mm, and was respectively washed in isopropyl alcohol and pure water for 5 minutes, and was then cleaned again with UV and ozone.

Next, a 40 nm-thick N,N'-di(4-(N,N'-diphenyl-amino)-phenyl)-N,N'-diphenylbenzidine (DNTPD) hole injection layer (HIL) was formed on the substrate.

Then, N,N'-bis(naphthalene-1-yl)-N,N'-bis(phenyl)benzidine (NPB) was vacuum-deposited to form a 10 nm-thick hole transport layer (HTL) on the hole injection layer (HIL).

EB-46 and EB-512 (e-Ray Optoelectronics Technology Co., Ltd.) as a light emitting material were vacuum-deposited in a weight ratio of 94:6 to form a 40 nm-thick emission layer on the hole transport layer (HTL).

The compound according to Example 2 as an electron transport material was vacuum-deposited to form a 10 nm-thick electron transport layer (ETL) on the emission layer.

On the electron transport layer (ETL), LiF 0.5 nm/Al 100 nm were respectively and sequentially vacuum-deposited to form a cathode including LiF/Al, fabricating an organic light emitting diode of Example 13.

Example 14

Fabrication of an Organic Light Emitting Diode

An organic light emitting diode was fabricated according to the same method as Example 13, except for using a compound according to Example 3 to form an electron transport layer (ETL).

Example 15

Fabrication of an Organic Light Emitting Diode

An organic light emitting diode was fabricated according to the same method as Example 13, except for using a compound according to Example 4 to form an electron transport layer (ETL).

Example 16

Fabrication of an Organic Light Emitting Diode

An organic light emitting diode was fabricated according to the same method as Example 13, except for using a compound according to Example 5 to form an electron transport layer (ETL).

Example 17

Fabrication of an Organic Light Emitting Diode

An organic light emitting diode was fabricated according to the same method as Example 13, except for using a compound according to Example 7 to form an electron transport layer (ETL).

Example 18

Fabrication of an Organic Light Emitting Diode

An organic light emitting diode was fabricated according to the same method as Example 13, except for using a compound according to Example 8 to form an electron transport layer (ETL).

Example 19

Fabrication of an Organic Light Emitting Diode

An organic light emitting diode was fabricated according to the same method as Example 13, except for using a compound according to Example 9 to form an electron transport layer (ETL).

Comparative Example 2

Fabrication of an Organic Light Emitting Diode

An organic light emitting diode was fabricated according to the same method as Example 13, except for using an electron transport material of $Alq_3$ to form an electron transport layer (ETL).

Example 20

Fabrication of an Organic Light Emitting Diode

A 15 $\Omega/cm^2$ (120 nm) ITO glass substrate (Corning, Inc.) was prepared to have a size of 25 mm×25 mm×0.7 mm, and was respectively cleaned in isopropyl alcohol and pure water for 5 minutes, and then with UV and ozone for 30 minutes.

Next, a 40 nm-thick hole transport layer (HTL) was formed by vacuum-depositing N,N'-di(1-naphthyl)-N,N'-diphenylbenzidine (NPD) on the substrate.

On the hole transport layer (HTL), 4,4'-bis(carbazol-9-yl) biphenyl (CBP) as a phosphorescent host and tris(phenylpyridine)iridium as a phosphorescent dopant were vacuum-deposited in a weight ratio of 90:10 to form a 30 nm-thick emission layer.

Then, a 5 nm-thick hole blocking layer was formed by vacuum-depositing BAlq on the emission layer.

On the hole blocking layer, the compound of Example 1 as an electron transport material was vacuum-deposited to form a 20 nm-thick electron transport layer (ETL).

Then, LiF 5 nm/Al 100 nm were respectively and sequentially vacuum-deposited to form a cathode including LiF/Al on the electron transport layer (ETL), fabricating an organic light emitting diode of Example 20.

Example 21

Fabrication of an Organic Light Emitting Diode

An organic light emitting diode was fabricated according to the same method as Example 20, except for using a compound of Example 2 to form an electron transport layer (ETL).

Example 22

Fabrication of an Organic Light Emitting Diode

An organic light emitting diode was fabricated according to the same method as Example 20, except for using a compound represented by Chemical Formula 96 according to Example 10 to form an electron transport layer (ETL).

Example 23

Fabrication of an Organic Light Emitting Diode

An organic light emitting diode was fabricated according to the same method as Example 20, except for using a compound represented by Chemical Formula 119 according to Example 11 to form an electron transport layer (ETL).

Comparative Example 3

Fabrication of an Organic Light Emitting Diode

An organic light emitting diode was fabricated according to the same method as Example 20, except for using an electron transport material of $Alq_3$ to form an electron transport layer (ETL).

Property Measurement and Analysis

1) Thermal Stability Measurement

Figure 18:
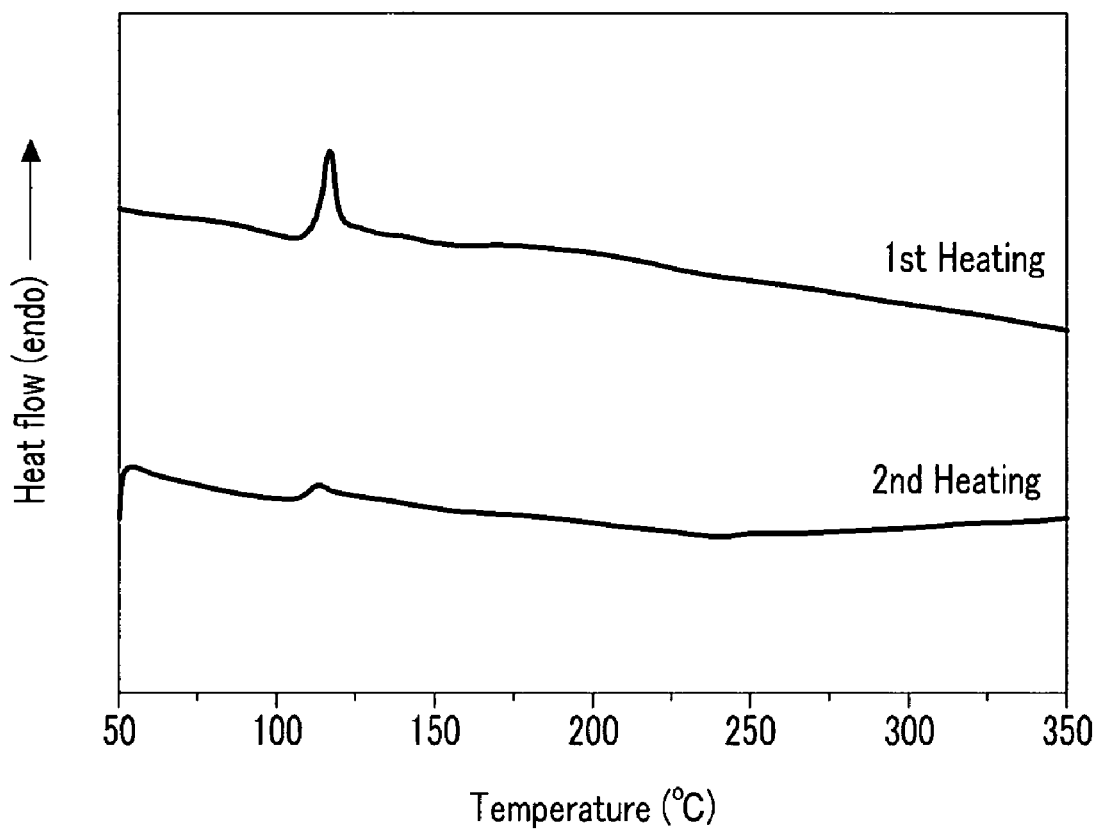
FIG. 18 illustrates a thermal characteristic of the compound according to Example 5.
Figure 19:
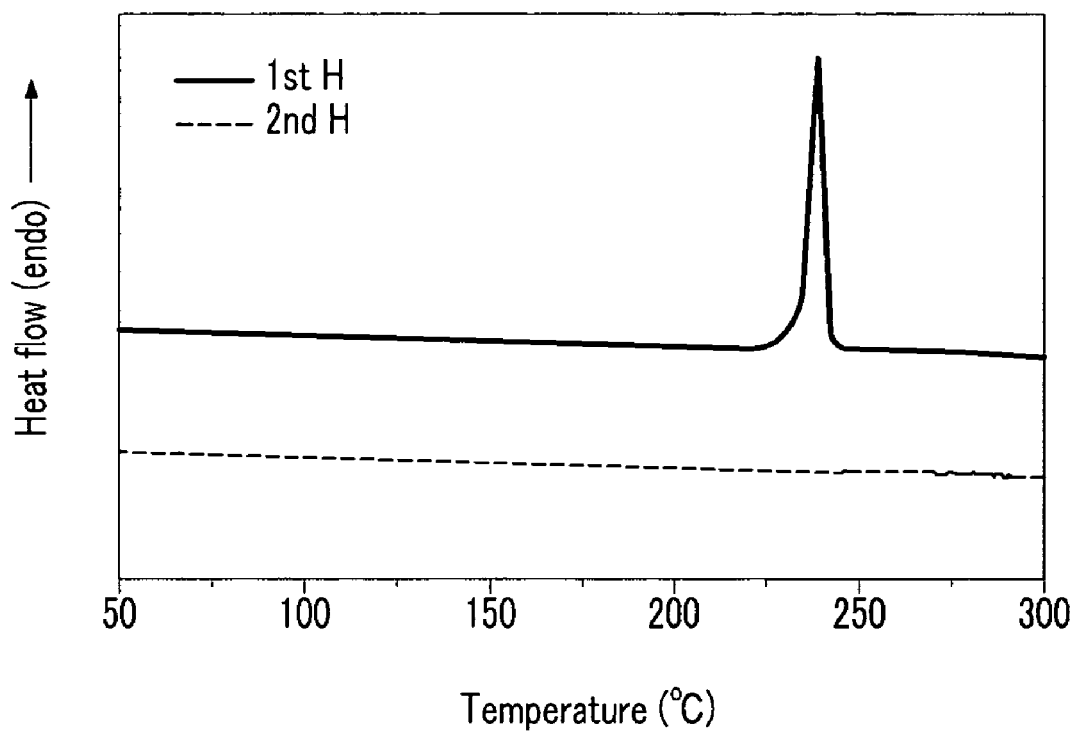
FIG. 19 illustrates a thermal characteristic of the compound according to Example 10.
Figure 20:
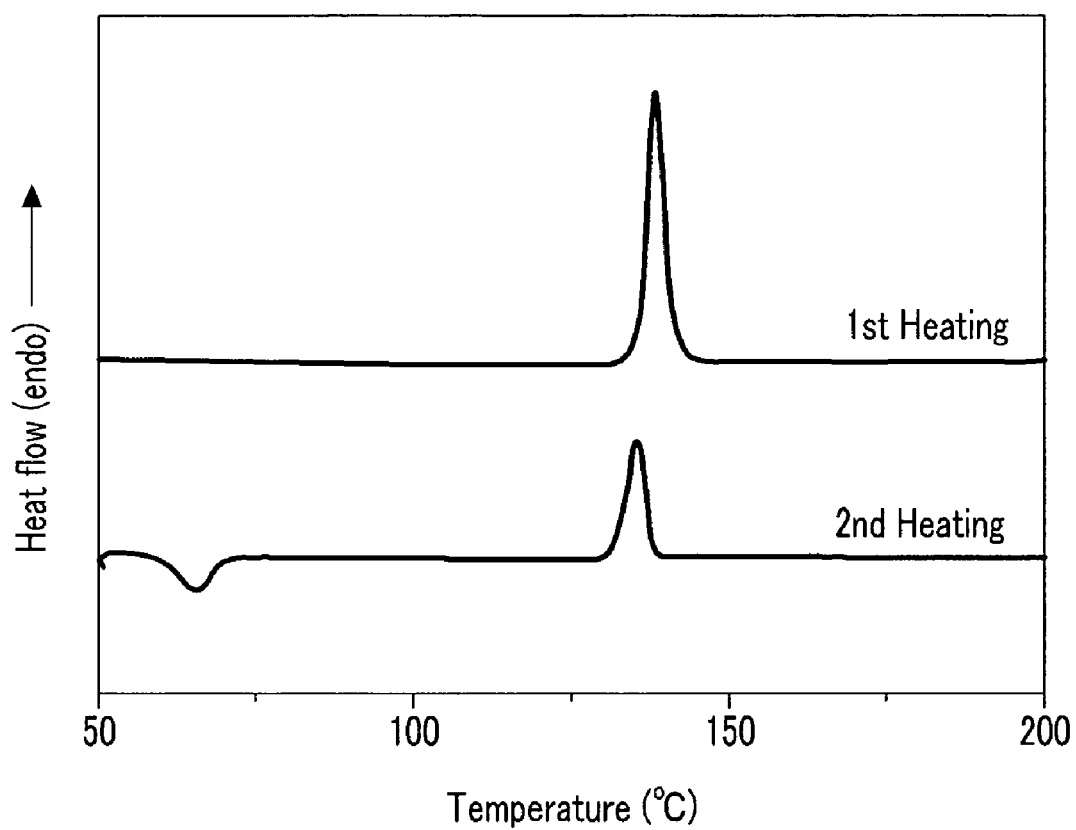
FIG. 20 illustrates a thermal characteristic of the compound according to Comparative Example 1.
Figure 21:
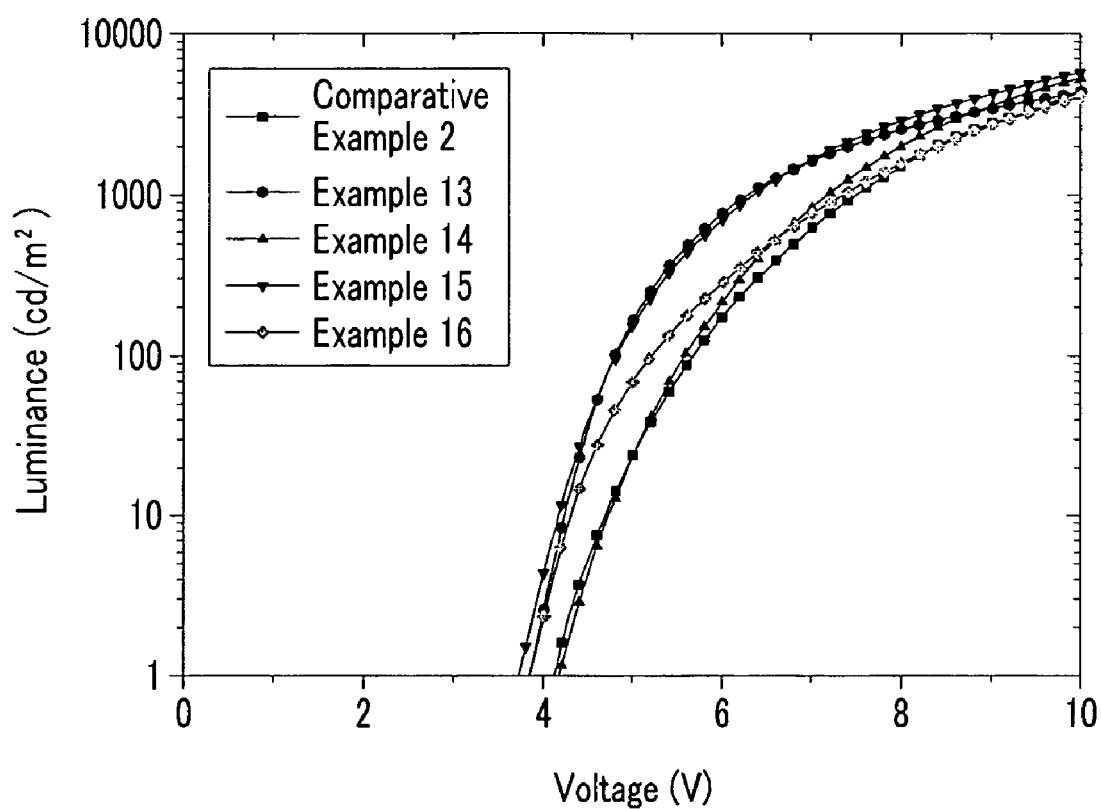
FIG. 21 illustrates voltage-luminescence characteristics of the organic light emitting diodes according to Examples 13 to 16 and Comparative Example 2.
Figure 22:
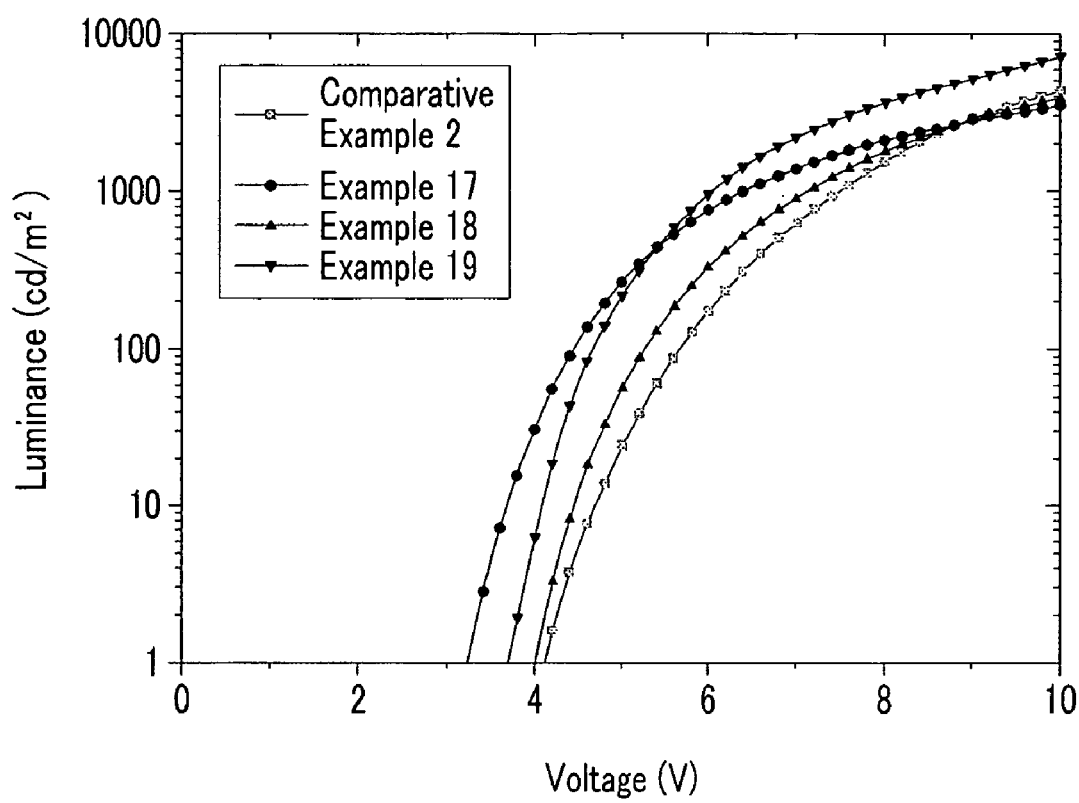
FIG. 22 illustrates voltage-luminescence characteristics of the organic light emitting diodes according to Examples 17 to 19 and Comparative Example 2.
Figure 23:
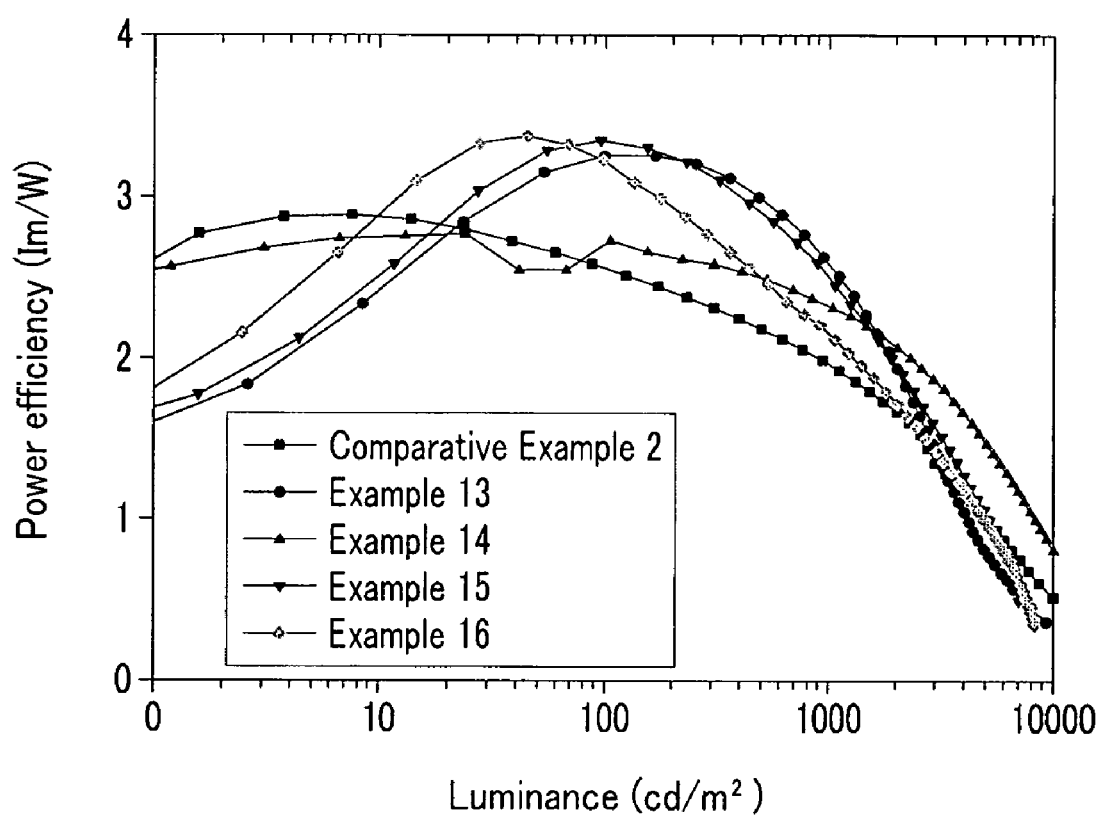
FIG. 23 illustrates electrical power efficiency of the organic light emitting diodes according to Examples 13 to 16 and Comparative Example 2.
Figure 24:
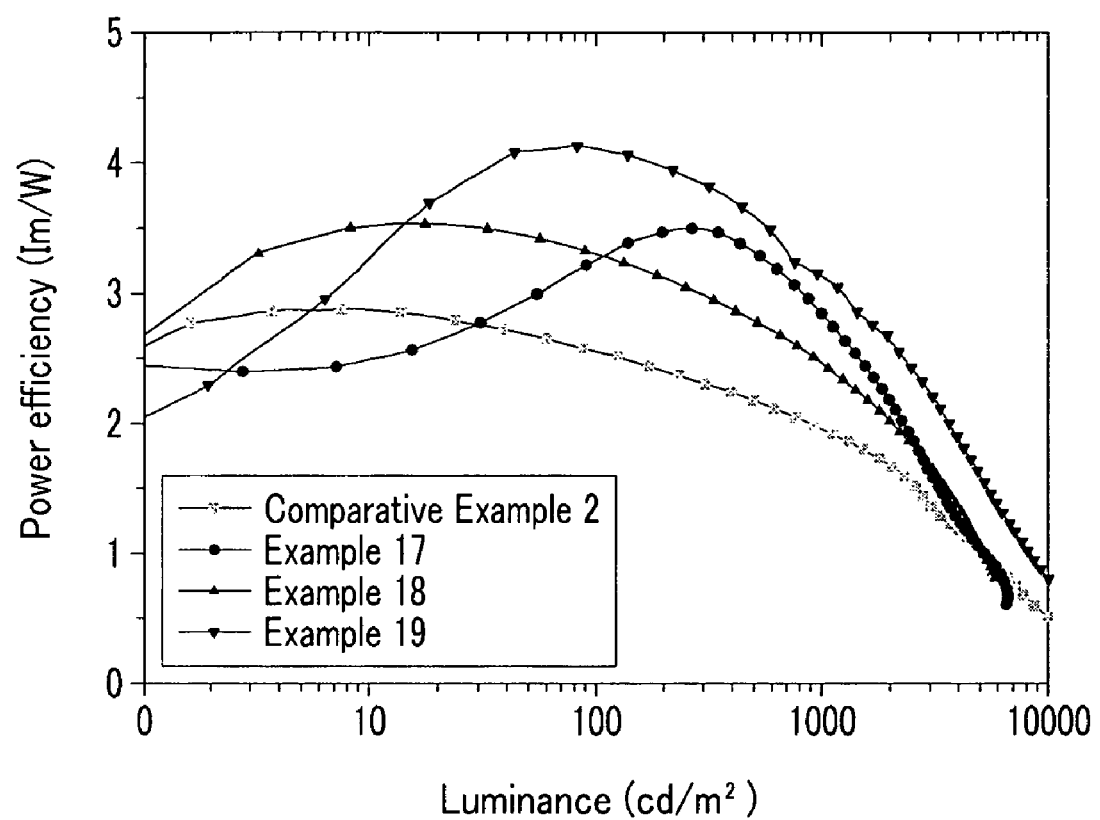
FIG. 24 illustrates electrical power efficiency of the organic light emitting diodes according to Examples 17 to 19 and Comparative Example 2.
Figure 25:
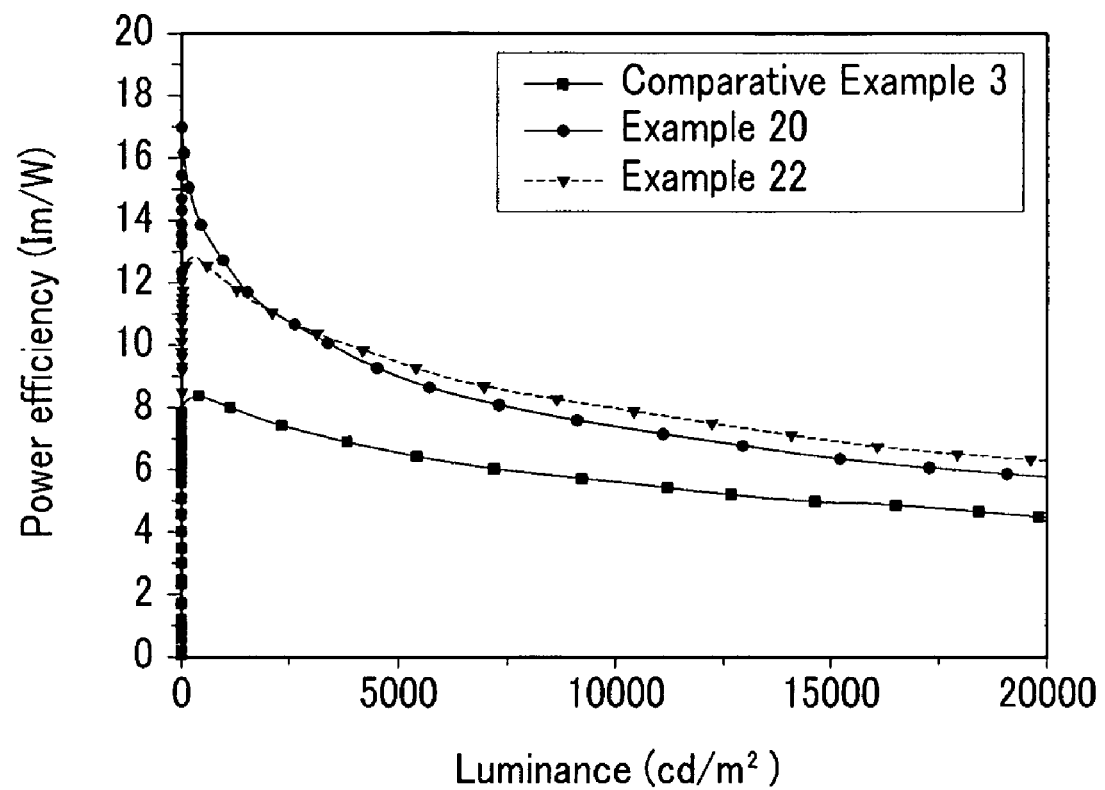
FIG. 25 illustrates electrical power efficiency of the organic light emitting diodes according to Examples 20 and 22 and Comparative Example 3.
Figure 26:
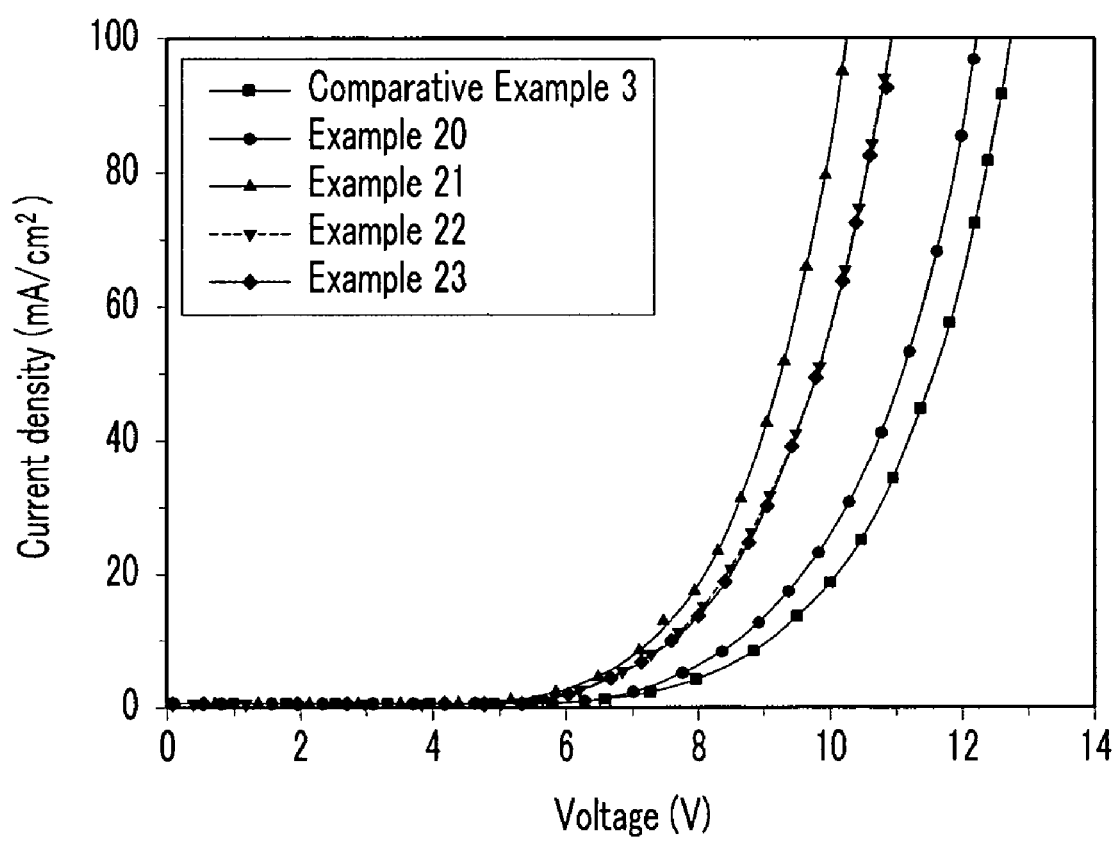
FIG. 26 illustrates current density characteristics of the organic light emitting diode according to Examples 20 to 23 and Comparative Example 3.

The compounds according to Examples 1 to 12 were analyzed in a differential scanning calorimetry method (DSC), and then secondarily analyzed in the same method. The analysis results of the compounds according to Examples 5 and 10 and Comparative Example 1 are shown in FIGS. 18 to 20. Referring to FIGS. 18 to 20, the compounds of Examples 5 and 10 had some or no fusing point peak in the primary analysis, but no fusing point peak in the secondary analysis. In contrast, 2-(4-biphenyl)-5-(4-t-butylphenyl)-1,3,4-oxadiazole (PBD) according to Comparative Example 1 had a fusing point peak at 138° C. in both primary and secondary analyses and a crystallizing temperature at 65° C. in the secondary analysis. The compounds of Examples 5 and 10 were identified to stably exist as amorphous compared with a conventional material. Therefore, the organic light emitting diodes including the compounds according to embodiments of the present invention reduced influence of Joule heat generated during the operation, and thereby may afford an improved life-span characteristic compared with a conventional organic light emitting diode.

2) Measurement of Driving Voltage, Luminance, and Luminous Efficiency

The organic light emitting diode of Examples 13 to 23 and Comparative Examples 2 to 3 were measured regarding driving voltage (Vd) required to produce brightness of 1000 nit, and current efficiency (cd/A) and electric power efficiency (lm/W) at the same brightness. The results are shown in the following Table 1.

TABLE 1

| Device | At 1000 cd/m² | | | | Max | |
|---|---|---|---|---|---|---|
| | Vd (V) | cd/A | lm/W | Von | cd/A | lm/W |
| Comparative Example 2 | 7.40 | 4.68 | 1.99 | 3.60 | 4.72 | 2.88 |
| Example 13 | 6.20 | 5.19 | 2.63 | 3.20 | 5.35 | 3.25 |
| Example 14 | 7.20 | 5.29 | 2.31 | 3.80 | 5.32 | 2.77 |
| Example 15 | 6.40 | 5.00 | 2.45 | 3.00 | 5.32 | 3.34 |
| Example 16 | 7.40 | 4.99 | 2.12 | 3.20 | 5.32 | 3.37 |
| Example 17 | 6.40 | 5.80 | 2.85 | 3.00 | 5.88 | 3.51 |
| Example 18 | 7.20 | 5.56 | 2.43 | 3.40 | 5.66 | 3.54 |
| Example 19 | 6.00 | 6.04 | 3.16 | 3.20 | 6.32 | 4.14 |
| Comparative Example 3 | 8.00 | 21.60 | 8.48 | 3.40 | 22.92 | 8.6 |
| Example 20 | 6.40 | 25.14 | 12.34 | 3.20 | 25.80 | 12.85 |
| Example 21 | 7.00 | — | — | 3.00 | — | — |
| Example 22 | 7.40 | 29.80 | 12.60 | 3.00 | 29.93 | 16.89 |
| Example 23 | 6.60 | — | — | 3.00 | — | — |

Referring to Table 1 and FIGS. 21 to 26, the organic light emitting diodes of Examples 13 to 23 had a sharply lower driving voltage than those of Comparative Examples 2 and 3. In addition, the organic light emitting diodes of Examples 13 to 23 had a sharply low driving voltage, and very good high current efficiency and electric power efficiency.

Without being bound by theory, it is believed that these measurement results of the organic light emitting diodes according to embodiments of the present invention come from combination balance of holes and electrons in the emission layer. The compounds of Examples 13 to 23 turned out to have excellent electron injection and transport characteristics compared with Alq, a general electron transport material.

As described above, embodiments provide compounds that can act as a hole injection, hole transport, light emitting, or electron injection and/or transport material, and also acts as a light emitting host along with a dopant. It is preferable that displays simultaneously have improved luminous efficiency and life-span in order to be larger. In order to increase the luminous efficiency, smooth combination between holes and electrons in an emission layer is needed. If an organic material has slower electron mobility than hole mobility, it has a drawback of inefficient combination between holes and electrons. Accordingly, a compound that increases electron injection and mobility from a cathode and simultaneously prevents movement of holes is desirable. The compounds according to embodiments may be applied to an organic photoelectric device such as an organic light emitting diode, and thus provide an organic photoelectric device having a low driving voltage, and improved life-span and efficiency.

A device may have a decreased life-span if the material therein crystallizes due to Joule heat generated when it is driven. In order to solve this problem, 2-(4-biphenyl)-5-(4-t-butylphenyl)-1,3,4-oxadiazole (PBD) (Jpn. J. Appl. Phys., 27, L269 1988) with a rapid transfer speed has been suggested, but it lacks thermal stability and thereby still has a problem of crystallization when a device is driven. In addition, BCP and an aluminum mixed coordination complex (BAlq, bis(2-methyl-8-quinolinolate)-4-(phenylphenolate) aluminum), which is excellent in lowering hole mobility, have been actively researched. While these materials have excellent characteristic in lowering hole mobility, a problem of deteriorating the electron injection characteristic and being crystallized when a device is driven still remains, and accordingly these materials are not satisfactory. Therefore, there is a strong need for an organic compound having excellent electron injection and mobility and high thermal stability, and that prevents crystallization when a device is driven. Thus, the organic light emitting diodes according to embodiments of the present invention, which may provide a combination balance of holes and electrons in the emission layer, and may prevent crystallization, may be particularly suitable for an organic photoelectric device.

As described above, embodiments relate to a compound for an organic photoelectric device and an organic photoelectric device including the same. The material for an organic photoelectric device may decrease a driving voltage of an organic photoelectric device including the same due to excellent thermal stability, and improve life-span and efficiency and the organic photoelectric device.

Exemplary embodiments have been disclosed herein, and although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A compound for an organic photoelectric device, represented by the following Chemical Formula 1:

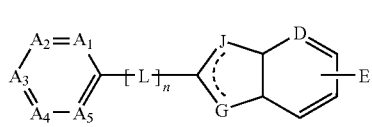

[Chemical Formula 1]

wherein, in Chemical Formula 1

$A_1$ to $A_5$ are the same or different, and are $CR_1$ to $CR_5$ or N, provided that three or less of $A_1$ to $A_5$ are N, when one of $A_1$ to $A_5$ is N, the remaining four of $A_1$ to $A_5$ are respectively selected from the group of $CR_1$ to $CR_5$, provided that at least two of $R_1$ to $R_5$ are not hydrogen, and when $A_1$ to $A_5$ are respectively $CR_1$ to $CR_5$, at least two of $R_1$ to $R_5$ are not hydrogen, and at least two of $R_1$ to $R_5$ are different, G is selected from the group of O, S, Se, and NR", J and D are the same or different, and are independently selected from the group of CR' and N, provided that when G is not NR", J is N, $R_1$ to $R_5$, R', and R" are independently selected from the group of hydrogen, a halogen, a nitrile, a cyano, a nitro, an amide, a carbonyl, an ester, a substituted or unsubstituted alkoxy, a substituted or unsubstituted alkenyl, a substituted or unsubstituted cycloalkyl, a substituted or unsubstituted aryl, a substituted or unsubstituted arylamine, a substituted or unsubstituted heteroarylamine, a substituted or unsubstituted C2 to C20 heterocycle, a substituted or unsubstituted amino, $BR_6R_7$, and $SiR_6R_7R_8$, where $R_6$ to $R_8$ are the same or different, and are independently selected from the group of a substituted or unsubstituted alkyl, and a substituted or unsubstituted aryl, E is selected from the group of hydrogen, a nitrile, a cyano, a nitro, an amide, a carbonyl, a substituted or unsubstituted alkyl, a substituted or unsubstituted fluoroalkyl, a substituted or unsubstituted cycloalkyl, a substituted or unsubstituted aryl, a substituted or unsubstituted heterocycle, and $SO_2R_9$, where $R_9$ is selected from the group of a nitrile, a cyano, a nitro, an amide, a carbonyl, a substituted or unsubstituted alkyl, a substituted or unsubstituted cycloalkyl, a substituted or unsubstituted aryl, and a substituted or unsubstituted heterocycle, L is selected from the group of a substituted or unsubstituted aryl and a substituted or unsubstituted heteroaryl, and n is 0 or 1, and wherein the compound for an organic photoelectric device has an asymmetric structure of the ring including $A_1$ to $A_5$, where upper and lower substituents are different from each other with respect to the axis including $A_3$.

2. The compound as claimed in claim 1, wherein the compound is represented by the following Chemical Formula 2:

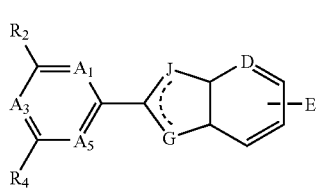

[Chemical Formula 2]

wherein, in Chemical Formula 2, $A_1, A_3$, and $A_5$ are the same or different, and are $CR_1$, $CR_3$, and $CR_5$, or N, where $R_1$, $R_3$, and $R_5$ are the same or different and are selected from the group of hydrogen and a substituted or unsubstituted alkyl, G is selected from the group of O, S, Se, and NR", J and D are the same or different, and are independently selected from the group of CR' and N, provided that when G is not NR", J is N, where R' and R" are the same or different, and are independently selected from the group of a nitrile, a cyano, a nitro, an amide, a carbonyl, a substituted or unsubstituted cycloalkyl, a substituted or unsubstituted aryl, and a substituted or unsubstituted C2 to C20 heterocycle, $R_2$ and $R_4$ are the same or different, and are independently selected from the group of hydrogen, a halogen, a nitrile, a cyano, a nitro, an amide, a carbonyl, an ester, a substituted or unsubstituted alkoxy, a substituted or unsubstituted alkenyl, a substituted or unsubstituted cycloalkyl, a substituted or unsubstituted aryl, a substituted or unsubstituted arylamine, a substituted or unsubstituted heteroarylamine, a substituted or unsubstituted C2 to C20 heterocycle, a substituted or unsubstituted amino, $BR_6R_7$, and $SiR_6R_7R_8$, where $R_6$ to $R_8$ are the same or different, and are independently selected from the group of a substituted or unsubstituted alkyl, and a substituted or unsubstituted aryl, and E is selected from the group of hydrogen, a nitrile, a cyano, a nitro, an amide, a carbonyl, a substituted or unsubstituted alkyl, a substituted or unsubstituted fluoroalkyl, a substituted or unsubstituted cycloalkyl, a substituted or unsubstituted aryl, a substituted or unsubstituted heterocycle, and $SO_2R_9$, where $R_9$ is selected from the group of a nitrile, a cyano, a nitro, an amide, a carbonyl, a substituted or unsubstituted alkyl, a substituted or unsubstituted cycloalkyl, a substituted or unsubstituted aryl, and a substituted or unsubstituted heterocycle.

3. The compound as claimed in claim 2, wherein $R_2$ and $R_4$ of Chemical Formula 2 are different from each other.

4. The compound as claimed in claim 1, wherein the $A_1$ and $A_5$ are different from each other, and $A_2$ and $A_4$ are different.

5. The compound as claimed in claim 1, wherein $R_1$ to $R_5$, R', and R" of Chemical Formula 1 are independently a substituted or unsubstituted C6 to C40 aryl.

6. The compound as claimed in claim 1, wherein $R_1$ to $R_5$, R', and R" are independently an arylamine selected from the group of diphenyl amine, dinaphthyl amine, dibiphenyl amine, phenyl naphthyl amine, phenyl diphenyl amine, ditolyl amine, phenyl tolyl amine, carbazole, and triphenyl amine.

7. The compound as claimed in claim 1, wherein $R_1$ to $R_5$, R', and R" are a substituted or unsubstituted C2 to C20 heterocycle selected from the group of thiophene, furan, pyrrole, imidazolyl, thiazolyl, oxazolyl, oxadiazolyl, triazolyl, pyridinyl, pyridazine, quinolinyl, isoquinolinine, acridyl, imidazopyridinyl, and imidazopyrimidinyl.

8. The compound as claimed in claim 7, wherein when the substituted or unsubstituted C2 to C20 heterocycle is imidazole or triazole, the substituent linked to nitrogen (N) of the imidazole or triazole is selected from the group of a substituted or unsubstituted alkyl, a substituted or unsubstituted cycloalkyl, a substituted or unsubstituted aryl, and a substituted or unsubstituted heterocycle.

9. The compound as claimed in claim 1, wherein:

one selected from $R_1$ to $R_5$, R', and R" of Chemical Formula 1 includes a substituent selected from the group of an amine substituted cycloalkyl, an amine substituted aryl, and an amine substituted C2 to C20 heterocycle, and another from $R_1$ to $R_5$, R', and R" of Chemical Formula 1 includes a substituent selected from the group of a nitrile, a nitro, an amide, a carbonyl, and a substituted or unsubstituted C2 to C20 heterocycle.

10. An organic photoelectric device, comprising:
an anode,
a cathode, and
at least one organic layer interposed between the anode and cathode, wherein the at least one organic layer includes the compound for an organic photoelectric device as claimed in claim 1.

11. The organic photoelectric device as claimed in claim 10, wherein the compound for an organic photoelectric device is a host material or a charge transport material.

12. The organic photoelectric device as claimed in claim 10, wherein the at least one organic layer includes at least one of an emission layer, a hole transport layer (HTL), a hole injection layer (HIL), an electron transport layer (ETL), and an electron injection layer (EIL).

13. The organic photoelectric device as claimed in claim 10, wherein the at least one organic layer includes the compound for an organic photoelectric device and a reducing dopant.

14. The organic photoelectric device as claimed in claim 13, wherein the reducing dopant includes at least one of an alkaline metal, an alkaline earth metal, a rare earth element metal, an oxide of an alkaline metal, a halide of an alkaline metal, an organic complex of an alkaline metal, an oxide of an alkaline earth metal, a halide of an alkaline earth metal, an organic complex of an alkaline earth metal, an oxide of an alkaline earth metal, a halide of an alkaline earth metal, an organic complex of an alkaline earth metal, an oxide of a rare earth element metal, a halide of a rare earth element metal, and an organic complex of a rare earth element metal.

15. A display device comprising the organic photoelectric device according to claim 10.

16. A compound for an organic photoelectric device, represented by the following Chemical Formula 1:

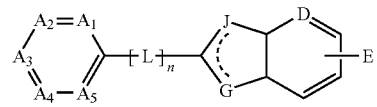

[Chemical Formula 1]

wherein, in Chemical Formula 1, $A_1$ to $A_5$ are the same or different, and are $CR_1$ to $CR_5$ or N, provided that three or less of $A_1$ to $A_5$ are N, when one of $A_1$ to $A_5$ is N, the remaining four of $A_1$ to $A_5$ are respectively selected from the group of $CR_1$ to $CR_5$, provided that at least two of $R_1$ to $R_5$ are not hydrogen, and when $A_1$ to $A_5$ are respectively $CR_1$ to $CR_5$, at least two of $R_1$ to $R_5$ are not hydrogen, G is selected from the group of O, S, Se, and NR", J and D are the same or different, and are independently selected from the group of CR' and N, provided that when G is not NR", J is N, $R_1$ to $R_5$, R', and R" are independently an arylamine selected from the group of diphenyl amine, dinaphthyl amine, dibiphenyl amine, phenyl naphthyl amine, phenyl diphenyl amine, ditolyl amine, phenyl tolyl amine, carbazole, and triphenyl amine, E is selected from the group of hydrogen, a nitrile, a cyano, a nitro, an amide, a carbonyl, a substituted or unsubstituted alkyl, a substituted or unsubstituted fluoroalkyl, a substituted or unsubstituted cycloalkyl, a substituted or unsubstituted aryl, a substituted or unsubstituted heterocycle, and $SO_2R_9$, where $R_9$ is selected from the group of a nitrile, a cyano, a nitro, an amide, a carbonyl, a substituted or unsubstituted alkyl, a substituted or unsubstituted cycloalkyl, a substituted or unsubstituted aryl, and a substituted or unsubstituted heterocycle, L is selected from the group of a substituted or unsubstituted aryl and a substituted or unsubstituted heteroaryl, and n is 0 or 1.

17. A compound for an organic photoelectric device, represented by the following Chemical Formula 1:

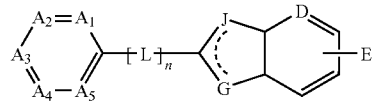

[Chemical Formula 1]

wherein, in Chemical Formula 1, $A_1$ to $A_5$ are the same or different, and are $CR_1$ to $CR_5$ or N, provided that three or less of $A_1$ to $A_5$ are N, when one of $A_1$ to $A_5$ is N, the remaining four of $A_1$ to $A_5$ are respectively selected from the group of $CR_1$ to $CR_5$, provided that at least two of $R_1$ to $R_5$ are not hydrogen, and when $A_1$ to $A_5$ are respectively $CR_1$ to $CR_5$, at least two of $R_1$ to $R_5$ are not hydrogen, G is selected from the group of O, S, Se, and NR", J and D are the same or different, and are independently selected from the group of CR' and N, provided that when G is not NR", J is N, one selected from $R_1$ to $R_5$, R', and R" of Chemical Formula 1 includes a substituent selected from the group of an amine substituted alkyl, an amine substituted cycloalkyl, an amine substituted aryl, and an amine substituted heterocycle, and another from $R_1$ to $R_5$, R', and R" of Chemical Formula 1 includes a substituent selected from the group of a nitrile, a nitro, an amide, a carbonyl, and a substituted or unsubstituted heterocycle, E is selected from the group of hydrogen, a nitrile, a cyano, a nitro, an amide, a carbonyl, a substituted or unsubstituted alkyl, a substituted or unsubstituted fluoroalkyl, a substituted or unsubstituted cycloalkyl, a substituted or unsubstituted aryl, a substituted or unsubstituted heterocycle, and $SO_2R_9$, where $R_9$ is selected from the group of a nitrile, a cyano, a nitro, an amide, a carbonyl, a substituted or unsubstituted alkyl, a substituted or unsubstituted cycloalkyl, a substituted or unsubstituted aryl, and a substituted or unsubstituted heterocycle, L is selected from the group of a substituted or unsubstituted aryl and a substituted or unsubstituted heteroaryl, and n is 0 or 1.

* * * * *